(12) United States Patent
Dobosy et al.

(10) Patent No.: US 10,886,006 B2
(45) Date of Patent: Jan. 5, 2021

(54) METHODS FOR VARIANT DETECTION

(71) Applicant: Integrated DNA Technologies, Coralville, IA (US)

(72) Inventors: Joseph Dobosy, Coralville, IA (US); Caifu Chen, Palo Alto, CA (US); Mark Aaron Behlke, Coralville, IA (US); Garrett Richard Rettig, Coralville, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 200 days.

(21) Appl. No.: 15/487,401

(22) Filed: Apr. 13, 2017

(65) Prior Publication Data
US 2017/0253925 A1    Sep. 7, 2017

Related U.S. Application Data

(63) Continuation-in-part of application No. 15/361,280, filed on Nov. 25, 2016.

(60) Provisional application No. 62/339,317, filed on May 20, 2016, provisional application No. 62/259,913, filed on Nov. 25, 2015.

(51) Int. Cl.
| | | |
|---|---|---|
| *C12P 19/34* | (2006.01) | |
| *G16B 30/00* | (2019.01) | |
| *C12Q 1/6858* | (2018.01) | |

(52) U.S. Cl.
CPC ............ *G16B 30/00* (2019.02); *C12Q 1/6858* (2013.01); *C12Y 301/26004* (2013.01)

(58) Field of Classification Search
None
See application file for complete search history.

(56) References Cited

U.S. PATENT DOCUMENTS

| | | | |
|---|---|---|---|
| 8,911,948 B2 | 12/2014 | Walder et al. | |
| 2009/0325169 A1* | 12/2009 | Walder ................ | C12Q 1/6844 435/6.18 |
| 2010/0203524 A1* | 8/2010 | Efcavitch ............ | C12N 9/1241 435/6.12 |
| 2013/0288245 A1 | 10/2013 | Walder et al. | |
| 2015/0191707 A1 | 7/2015 | Behlke et al. | |

FOREIGN PATENT DOCUMENTS

| | | | |
|---|---|---|---|
| CA | 2 949 315 | 11/2009 | |
| JP | 2011-521624 | 7/2011 | |
| WO | WO 2009/135093 | 11/2009 | |
| WO | WO 2012/135053 | 10/2012 | |
| WO | WO 2013/142364 | 9/2013 | |
| WO | WO-2014093622 A2 * | 6/2014 | ............ C12N 15/86 |
| WO | 2014110528 | 7/2014 | |
| WO | WO-2014110528 A1 * | 7/2014 | ............ C12Q 1/686 |
| WO | WO 2014/143228 | 9/2014 | |
| WO | 2015073931 | 5/2015 | |
| WO | WO-2015073931 A1 * | 5/2015 | ............ C12P 19/34 |

OTHER PUBLICATIONS

Dobosy et al., "RNase H-dependent PCR (rhPCR): improved specificity and single nucleotide polymorphism detection using blocked cleavable primers," BMC Biotechnology 11:80 (2011).
Franke et al., "Detection, Imputation, and Association Analysis of Small Deletions and Null Alleles on Oligonucleotide Arrays", Am J Hum Genet. 82(6):1316-33 (2008).
N.N, "TaqMan Drug Metabolism Genotyping Assays for Triallelic SNPs", Application note TaqMan Drug Metabolism Genotyping Assays, pp. 1-4 (Jan. 2008).
International Search Report and Written Opinion by the ISA for International Application No. PCT/US2016/063771; dated May 15, 2007, pp. 1-27.
International Preliminary Report on Patentability by the ISA for International Application No. PCT/US2016/063771; dated May 29, 2018, pp. 1-17.
International Search Report by the ISA for International Application No. PCT/US2017/034289; dated Dec. 4, 2017, pp. 1-5.
Written Opinion by the ISA for International Application No. PCT/US2017/034289; dated Dec. 4, 2017, pp. 1-9.
Non-Final Office Action for U.S. Appl. No. 15/361,280, dated Nov. 14, 2018 (pp. 1-9).
Annex to form PCT/ISA/208 from International Application No. PCT/US2016/063771 dated Mar. 10, 2017 (pp. 1-3).
Brinkman et al., "Easy quantitative assessment of genome editing by sequence trace decomposition", Nucleic Acids Research, 42:e168 (2014).
Chon et al., "RNase H2 roles in genome integrity revealed by unlinking its activities", Nucleic Acids Research 41:3130 (2013).
Kim et al., "A guide to genome engineering with programmable nucleases," Nature reviews. Genetics, 15:321-334 (2014).
Mean et al., "Modification of the enzyme mismatch cleavage method using T7 endonuclease I and silver staining", BioTechniques, 36:758-760 (2004).
Pinello, et al., "Analyzing CRISPR genome-editing experiments with CRISPResso", Nature biotechnology, 34, 695-697 (2016).
Thomas et al., "High-throughput genome editing and phenotyping facilitated by high resolution melting curve analysis," PloS one 9:e114632 (2014).
Weiner et al., "Site-directed mutagenesis of double-stranded DNA by the polymerase chain reaction", Gene 151:119-123 (1994).

(Continued)

*Primary Examiner* — Kenneth R Horlick
(74) *Attorney, Agent, or Firm* — McDonnell Boehnen Hulbert & Berghoff LLP

(57) ABSTRACT

The invention can be used to provide a more efficient and less error-prone method of detecting variants in DNA, such as SNPs and indels. The invention also provides a method for performing inexpensive multiplex assays. The invention also provides methods for detection of DNA sequences altered after cleavage by a targetable endonuclease, such as the CRISPR Cas9 protein from the bacterium *Streptococcus pyogenes*.

41 Claims, 13 Drawing Sheets

Specification includes a Sequence Listing.

(56) References Cited

OTHER PUBLICATIONS

Vouillot et al., "Comparison of T7E1 and surveyor mismatch cleavage assays to detect mutations triggered by engineered nucleases," G3 (Bethesda), 5:407-415 (2015).
Yang et al., "Fast and sensitive detection of indels induced by precise gene targeting", Nucleic acids research, 43:e59 (2015).
Final Office Action for U.S. Appl. No. 15/361,280, dated Aug. 9, 2019 (pp. 1-9).
Non-Final Office Action for U.S. Appl. No. 15/604,204, dated Apr. 3, 2019 (pp. 1-16).
U.S. Appl. No. 15/361,280, filed Nov. 25, 2016, Dobosy et al.
U.S. Appl. No. 15/604,204, filed May 24, 2017, Dobosy et al.
U.S. Appl. No. 16/374,751, filed Apr. 4, 2019, Dobosy et al.
U.S. Appl. No. 16/374,752, filed Apr. 4, 2019, Dobosy et al.
International Preliminary Report on Patentability for International Application No. PCT/US2017/034289; dated Oct. 15, 2019, pp. 1-10.
Non-Final Office Action for U.S. Appl. No. 15/361,280, dated Apr. 30, 2020 (pp. 1-19).
Final Office Action for U.S. Appl. No. 15/604,204, dated Dec. 30, 2019 (pp. 1-14).

\* cited by examiner

Step 1: Multiplex rhPCR

Step 2: Purification

Step 3: Universal PCR

Step 4: Purification

METHODS FOR VARIANT DETECTION

CROSS-REFERENCE TO RELATED APPLICATIONS

This application is a continuation-in-part of U.S. application Ser. No. 15/361,280, filed Nov. 25, 2016, which claims the benefit of U.S. Provisional Application No. 62/339,317, filed May 20, 2016, and also claims the benefit of U.S. Provisional Application No. 62/259,913, filed Nov. 25, 2015, the disclosures of all of which are hereby incorporated by reference in their entireties.

FIELD OF THE INVENTION

The invention can be used to provide a more efficient and less error-prone method of detecting variants in DNA, such as single nucleotide polymorphisms (SNPs), multi-nucleotide polymorphisms (MNPs), and indels. The invention also provides a method for performing inexpensive multi-color assays, and provides methods for visualizing multiple allele results in a two-dimensional plot. The invention also provides methods for detection of DNA sequences altered after cleavage by a targetable endonuclease, such as the CRISPR Cas9 protein from the bacterium *Streptococcus pyogenes*.

BACKGROUND OF THE INVENTION

RNase H2-dependent PCR (rhPCR) (see U.S. Patent Application Publication No. US 2009/0325169 A1, incorporated by reference herein in its entirety) and standard allele-specific PCR (ASPCR) can both be utilized for mutation detection. In ASPCR, the DNA polymerase performs the mismatch discrimination by detection of a mismatch at or near the 3' end of the primer. While ASPCR is sometimes successful in mismatch detection, the discrimination can be limited, due to the low mismatch detection ability of wild-type DNA polymerases.

In contrast with ASPCR, the mismatch sensitivity of the RNase H2 enzyme in rhPCR allows for both sensitive detection of DNA mutations, and elimination of primer-dimer artifacts from the reaction. When attempting to detect DNA mutations with rhPCR, however, placement of the mismatch within the primer is important. The nearer to the cleavable RNA the mismatch is located, the more discrimination is observed from the RNase H2 enzyme, and the greater the discrimination of the resulting rhPCR assay. Given the fact that most common wild-type DNA polymerases such as Taq often display low levels of mismatch detection, the polymerase cannot be solely relied upon to perform this discrimination after RNase H2 cleavage. Coupled with the repeated interrogation desired from every cycle of standard rhPCR, placing the mismatch anywhere other than immediately opposite the RNA is undesirable when utilizing these polymerases.

There is thus a need for assays with improved mismatch sensitivity.

In addition, there is a need for improved methods for detection of mutations altered after cleavage by targetable endonucleases, such as the CRISPR Cas9 protein. A commonly used method to detect mutations introduced into genomic DNA following repair of dsDNA cleavage events is the enzymatic mismatch cleavage assay (EMCA). EMCA assays cleave at sites where base mismatches are present in dsDNA. For EMCA detection of the mutations introduced into DNA following Cas9 cleavage and repair, genomic DNA from cells is harvested and the regions around the dsDNA cut site is amplified by PCR using primers that flank the cut site. Typically 100-1000 base amplicons are used for this purpose. Following completion of amplification, heteroduplexes are formed by heating the reaction products and allowing them to re-anneal, which leads to formation of homoduplex WT/WT, Mut/Mut or heteroduplex WT/Mut or Mut1/Mut2 variants. The dsDNAs are then subjected to cleavage by a mismatch endonuclease (such as T7EI, Surveyor, etc.). Heteroduplexes are cleaved and the presence of shorter fragments is detected by gel electrophoresis, capillary electrophoresis, or any of a number of methods known to those of skill in the art. Although such an assay is fast and inexpensive, it often does not accurately reflect the changes that are actually generated from the CRISPR mutagenesis process. If the same mutation is introduced a large number of times, Mut/Mut homodimers form, which are not detected. Further, the mismatch endonuclease enzymes often fail to cleave single-base events, leading to yet another class of mutations that are undetected. Thus an EMCA assay will almost always underestimate the extent of genome editing that occurred after Cas9 dsDNA cleavage and repair.

An alternative method of analysis involves large scale DNA sequencing using "Next-Gen" sequencing (NGS) methods of the modified DNA, which is highly accurate, but is slow and costly. Other methods are available to assess the mutation outcome following CRISPR/Cas9 cleavage and repair. For example, Sanger sequencing results can be analyzed using sequence trace decomposition ("TIDE" analysis); fluorescent-labeled primer-extension on an amplicon spanning the Cas9 cut site can be used to map indels using Indel Detection by Amplicon Analysis (IDAA); or high resolution melt analysis (HRM) can be applied to PCR amplicons that span the Cas9 cut site. However, none of these methods approaches the accuracy of NGS analysis, while all are more costly and slower to perform than EMCA methods. Thus, improved methods are needed to assess the frequency of mutations that arise from genome editing experiments that are rapid and low cost.

BRIEF SUMMARY OF THE INVENTION

The disclosure provides assays making use of high discrimination polymerase mutants or other high mismatch discrimination polymerases to create a new assay design that can utilize mismatches located 5' of the RNA.

The invention can be used to provide a more efficient and less error-prone method of detecting mutations in DNA, such as SNPs and indels. The invention also provides a method for performing inexpensive multi-color assays. The invention also provides methods for detection of DNA sequences altered after cleavage by a targetable endonuclease, such as the CRISPR Cas9 protein from the bacterium *Streptococcus pyogenes*.

These and other advantages of the invention, as well as additional inventive features, will be apparent from the description of the invention provided herein.

BRIEF DESCRIPTION OF THE DRAWINGS

FIG. 2A is a "Universal" SNP assay for rs351855 performed with WT Taq polymerase. FIG. 2B is a "Universal" SNP assay for rs351855 performed with mutant H784Q Taq polymerase, demonstrating greatly enhanced discrimination between each of the allelic variants as observed by the greater separation of the clusters in the mutant Taq case. In both cases, the no template controls (NTCs) (squares) are near the (0,0) coordinates, as desired. Allele 1 samples are shown as circles, allele 2 samples as diamonds, and heterozygotes as triangles. Each reaction was performed in triplicate.

In FIG. 5A, diamonds: no template controls (NTCs); squares: allele G (allele 1) samples; circles: allele A (allele 2) samples; triangles: heterozygotes. In FIG. 5B, diamonds: no template controls (NTCs); squares: allele G (allele 1) samples; circles: allele C (allele 3) samples; triangles: heterozygotes.

In FIG. 8A, diamonds: no template controls (NTCs); squares: allele G samples; circles: allele C samples; and triangles: heterozygotes. The resulting data correlates with the test input.

FIG. 13A: the percentage of mutated templates is consistently underestimated by T7EI EMCA (empty squares), when compared with NGS results (grey circles) on the same samples. FIG. 13B: using the same samples from FIG. 13A, the percentage of mutations detected is seen to be much more accurately estimated by the qPCR methods of the disclosure (empty squares) when compared with NGS results.

DETAILED DESCRIPTION OF THE INVENTION

Figure 1:
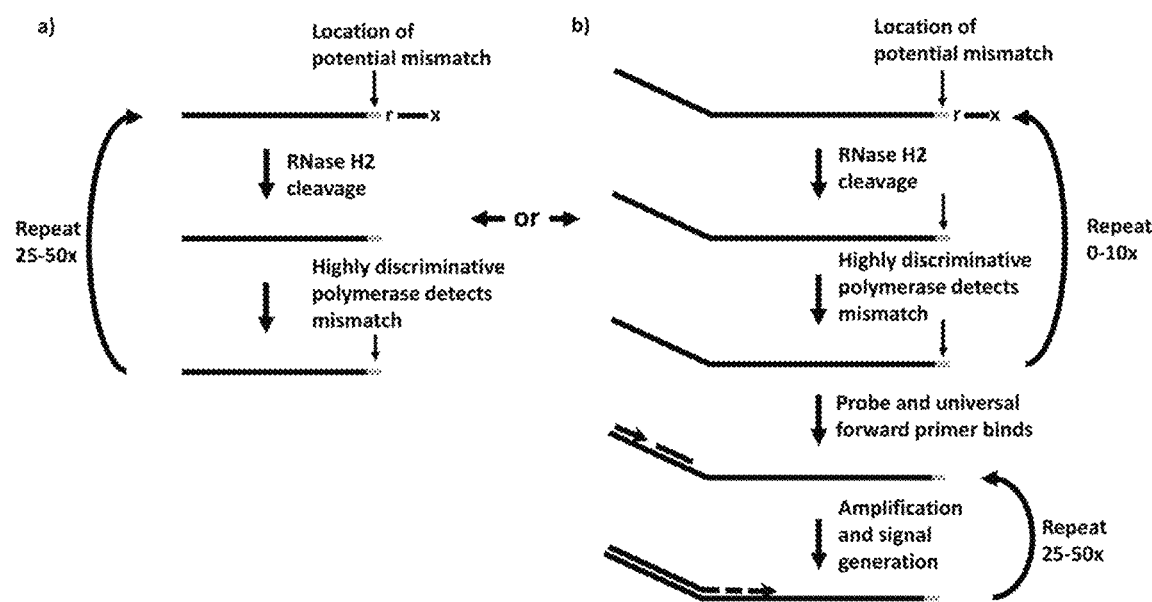
FIG. 1 is a diagram showing two primer designs utilized in this invention. Part a) is a blocked-cleavable primer designed so that the SNP of interest is 5' of the RNA base when hybridized to a template. The RNase H2 cleaves, leaving a 3' interrogating base, which is determined to be either a match or a mismatch by the highly discriminative DNA polymerase. Thermal cycling allows for this process to continue. Part b) illustrates the RNase H2 cleavage and SNP detection are identical to a), but the primer also includes a 5' "tail" domain that includes a binding site for a probe and a universal forward primer. After 1-10 cycles of discrimination with the RNase H2 and the polymerase, the highly concentrated universal forward primer comes to dominate the amplification, degrading the probe when it amplifies. This cycle is repeated 25-50×, generating the output signal. This primer design may be multiplexed, allowing for one-tube multi-color assay designs.

The invention pertains to a methods of single-nucleotide polymorphism (SNP) discrimination utilizing blocked-cleavable rhPCR primers (see U.S. Patent Application Publication No. US 2009/0325169 A1, incorporated by reference herein in its entirety) and a DNA polymerase with high levels of mismatch discrimination. In one embodiment, the mismatch is placed at a location other than opposite the RNA base. In these situations, the majority of the discrimination comes not from the RNase H2, but from the high discrimination polymerase. The use of blocked-cleavable primers with RNase H2 acts to reduce or eliminate primer-dimers and provide some increased amount of SNP or indel (insertion/deletion) discrimination (FIG. 1a).

For the purposes of this invention, high discrimination is defined as any amount of discrimination over the average discrimination of WT *Thermus aquaticus* (Taq) polymerase. Examples include KlenTaq® DNA polymerase (Wayne Barnes), and mutant polymerases described in U.S. Patent Application Publication No. US 2015/0191707 (incorporated by reference herein in its entirety) such as H784M, H784S, H784A and H784Q mutants.

In a further embodiment a universal detection sequence(s) is added to the 5'-end of the blocked-cleavable primers. The detection sequence includes a binding site for a probe, and a binding site for a universal amplification primer. The primer binding site is positioned at or near the 5'-end of the final oligonucleotide and the probe binding site is positioned internally between the universal primer site and the SNP-detection primer domain. Use of more than one such chimeric probe in a detection reaction wherein distinct probe binding sites are employed allows primers to be multiplexed and further allows for multiple color detection of SNPs or other genomic features. Blocked-cleavable rhPCR primers reduce or eliminate primer-dimers. Primer-dimers are a major problem for use of "universal" primer designs in SNP detection assays, and that limits their utility (FIG. 1b). Combining a universal amplification/detection domain with a SNP primer domain in blocked-cleavable primer format overcomes this difficulty.

Previously, the best preferred embodiment for rhPCR SNP discrimination employed blocked-cleavable primers having the mismatch (SNP site) positioned opposite the single RNA base (cleavage site). While this works for many SNP targets, there are base match/mismatch pairings where sufficient discrimination is not obtained for robust base calling. Moreover, due to the high level of differential SNP discrimination observed with rhPCR, end-point detection can be difficult, especially with heterozygous target DNAs. In the proposed method, the RNA base is identical in both discriminating primers, eliminating this issue.

In one embodiment of the invention, the method involves the use of blocked-cleavable primers wherein the mismatch is placed 1-2 bases 5' of the RNA. In a further embodiment, the method involves the use of blocked-cleavable primers with three or more DNA bases 3' of an RNA residue, and the primers are designed such that the mismatch is placed immediately 5' of the RNA.

Following cleavage by RNase H2, the remaining primer has a DNA residue positioned at the 3'-end exactly at the SNP site, effectively creating an ASPCR primer. In this configuration, a high-specificity DNA polymerase can discriminate between match and mismatch with the template strand (FIGS. 1a and b). Native DNA polymerases, such as Taq DNA polymerase, will show some level of discrimination in this primer configuration, and if the level of discrimination achieved is not sufficient for robust SNP calling in a high throughput assay format then the use of polymerases with improved template discrimination can be used. In one embodiment, mutant DNA polymerases, such as those disclosed in U.S. Patent Application Publication No. US 2015/0191707 (incorporated by reference herein in its entirety) or any other polymerase designed or optimized to improve template discrimination can be used. When using polymerases with increased mismatch discrimination, the final level of match/mismatch discrimination achieved will be additive with contributions from both the ASPCR primer polymerase interaction and from the rhPCR primer/RNaseH2 interaction. Further, the use of blocked-cleavable primers reduces risk of primer-dimer formation, which produces false-positive signals, making the overall reaction more robust and having higher sensitivity and higher specificity. The relative contributions of each component of the assay may vary with use of different polymerases, different blocking groups on the 3'-end of the primer and different RNase H2 enzymes.

In another embodiment, the invention may utilize a "tail" domain added to the 5' end of the primer, containing a universal forward primer binding site sequence and optionally a universal probe sequence. This tail would not be complementary to the template of interest, and when a probe is used, the tail would allow for inexpensive fluorescent signal detection, which could be multiplexed to allow for multiple color signal detection in qPCR (FIG. 1b). In one embodiment, 1-10 cycles of initial cycling and discrimination occurs from both the RNase H2 and the DNA polymerase. After this initial pre-cycling, a highly concentrated and non-discriminatory universal forward primer comes to dominate the amplification, degrading the probe and generating the fluorescent signal when the DNA amplifies. This cycle is repeated 25-50×, allowing for robust detection. This assay design is prone to issues with primer-dimers, and the presence of the blocked-cleavable domain in the primers will suppress or eliminate these issues.

In another embodiment, a forward primer is optionally used with a reverse primer, and a tail domain is added to the 5' end of one or both of a forward and reverse primer set. The tail domain comprises a universal forward primer binding site. The primers can be used to hybridize and amplify a target such as a genomic sample of interest. The primers would add universal priming sites to the target, and further cycles of amplification can be performed using universal primers that contain adapter sequences that enable further processing of the sample, such as the addition of P5/P7 flow cell binding sites and associated index or barcoding sequences useful in adapters for next-generation sequencing (see FIG. 9). In a further embodiment a high fidelity polymerase is used, which will further lower the rate of base misincorporation into the extended product and increase the accuracy of the methods of the invention.

As noted in U.S. Patent Application Publication No. US 2009/0325169 (incorporated by reference herein in its entirety), RNase H2 can cleave at positions containing one or more RNA bases, at 2'-modified nucleosides such as 2'-fluoronucleosides. The primers can also contain nuclease resistant linkages such as phosphorothioate, phosphorodithioate, or methylphosphonate.

Further aspects of the disclosure pertain to detection of DNA sequences altered after cleavage by a targetable endonuclease, such as the CRISPR Cas9 protein from the bacterium *Streptococcus pyogenes*. This protein and similar ones have successfully been used for targeted genomic modification in the well documented Clustered Regularly Interspaced Short Palindromic Repeats (CRISPR) system.

In a further embodiment, the tailed primers detailed above could be used to detect editing events for genome editing technology. For example, CRISPR/Cas9 is a revolutionary strategy in genome editing that enables generation of targeted, double-stranded breaks (DSBs) in genomic DNA. Methods to achieve DSBs by CRISPR/Cas9—a bacterial immune defense system comprised of an endonuclease that is targeted to double-stranded DNA by a guide RNA—are widely used in gene disruption, gene knockout, gene insertion, etc. In mammalian cells, the endonuclease activity is followed by an endogenous repair process that leads to some frequency of insertions/deletions/substitutions in wild-type DNA at the target locus which gives the resultant genome editing.

RNase H-cleavable primers have been designed to flank edited loci in order to 1) generate locus-specific amplicons with universal tails, and 2) be subsequently amplified with indexed P5/P7 universal primers for next-generation sequencing. In pilot experiments, this strategy resulted in reliable, locus-specific amplification which captures CRISPR/Cas9 editing events in a high-throughput and reproducible manner. The key finding is that the overall targeted editing by this NGS-based method was determined to be 95%; whereas, previous enzymatic strategies suggested overall editing from the same samples was approximately 55% at the intended target site. Further, primers were designed to amplify off-target locations of genomic editing based on in silico predictions by internal bioinformatics tools.

These assays would be pooled for amplification of a single genomic DNA sample in order to capture the on-target as well as >100 potential sites for off-target genome editing mediated by sequence homology to the guide RNA. The results from this experiment would allow for 1) identification of CRISPR/Cas9 off-target sites and provide an assay for comparing strategies to reduce those effects, 2) improved design of the CRISPR/Cas9 off-target prediction algorithm, and 3) improved design of primer sets.

Thus, in further aspects, the disclosure provides methods that employ the above-described universal rhPCR assay system to detect mutations generated by a targetable endonuclease such as Cas9 or Cpf1. The rhPCR assays according to these aspects of the disclosure utilizes a thermostable RNase H2 enzyme, and optionally a DNA polymerase with enhanced mismatch discrimination. The RNase H2 cleaves at the single RNA residue only when the primer oligonucleotide is duplexed with a target nucleic acid, which removes a 3'-blocking group and activates the primer. The DNA polymerase uses the primer to initiate DNA synthesis and, in multiple cycles, supports PCR. Discrimination of mutations is achieved by the action of the RNase H2 or the combined action of both the RNase H2 and the DNA polymerase, wherein the RNase H2 has reduced de-blocking activity when a mismatch is present and the DNA polymerase has reduced priming/DNA synthesis activity when a mismatch is present. In one embodiment, the primers comprise multiple functional domains including (from the 5'-end): a universal primer domain, a universal probe binding domain, a target-specific primer domain, a single RNA residue (cleavable linkage), a short 3'-extension domain, and a 3'-blocking group that prevents the oligonucleotide from priming DNA synthesis. Cleavage by RNase H2 removes the RNA residue, 3'-extension domain, and 3'-blocking group.

In some embodiments, a second assay is present in the reaction and runs as a 2-color multiplex, targeting the RNase P gene or some other control gene. This second assay allows for normalization to an internal control gene that was not targeted by the CRISPR genome editing reaction. This control assay may be performed as either a standard three-oligonucleotide 5' nuclease assay, or as a second rhPCR-based universal assay.

In another embodiment, the primers lack the universal 5' domain, but still retain the 3' removable blocking group. In this alternative embodiment, a standard 5' nuclease fluorescence-quenched probe is placed between the forward and reverse primers. The probe is positioned within the amplicon such that it lies outside of any region that may be altered by the genome editing event.

Figure 12:
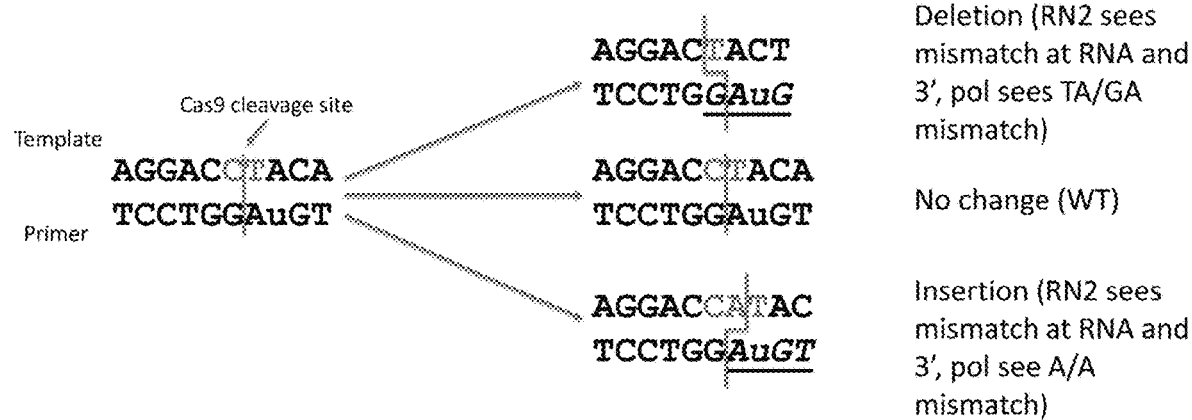
FIG. 12 shows placement of the RNA residue relative to the most common cleavage site for the methods of the disclosure (such as in Example 10). The RNA is shown in lower case, while DNA residues are shown in upper case. Cas9 cleavage site is shown with a line through both strands of DNA. RN2=RNase H2 enzyme; pol=polymerase.

In each experiment, relative position of the discriminatory (i.e., mutation interrogating) primer on the sequence is important. RNase H2 cleaves 5' of an RNA residue. Placement of the primer so that the RNA residue binds two nucleotides after the most common cleavage site is important for recognition of the mutagenized samples. A diagram of this principle is shown in FIG. 12. In the Wild-Type (WT) samples, amplification occurs normally, as neither the RNase H2 nor the DNA polymerase are hindered in their functions. If an insertion is introduced to the sequence, a mismatch for both the RNase H2 and the DNA polymerase are produced, allowing two independent chances to distinguish mutant from WT. The same interrogation of the samples is achieved if a deletion is present—both the RNase H2 and the DNA polymerase detect the mismatches generated (FIG. 12). This double level of interrogation allows for very precise quantification of the presence of mutated DNA in a heterogeneous sample.

Thus, in another aspect, the disclosure provides methods of detecting variations in target DNA sequences that have been altered with a gene editing enzyme, the methods comprising: (a) providing a reaction mixture comprising: (i) an oligonucleotide primer having a cleavage domain positioned 5' of a blocking group and 3' of a position of variation, the blocking group linked at or near the end of the 3'-end of the oligonucleotide primer wherein the blocking group prevents primer extension and/or inhibits the primer from serving as a template for DNA synthesis; (ii) a sample nucleic acid that may or may not have the target sequence, and where the target sequence may or may not have the variation; (iii) a cleaving enzyme; and (iv) a polymerase; (b) hybridizing the primer to the target DNA sequence to form a double-stranded substrate; (c) cleaving the hybridized primer, if the primer is complementary at the variation, with the cleaving enzyme at a point within or adjacent to the cleavage domain to remove the blocking group from the primer; and (d) extending the primer with the polymerase.

In some embodiments, the target DNA sequence has been treated with a CRISPR enzyme. In some embodiments, the target DNA sequence has been treated with a Cas9 or Cpf1 enzyme. In some embodiments, the cleaving enzyme is a hot start cleaving enzyme which is thermostable and has reduced activity at lower temperatures. In some embodiments, the cleaving enzyme is an RNase H2 enzyme. In some embodiments, the cleaving enzyme is *Pyrococcus abyssi* RNase H2 enzyme. In some embodiments, the cleaving enzyme is a chemically modified hot start cleaving enzyme which is thermostable and has reduced activity at lower temperatures. In some embodiments, the hot start cleaving enzyme is a chemically modified *Pyrococcus abyssi* RNase H2. In some embodiments, the cleaving enzyme is a hot start cleaving enzyme that is reversibly inactivated through interaction with an antibody at lower temperatures.

In some embodiments, the cleavage domain comprises at least one RNA base, and the cleaving enzyme cleaves between the position complementary to the variation and the RNA base. In some embodiments, the cleavage domain comprises at least one RNA base located 3' of the position of variation, and comprises one DNA base between the position of variation and the RNA base. In some embodiments, there are no DNA bases between the position of variation and the RNA base. In other embodiments, the RNA base is located within the position of variation. In some embodiments, the cleavage domain comprises one or more 2'-modified nucleosides, and the cleaving enzyme cleaves between the position complementary to the variation and the one or more modified nucleosides. In some embodiments, the one or more modified nucleosides are 2'-fluoronucleosides.

In some embodiments, the polymerase is a high-discrimination polymerase. In some embodiments, the polymerase is a mutant H784Q Taq polymerase. In some embodiments, the mutant H784Q Taq polymerase is reversibly inactivated via chemical, aptamer, or antibody modification. In some embodiments, the primer contains a 5' tail sequence that comprises a universal primer sequence and optionally a universal probe sequence, wherein the tail is non-complementary to the target DNA sequence.

In some embodiments, the methods of this aspect of the disclosure further comprise (e) detection of an internal control gene not targeted by the gene editing enzyme; and (f) normalization of the results of steps (a)-(d) to the results of step (e). In some embodiments, the internal control gene not targeted by the gene editing enzyme is the RNase P gene. In some embodiments, the reaction mixture further comprises a control oligonucleotide primer specific for the internal control gene not targeted by the gene editing enzyme, wherein the control oligonucleotide primer comprises a cleavage domain positioned 5' of a blocking group and 3' of a position of variation, the blocking group linked at or near the end of the 3'-end of the oligonucleotide primer wherein the blocking group prevents primer extension and/or inhibits the primer from serving as a template for DNA synthesis. In some embodiments, the internal control gene not targeted by the gene editing enzyme is detected using a three-oligonucleotide 5' nuclease assay.

In another aspect, the disclosure provides methods of target enrichment comprising: (a) providing a reaction mixture comprising: (i) a first oligonucleotide primer having a tail domain that is not complementary to a target sequence, the tail domain comprising a first universal primer sequence; a cleavage domain positioned 5' of a blocking group and 3' of a position of variation, the blocking group linked at or near the end of the 3'-end of the first oligonucleotide primer wherein the blocking group prevents primer extension and/or inhibits the first primer from serving as a template for DNA synthesis; (ii) a sample nucleic acid that has been treated with a gene editing enzyme, which may or may not have the target sequence; (iii) a cleaving enzyme; and (iv) a polymerase; (b) hybridizing the first primer to the target DNA sequence to form a double-stranded substrate; (c) cleaving the hybridized first primer, if the first primer is complementary to the target, with the cleaving enzyme at a point within or adjacent to the cleavage domain to remove the blocking group from the first primer; and (d) extending the first primer with the polymerase.

In some embodiments, the target DNA sequence is a sample that has been treated with a CRISPR enzyme. In some embodiments, the target DNA sequence is a sample that has been treated with a Cas9 or Cpf1 enzyme. In some embodiments, the methods further comprise a second primer in reverse orientation to support priming and extension of the first primer extension product. In some embodiments, the second primer further comprises a tail domain comprising a second universal primer sequence. In some embodiments, steps (b)-(d) are performed 1-10 times. In some embodiments, the methods further comprise removing unextended primers from the reaction and hybridizing universal primers to the extension product to form a second extension product. In some embodiments, the universal primers further comprise tailed sequences for addition of adapter sequences to the second extension product. In some embodiments, sequencing is performed on the second extension product to determine the sequence of the target.

In some embodiments, the cleaving enzyme is a hot start cleaving enzyme which is thermostable and has reduced activity at lower temperatures. In some embodiments, the cleaving enzyme is an RNase H2 enzyme. In some embodiments, the cleaving enzyme is *Pyrococcus abyssi* RNase H2 enzyme. In some embodiments, the cleaving enzyme is a chemically modified hot start cleaving enzyme which is thermostable and has reduced activity at lower temperatures. In some embodiments, the hot start cleaving enzyme is a chemically modified *Pyrococcus abyssi* RNase H2. In some embodiments, the cleaving enzyme is a hot start cleaving enzyme that is reversibly inactivated through interaction with an antibody at lower temperatures which is thermostable and has reduced activity at lower temperatures. In some embodiments, the cleavage domain comprises at least one RNA base, and the cleaving enzyme cleaves between the position complementary to the variation and the RNA base.

In some embodiments, the cleavage domain comprises at least one RNA base located 3' of the position of variation, and comprises one DNA base between the position of variation and the RNA base. In some embodiments, there are no DNA bases between the position of variation and the RNA base. In other embodiments, the RNA base is located within the position of variation. In some embodiments, the cleavage domain comprises one or more 2'-modified nucleosides, and the cleaving enzyme cleaves between the position complementary to the variation and the one or more modified nucleosides. In some embodiments, the one or more modified nucleosides are 2'-fluoronucleosides. In some embodiments, the polymerase is a high-discrimination polymerase. In some embodiments, the polymerase is a mutant H784Q Taq polymerase. In some embodiments, the mutant H784Q Taq polymerase is reversibly inactivated via chemical, aptamer or antibody modification.

In another aspect, the disclosure provides blocked-cleavable primers for rhPCR, comprising: 5'-A-B-C-D-E-3', wherein A is optional and is a tail extension that is not complementary to a target; B is a sequence domain that is complementary to a target; C is a discrimination domain; D is a cleavage domain that, when hybridized to the target, is cleavable by RNase H2, and which comprises an RNA base; and E is a blocking domain that prevents extension of the primer.

In some embodiments, D is a cleavage domain that, when hybridized to the target, is cleavable by RNase H2, and which comprises an RNA base that is: separated from the discrimination domain by one base position, within the discrimination domain, or adjacent to the discrimination domain. In some embodiments, the RNA base is separated from the discrimination domain by one base position. In some embodiments, the RNA base is within the discrimination domain. In some embodiments, the RNA base is adjacent to the discrimination domain. For example, when the RNA base is adjacent to the discrimination domain, no intervening DNA residue is present between the RNA base and the discrimination domain.

In some embodiments, D comprises 1-3 RNA bases. In some embodiments, the cleavage domain comprises one or more of the following moieties: a DNA residue, an abasic residue, a modified nucleoside, or a modified phosphate internucleotide linkage. In some embodiments, a sequence flanking the cleavage site contains one or more internucleoside linkages resistant to nuclease cleavage. In some embodiments, the nuclease resistant linkage is a phosphorothioate. In some embodiments, the 3' oxygen atom of at least one of the RNA residues is substituted with an amino group, thiol group, or a methylene group. In some embodiments, the blocking group is attached to the 3'-terminal nucleotide of the primer. In some embodiments, A is comprised of a region that is identical to a universal forward primer and optionally a probe binding domain.

In some embodiments, the discrimination domain C does not comprise or overlap with the cleavage domain D. In some other embodiments, the discrimination domain C comprises the cleavage domain D. In some other embodiments, the discrimination domain C overlaps with the cleavage domain D.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention.

"Complement" or "complementary" as used herein means a nucleic acid, and can mean Watson-Crick (e.g., A-T/U and C-G) or Hoogsteen base pairing between nucleotides or nucleotide analogs of nucleic acid molecules.

"Fluorophore" or "fluorescent label" refers to compounds with a fluorescent emission maximum between about 350 and 900 nm.

"Hybridization" as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. "Identical" sequences refers to sequences of the exact same sequence or sequences similar enough to act in the same manner for the purpose of signal generation or hybridizing to complementary nucleic acid sequences. "Primer dimers" refers to the hybridization of two oligonucleotide primers. "Stringent hybridization conditions" as used herein means conditions under which hybridization of fully complementary nucleic acid strands is strongly preferred. Under stringent hybridization conditions, a first nucleic acid sequence (for example, a primer) will hybridize to a second nucleic acid sequence (for example, a target sequence), such as in a complex mixture of nucleic acids. Stringent conditions are sequence-dependent and will be different in different circumstances. Stringent conditions can be selected to be about 5-10° C. lower than the thermal melting point (™) for the specific sequence at a defined ionic strength pH. The Tm can be the temperature (under defined ionic strength, pH, and nucleic concentration) at which 50% of an oligonucleotide complementary to a target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

The terms "nucleic acid," "oligonucleotide," or "polynucleotide," as used herein, refer to at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequences. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods. A particular nucleic acid sequence can encompass conservatively modified variants thereof (e.g., codon substitutions), alleles, orthologs, single nucleotide polymorphisms (SNPs), and complementary sequences as well as the sequence explicitly indicated.

"Polymerase Chain Reaction (PCR)" refers to the enzymatic reaction in which DNA fragments are synthesized and amplified from a substrate DNA in vitro. The reaction typically involves the use of two synthetic oligonucleotide primers, which are complementary to nucleotide sequences in the substrate DNA which are separated by a short distance of a few hundred to a few thousand base pairs, and the use of a thermostable DNA polymerase. The chain reaction consists of a series of 10 to 40 cycles. In each cycle, the substrate DNA is first denatured at high temperature. After cooling down, synthetic primers which are present in vast excess, hybridize to the substrate DNA to form double-stranded structures along complementary nucleotide sequences. The primer-substrate DNA complexes will then serve as initiation sites for a DNA synthesis reaction catalyzed by a DNA polymerase, resulting in the synthesis of a new DNA strand complementary to the substrate DNA strand. The synthesis process is repeated with each additional cycle, creating an amplified product of the substrate DNA.

"Primer," as used herein, refers to an oligonucleotide capable of acting as a point of initiation for DNA synthesis under suitable conditions. Suitable conditions include those in which hybridization of the oligonucleotide to a template nucleic acid occurs, and synthesis or amplification of the target sequence occurs, in the presence of four different nucleoside triphosphates and an agent for extension (e.g., a DNA polymerase) in an appropriate buffer and at a suitable temperature.

"Probe" and "fluorescent generation probe" are synonymous and refer to either a) a sequence-specific oligonucleotide having an attached fluorophore and/or a quencher, and optionally a minor groove binder or b) a DNA binding reagent, such as, but not limited to, SYBR® Green dye.

"Quencher" refers to a molecule or part of a compound, which is capable of reducing the emission from a fluorescent donor when attached to or in proximity to the donor. Quenching may occur by any of several mechanisms including fluorescence resonance energy transfer, photo-induced electron transfer, paramagnetic enhancement of intersystem crossing, Dexter exchange coupling, and exciton coupling such as the formation of dark complexes.

The term "RNase H PCR (rhPCR)" refers to a PCR reaction which utilizes "blocked" oligonucleotide primers and an RNase H enzyme. "Blocked" primers contain at least one chemical moiety (such as, but not limited to, a ribonucleic acid residue) bound to the primer or other oligonucleotide, such that hybridization of the blocked primer to the template nucleic acid occurs, without amplification of the nucleic acid by the DNA polymerase. Once the blocked primer hybridizes to the template or target nucleic acid, the chemical moiety is removed by cleavage by an RNase H enzyme, which is activated at a high temperature (e.g., 50° C. or greater). Following RNase H cleavage, amplification of the target DNA can occur.

The term "discrimination domain" can be the same or different as the cleavage domain. The discrimination domain is the position of the potential mutation site, and the enzyme will only cleave at the cleavage site if the criteria at the discrimination domain are met. For example, in one embodiment RNase H2 will cleave or not cleave a double-stranded target at the RNA residue (cleavage domain), depending on whether a mutation exists at the discrimination domain.

In one embodiment, the 3' end of a blocked primer can comprise the moiety rDDDDMx, wherein relative to the target nucleic acid sequence, "r" is an RNA residue, "D" is a complementary DNA residue, "M" is a mismatched DNA residue, and "x" is a C3 spacer. A C3 spacer is a short 3-carbon chain attached to the terminal 3' hydroxyl group of the oligonucleotide, which further inhibits the DNA polymerase from binding before cleavage of the RNA residue.

The methods described herein can be performed using any suitable RNase H enzyme that is derived or obtained from any organism. Typically, RNase H-dependent PCR reactions are performed using an RNase H enzyme obtained or derived from the hyperthermophilic archaeon *Pyrococcus abyssi* (P.a.), such as RNase H2. Thus, in one embodiment, the RNase H enzyme employed in the methods described herein desirably is obtained or derived from *Pyrococcus abyssi*, preferably an RNase H2 obtained or derived from *Pyrococcus abyssi*. In other embodiments, the RNase H enzyme employed in the methods described herein can be obtained or derived from other species, for example, *Pyrococcus furiosis*, *Pyrococcus horikoshii*, *Thermococcus kodakarensis*, or *Thermococcus litoralis*.

The following examples further illustrate the invention but should not be construed as in any way limiting its scope.

EXAMPLE 1

This example demonstrates an enhanced rhPCR assay that utilizes a highly discriminatory DNA polymerase and RNase H2 for discrimination To demonstrate the utility of these new assay designs, rhPrimers and standard allele-specific primers were designed against rs113488022, the V600E mutation in the human BRAF gene. These primers were tested in PCR and rhPCR with WT or H784Q mutant Taq polymerase. Primers utilized in these assays were as shown in Table 1 (SEQ ID NOs: 1-7).

10 µL reaction volumes were used in these assays. To perform the reaction, 5 µL of 2× Integrated DNA Technologies (IDT) (Coralville, Iowa) rhPCR genotyping master mix (containing dNTPs, H784Q mutant or WT Taq DNA polymerase, stabilizers, and $MgCl_2$) was combined with 200 nM (2 pmol) of either of the allelic primers. 200 nM (2 pmol) of the probe, as well as 200 nM (5 pmol) of the reverse primer were also added. Additionally, 2.5 mU (5.25 fmol/0.53 nM) of P.a. RNase H2 and 1000 copies of synthetic gBlock™ (Integrated DNA Technologies, Coralville, Iowa) template (1000 copies Allele 1, 500 copies allele 1+500 copies allele 2 (heterozygote), or 1000 copies Allele 2 (for gBlock™ sequences, see Table 2, SEQ ID NOs: 8-9) were added to the reaction mix. The reaction was thermocycled on a Bio-Rad™ CFX384™ Real-time system. Cycling conditions were as follows: 953:00–(950:10–650:30)×65 cycles. Each reaction was performed in triplicate.

TABLE 2

Synthetic gBlock templates for Example 1 assay

| Name | Sequence | SEQ ID NO. |
|---|---|---|
| rs113488022 gBlock Template 1 | AAAAAATAAGAACACTGATTTTTGTGAAT ACTGGGAACTATGAAAATACTATAGTTGA GACCTTCAATGACTTTCTAGTAACTCAGCA GCATCTCAGGGCCAAAAATTTAATCAGTG GAAAAATAGCCTCAATTCTTACCATCCAC AAAATGGATCCAGACAACTGTTCAAACTG ATGGGACCCACTCCATCGAGATTTC<u>A</u>CTGT | SEQ ID NO. 8 |

TABLE 1

Sequence of oligonucleotides employed in SNP discrimination assay described in Example 1.

| Name | Sequence | SEQ ID NO. |
|---|---|---|
| Forward non-discriminating primer | GCTGTGATTTTGGTCTAGCTACAG | SEQ ID NO. 1 |
| Forward Allele 1 ASP1 ASPCR primer | GCTGTGATTTTGGTCTAGCTACAG<u>T</u> | SEQ ID NO. 2 |
| Forward Allele 2 ASP2 ASPCR primer | GCTGTGATTTTGGTCTAGCTACAG<u>A</u> | SEQ ID NO. 3 |
| Probe | FAM-TCCCATCAG-ZEN-TTTGAACAGTTGTCTGGA-IBFQ | SEQ ID NO. 4 |
| rs113488022 Allele 1 Forward ASP1 rhPrimer | GCTGTGATTTTGGTCTAGCTACAG<u>T</u>gAA ATG-x | SEQ ID NO. 5 |
| rs113488022 Allele 2 Forward ASP2 rhPrimer | GCTGTGATTTTGGTCTAGCTACAG<u>A</u>gAA ATG-x | SEQ ID NO. 6 |
| Reverse rhPrimer | GCCCTCAATTCTTACCATCCACAAAaTG GAA-x | SEQ ID NO. 7 |

Nucleic acid sequences are shown 5'-3'. DNA is uppercase, RNA is lowercase.
Location of potential mismatch is underlined.
ZEN = internal ZEN ™ quencher (IDT, Coralville, IA),
FAM = 6-carboxyfluorescein,
IBFQ = Iowa Black ® FQ (fluorescence quencher, IDT, Coralville, IA), and x = C3 propanediol spacer block TABLE 2-continued Synthetic gBlock templates for Example 1 assay

| Name | Sequence | SEQ ID NO. |
|---|---|---|
| | AGCTAGACCAAAATCACCTATTTTTACTGT | |
| | GAGGTCTTCATGAAGAAATATATCTGAGG | |
| | TGTAGTAAGTAAAGGAAAACAGTAGATCT | |
| | CATTTTCCTATCAGAGCAAGCATTATGAAG | |
| | AGTTTAGGTAAGAGATCTAATTTCTATAAT | |
| | TCTGTAATATAATATTCTTTAAAACATAGT | |
| | ACTTCATCTTTCCTCTTA | |
| rs113488022 gBlock Template 2 | AAAAAATAAGAACACTGATTTTTGTGAAT ACTGGGAACTATGAAAATACTATAGTTGA GACCTTCAATGACTTTCTAGTAACTCAGCA GCATCTCAGGGCCAAAAATTTAATCAGTG GAAAAATAGCCTCAATTCTTACCATCCAC AAAATGGATCCAGACAACTGTTCAAACTG ATGGGACCCACTCCATCGAGATTTCTCTGT AGCTAGACCAAAATCACCTATTTTTACTGT GAGGTCTTCATGAAGAAATATATCTGAGG TGTAGTAAGTAAAGGAAAACAGTAGATCT CATTTTCCTATCAGAGCAAGCATTATGAAG AGTTTAGGTAAGAGATCTAATTTCTATAAT TCTGTAATATAATATTCTTTAAAACATAGT ACTTCATCTTTCCTCTTA | SEQ ID NO. 9 |

Nucleic acid sequences are shown 5'-3'. Location of SNPs are shown bold and underlined.

Cq Results of the experiment are shown in Table 3. This data shows that the mismatch discrimination of the assay system increases with rhPCR over ASPCR with WT Taq polymerase, and that the discrimination is enhanced by the use of the H784Q Taq polymerase.

TABLE 3

Resulting Cq values

| | WT Taq | | | | H784Q | | | |
|---|---|---|---|---|---|---|---|---|
| | Allele 1 | Het | Allele 2 | NTC | Allele 1 | Het | Allele 2 | NTC |
| Non discrmin | 29.3 | 29.3 | 29.4 | >65 | 30.6 | 30.6 | 30.8 | >65 |
| ASP1 ASPCR | 30.2 | 30.2 | 31.4 | >65 | 29.2 | 32.5 | 40.3 | >65 |
| ASP2 ASPCR | 36.7 | 30.5 | 29.4 | >65 | 44.2 | 31.7 | 30.8 | >65 |
| ASP1 rhPCR | 30.9 | 32.1 | 38.2 | >65 | 31.9 | 31.4 | 49.2 | >65 |
| ASP2 rhPCR | 39.3 | 31.0 | 30.8 | >65 | 43.4 | 33.9 | 32.5 | >65 |

All numbers in this table represent Cq values obtained from the CFX384™ instrument (Bio-Rad™, Hercules, CA).

EXAMPLE 2

The following example demonstrates an enhanced rhPCR assay that utilizes a highly discriminatory DNA polymerase and RNase H2 for discrimination.

In order to demonstrate that this new assay design could function, rhPrimers and standard allele-specific primers were designed against rs113488022, the V600E mutation in the human BRAF gene. These primers were tested in PCR and rhPCR with H784Q mutant Taq polymerase. Primers utilized in these assays were as shown in Table 4 (SEQ ID NOs: 1, 4 and 10-12).

TABLE 4

Sequence of oligonucleotides employed in SNP discrimination assay described in Example 2

| Name | Sequence | SEQ ID NO. |
|---|---|---|
| Forward non-discrimin primer | GCTGTGATTTTGGTCTAGCTACAG | SEQ ID NO. 1 |
| Probe | FAM-TCCCATCAG-ZEN-TTTGAACAGTTGTCTGGA-IBFQ | SEQ ID NO. 4 |
| rs113488022 Allele 1 Forward dxxd rhPrimer | GCTGTGATTTTGGTCTAGCTACAGT<u>g</u> AxxTG | SEQ ID NO. 10 |
| rs113488022 Allele 2 Forward dxxd rhPrimer | GCTGTGATTTTGGTCTAGCTACAG<u>A</u>g AxxTG | SEQ ID NO. 11 |
| Reverse rhPrimer | GCCCTCAATTCTTACCATCCACAAAa TGGAA-x | SEQ ID NO. 12 |

Nucleic acid sequences are shown 5'-3'. DNA is uppercase, RNA is lowercase. Location of potential mismatch is underlined.
ZEN = internal Zen ® fluorescent quencher (IDT, Coralville, IA).
FAM = 6-carboxyfluorescein,
IBFQ = Iowa Black FQ (fluorescence quencher), and x = C3 propanediol spacer.

10 μL reaction volumes were used in these assays. To perform the reaction, 5 μL of 2× Integrated DNA Technologies (IDT) (Coralville, Iowa) rhPCR genotyping master mix (containing dNTPs, H784Q mutant DNA polymerase, stabilizers, and $MgCl_2$) was combined with 200 nM (2 pmol) of either of the allelic primers. 200 nM (2 pmol) of the probe, as well as 200 nM (5 pmol) of the reverse primer were also added. Additionally, 7.5 mU (15.75 fmol/1.58 nM), 50 mU (105 fmol/10.5 nM) or 200 mU (420 fmol/42 nM) of P.a. RNase H2 and 5e4 copies of synthetic gBlock™ (Integrated DNA Technologies, Coralville, Iowa) template (1e5 copies Allele 1, 5e4 copies allele 1+5e4 copies allele 2 (heterozygote), or 1e5 copies Allele 2 (for gBlock™ sequences, see Table 2, SEQ ID NOs: 8-9) were added to the reaction mix. The reaction was thermocycled on a Bio-Rad™ CFX384™ Real-time system. Cycling conditions were as follows: $95^{3:00}$–$(95^{0:10}$–$65^{0:30})$×65 cycles. Each reaction was performed in triplicate.

Cq Results of the experiment are shown in Table 5. This data shows that the mismatch discrimination of the assay system increases with rhPCR over ASPCR with WT Taq polymerase, and that the discrimination is enhanced by the use of the H784Q Taq polymerase.

TABLE 5

Resulting Cq values

| Averages | | Allele 1 | Het | Allele 2 | NTC | ΔCq |
|---|---|---|---|---|---|---|
| Unblocked | 7.5 mU | 21.9 | 22.3 | 22.1 | >75 | |
| | 50 mU | 22.7 | 22.5 | 22.7 | >75 | |
| | 200 mU | 21.8 | 21.8 | 21.9 | >75 | |
| AgAxxTG | 7.5 mU | 43.7 | 25.6 | 24.6 | >75 | 19.1 |
| | 50 mU | 50.3 | 24.5 | 23.5 | >75 | 26.8 |
| | 200 mU | 48.5 | 25.2 | 24.1 | >75 | 24.4 |
| TgAxxTG | 7.5 mU | 25.1 | 26.3 | 42.5 | >75 | 17.4 |
| | 50 mU | 24.2 | 25.4 | 41.0 | >75 | 16.9 |
| | 200 mU | 22.9 | 23.8 | 37.2 | >75 | 14.3 |

All numbers in this table represent Cq values obtained from the CFX384™ instrument (Bio-Rad™, Hercules, CA).

The delta Cq values were significantly higher than the ones obtained with the Gen 1 versions of these primers, indicating that there is an advantage to this primer design, as seen before in rhPCR.

EXAMPLE 3

The following example illustrates the heightened reliability of universal assays using a DNA polymerase with a high mismatch discrimination.

To demonstrate that the disclosed assays can function in a universal format and that they are significantly improved with a polymerase with high mismatch discrimination, "universal" assay primers were designed against rs351855, the G338R mutation in the human FGFR4 gene. This "universal" assay design has numerous advantages, including the ability to multiplex the allele-specific rhPrimers and obtain multiple-color readouts. Primers utilized in this assay were as shown in Table 6 (SEQ ID NOs: 13-18).

TABLE 6

Sequences of oligonucleotides employed in "universal" SNP discrimination assay

| Name | Sequence | SEQ ID NO. |
|---|---|---|
| Universal Forward primer | CGCCGCGTATAGTCCCGCGTAAA | SEQ ID NO. 13 |
| Probe 1 (FAM) | FAM-C+CATC+A+C+CGTG+CT-IBFQ | SEQ ID NO. 14 |
| Probe 2 (HEX) | HEX-CAATC+C+C+CGAG+CT-IBFQ | SEQ ID NO. 15 |
| rs351855 Allele 1 Forward primer | GCCCATGTCCCAGCGAACCATCACCGTGCTA GCCCTCGATACAGCCCgGCCAC-x | SEQ ID NO. 16 |
| rs351855 Allele 2 Forward primer | GCCCATGTCCCAGCGAACAATCCCCGAGCTG CCCTCGATACAGCCTgGCCAC-x | SEQ ID NO. 17 |
| Reverse primer | GCGGCCAGGTATACGGACATcATCCA-x | SEQ ID NO. 18 |

Nucleic acid sequences are shown 5'-3'. DNA is uppercase, RNA is lowercase. Location of potential mismatch is underlined. LNA residues are designated with a +. FAM = 6-carboxyfluorescein,
HEX = 6-carboxy-2',4,4',5',7,7'-hexachlorofluorescein,
IBFQ = Iowa Black FQ (fluorescence quencher), and x = C3 propanediol spacer block.

Figure 2A:
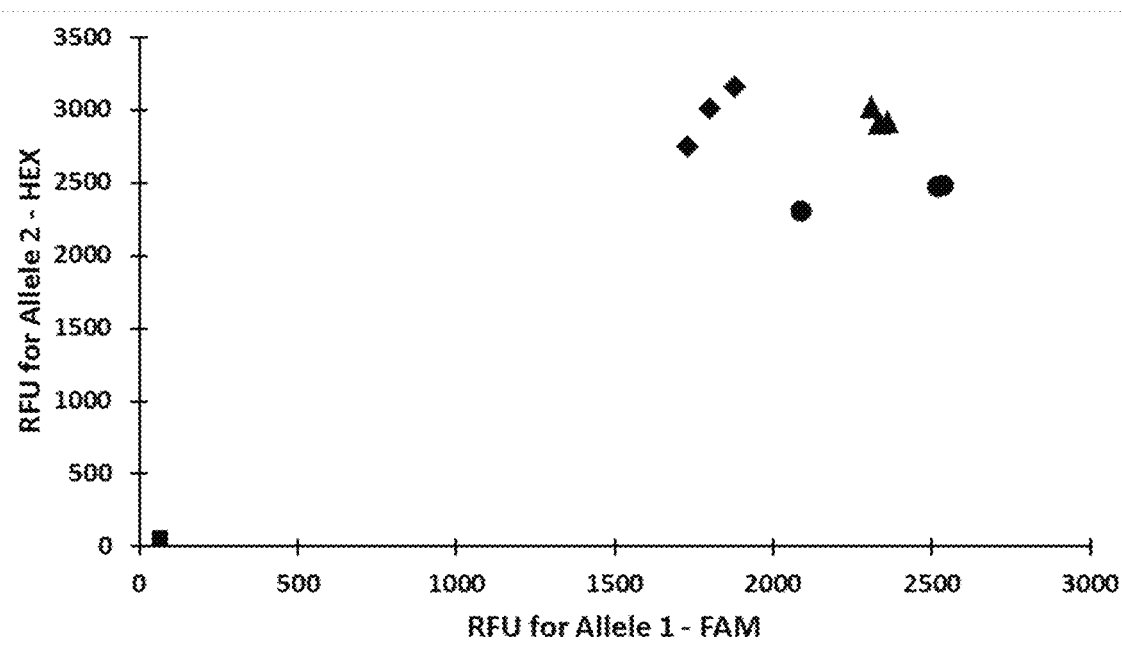
FIGS. 2A and 2B are end-point fluorescence plots from the assay described in Example 1. FAM and HEX fluorescence values are plotted onto the X and Y axis.
Figure 2B:
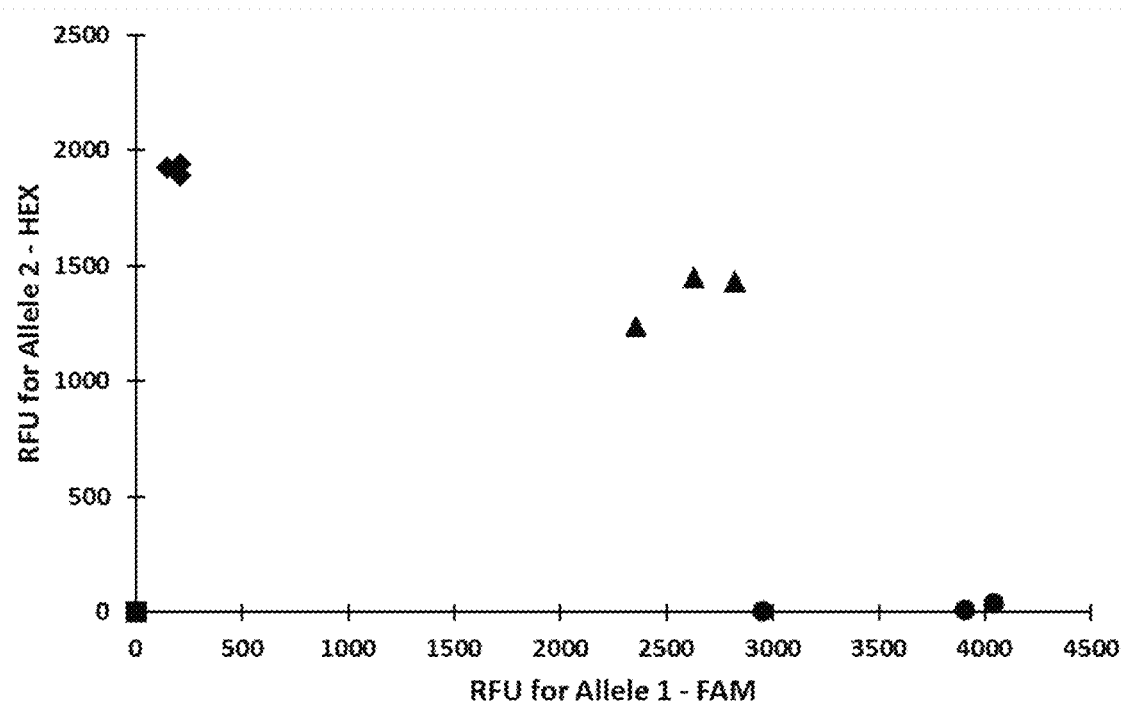

10 μL reaction volumes were used in these assays. To perform the reaction, 5 μL of 2× Integrated DNA Technologies (IDT) (Coralville, Iowa) rhPCR genotyping master mix (containing dNTPs, mutant or WT Taq DNA polymerase, stabilizers, and $MgCl_2$) was combined with 50 nM (500 fmol) of each of the two allelic primers. 250 nM (2.5 pmol) of each of the two probes, as well as 500 nM (5 pmol) of the Universal Forward primer and 500 nM (5 pmol) of the reverse primer were also added. Additionally, 2.5 mU (5.25 fmol/0.53 nM) of P.a. RNase H2 and 1000 copies of synthetic gBlock™ (Integrated DNA Technologies, Coralville, Iowa) template (1000 copies Allele 1, 500 copies allele 1+500 copies allele 2 (heterozygote), or 1000 copies Allele 2 (for gBlock™ sequences, see Table 7, SEQ ID NOs: 19-20) were added to the reaction mix. The reaction was thermocycled on a Bio-Rad™ CFX384™ Real-time system. Cycling conditions were as follows: $95^{3:00}$–($95^{0:10}$–$60^{0:30}$)×3 cycles–($95^{0:10}$–$65^{0:30}$)×65 cycles. Each reaction was performed in triplicate. Fluorescence reads were taken after a total of 50 cycles were completed. Fluorescence values were plotted on the FAM and HEX axis, and results are shown in FIGS. 2a and 2b.

TABLE 7

Synthetic gBlock templates for Example 3

| Name | Sequence | SEQ ID NO. |
|---|---|---|
| rs351855 gBlock Template 1 | GTTGGGAGCTGGGAGGGACTGAGTTAGGG TGCACGGGGCGGCCAGTCTCACCACTGAC CAGTTTGTCTGTCTGTGTGTGTCCATGTGC GAGGGCAGAGGAGGACCCCACATGGACC GCAGCAGCGCCCGAGGCCAGGTATACGGA CATCATCCTGTACGCGTCGGGCTCCCTGGC CTTGGCTGTGCTCCTGCTGCTGGCCGGGCT GTATCGAGGGCAGGCGCTCCACGGCCGGC ACCCCCGCCCGCCCGCCACTGTGCAGAAG CTCTCCCGCTTCCCTCTGGCCCGACAGGTA CTGGGCGCATCCCCCACCTCACATGTGAC AGCCTGACTCCAGCAGGCAGAACCAAGTC TCCCACTTTGCAGTTCTCCCTGGAGTCAGG CTCTTCCGGCAAGTCAAGCT | SEQ ID NO. 19 |
| rs351855 gBlock Template 2 | GTTGGGAGCTGGGAGGGACTGAGTTAGGG TGCACGGGGCGGCCAGTCTCACCACTGAC CAGTTTGTCTGTCTGTGTGTGTCCATGTGC GAGGGCAGAGGAGGACCCCACATGGACC GCAGCAGCGCCCGAGGCCAGGTATACGGA CATCATCCTGTACGCGTCGGGCTCCCTGGC CTTGGCTGTGCTCCTGCTGCTGGCCAGGCT GTATCGAGGGCAGGCGCTCCACGGCCGGC ACCCCCGCCCGCCCGCCACTGTGCAGAAG CTCTCCCGCTTCCCTCTGGCCCGACAGGTA CTGGGCGCATCCCCCACCTCACATGTGAC AGCCTGACTCCAGCAGGCAGAACCAAGTC TCCCACTTTGCAGTTCTCCCTGGAGTCAGG CTCTTCCGGCAAGTCAAGCT | SEQ ID NO. 20 |

Nucleic acid sequences are shown 5'-3'. Location of SNPs are shown bold and underlined.

The results illustrate that the mismatch discrimination between homozygotes is sufficient with both polymerases, although the resulting data using the WT Taq demonstrate that it is more difficult to make an allelic call. Importantly, however, the WT Taq polymerase cannot efficiently discriminate heterozygotes from homozygotes, and places them too close to the allele 1 and 2 signals (FIG. 2a). In contrast, the signal from the heterozygotes in the assays utilizing the mutant Taq polymerase are easily distinguishable from the homozygotes (FIG. 2b).

The importance of the mutant Taq can be further understood when examining the Cq values from this example (Table 8). The data show that not only does the H784Q Taq mutant increase mismatch discrimination dramatically, but the Cqs of the NTCs decrease from the low-to-mid 50s, to greater than the number tested in the assay (>65). From this experiment, it is shown that allele identity can be determined from Cq values as well as end-point fluorescence.

TABLE 8

Cq and delta Cq data for the experiment described in Example 3

| | WT Taq | | | H784Q | | |
|---|---|---|---|---|---|---|
| Template | FAM | HEX | Delta Cq | FAM | HEX | Delta Cq |
| Allele 1 | 32.9 | 31.3 | −1.6 | 37.5 | 56.8 | 19.3 |
| Allele 1 | 31.9 | 31.1 | −0.8 | 36.2 | 51.4 | 15.2 |
| Allele 1 | 31.8 | 31.0 | −0.9 | 36.6 | 54.3 | 17.8 |

TABLE 8-continued

Cq and delta Cq data for the experiment described in Example 3

| | WT Taq | | | H784Q | | |
|---|---|---|---|---|---|---|
| Template | FAM | HEX | Delta Cq | FAM | HEX | Delta Cq |
| Heterozygote | 33.0 | 29.4 | −3.5 | 38.7 | 37.8 | −0.9 |
| Heterozygote | 32.8 | 29.7 | −3.1 | 38.7 | 38.2 | −0.5 |
| Heterozygote | 33.2 | 30.0 | −3.3 | 39.9 | 39.1 | −0.8 |
| Allele 2 | 35.1 | 29.1 | 6.0 | 50.6 | 36.5 | 14.1 |
| Allele 2 | 34.7 | 29.3 | 5.4 | 52.1 | 36.6 | 15.5 |
| Allele 2 | 34.5 | 29.0 | 5.5 | 50.7 | 36.1 | 14.6 |
| NTC | 51.8 | 56.1 | — | >65 | >65 | — |
| NTC | 52.8 | 56.1 | — | >65 | >65 | — |
| NTC | 52.1 | 50.7 | — | >65 | >65 | — |

All numbers in this table represent Cq and delta Cq values values obtained from the CFX384 instrument (Bio-Rad™, Hercules, CA).

EXAMPLE 4

The following example illustrates the detection of rare allelic variants with the assay designs of the present invention. To demonstrate the utility of these new assay designs to detect rare allelic variants, previously described second generation rhPrimers (rdxxdm) were utilized against rs113488022, the V600E mutation in the human BRAF gene (see Table 4; SEQ ID NOs: 1, 4 and 10-12).

10 μL reaction volumes were used in these assays. To perform the reaction, 5 μL of 2× Integrated DNA Technologies (IDT) (Coralville, Iowa) rhPCR genotyping master mix (containing dNTPs, H784Q mutant or WT Taq DNA polymerase, stabilizers, and MgCl$_2$) was combined with 200 nM (2 pmol) of either of the allelic primers, or the non-discriminatory forward primer. 200 nM (2 pmol) of the probe, as well as 200 nM (5 pmol) of the reverse primer were also added. Additionally, 50 mU (105 fmol/10.5 nM) of P.a. RNase H2 and 50,000 copies of synthetic gBlock™ (Integrated DNA Technologies, Coralville, Iowa) match template, was combined with either 0, 50, or 500 copies of the opposite allele (for gBlock™ sequences, see Table 6, SEQ ID NOs: 16-17) were added to the reaction mix. The reaction was thermocycled on a Bio-Rad™ CFX384™ Real-time system. Cycling conditions were as follows: $95^{3:00}$–$(95^{0:10}$–$60^{0:30})$×65 cycles. Each reaction was performed in triplicate.

Data for the WT polymerase is shown in Table 9, and for the H784Q mutant Taq polymerase in Table 10. One of the advantages of this system for rare allele detection over "conventional" rhPCR is the ability to utilize a single amount of RNase H2 for both alleles. This advantage halves the potential requirement for determining the enzyme amount required for cleavage.

TABLE 9

Average Cq and delta Cq values for the rare allele experiment with the WT Taq polymerase described in Example 4.

| | | Back-ground | | | | | |
|---|---|---|---|---|---|---|---|
| | | 50,000 | 50,000 | 50,000 | 0 | 0 | 0 |
| | | | | Target | | | |
| | | 500 | 50 | 0 | 500 | 50 | 0 |
| SEQ ID No. 1 | Non-discrimin | 22.9 | 23.1 | 22.8 | 30.4 | 34.2 | >65 |
| SEQ ID NO. 10 | ... TgAxxTG | 31.6 | 34.5 | 36.1 | 31.6 | 36.0 | >65 |
| SEQ ID NO. 11 | ... AgAxxTG | 29.1 | 29.1 | 29.9 | 30.8 | 34.4 | >65 |

All numbers in this table represent Cq and delta Cq values values obtained from the CFX384 instrument (Bio-Rad™, Hercules, CA).
DNA is uppercase, RNA is lowercase. Location of potential mismatch is underlined.
x = internal C3 propanediol spacer block.

TABLE 10

Average Cq and delta Cq values for the rare allele experiment with the H784Q mutant Taq polymerase described in Example 4.

| | | Back-ground | | | | | |
|---|---|---|---|---|---|---|---|
| | | 50,000 | 50,000 | 50,000 | 0 | 0 | 0 |
| | | | | Target | | | |
| | | 500 | 50 | 0 | 500 | 50 | 0 |
| SEQ ID No. 1 | Non-discrimin | 22.7 | 23.2 | 23.2 | 31.5 | 34.2 | >65 |
| SEQ ID NO. 10 | ... TgAxxTG | 33.8 | 36.6 | 47.3 | 33.1 | 36.4 | >65 |
| SEQ ID NO. 11 | ... AgAxxTG | 32.1 | 35.2 | 38.8 | 32.0 | 35.5 | >65 |

All numbers in this table represent Cq and delta Cq values obtained from the CFX384 instrument (Bio-Rad ™, Hercules, CA).
DNA is uppercase, RNA is lowercase. Location of potential mismatch is underlined.
x = internal C3 propanediol spacer block.

The data clearly shows that the H784Q DNA polymerase allows for detection of 50 copies of target in a 50,000 copies of background DNA (a 1:1000 discrimination level) for the mutant A allele of rs113488022, with a delta Cq of over 11 cycles. While only slightly more than 3 cycles was observed for the T allele in this assay, this was a significant improvement over the WT Taq polymerase, which did not show any discrimination for the T allele, and only a delta of 3 cycles for the A allele.

EXAMPLE 5

This example demonstrates successful allelic discrimination with the use of a universal rhPCR genotyping assay and Integrated DNA Technologies (IDT) (Coralville, Iowa) rhPCR genotyping master mix, and the robust stability of the reaction components. To demonstrate the robust nature of the assay design and mixture components, universal primers were designed against rs4657751, a SNP located on the human Chromosome 1 (See Table 11, SEQ ID NOs: 14, 21-25).

Identical universal rhPCR genotyping reactions were set up in two white Hard-Shell® 384-well skirted PCR plates (Bio-Rad, Hercules, Calif.) on the Bio-Rad CFX384 Touch™ Real-Time PCR Detection System with 10 µL final volume. Each well contained the rhPCR assay primers (150 nM of rs4657751 Allele Specific Primer 1 (SEQ ID NO: 23), 150 nM of rs4657751 Allele Specific Primer 2 (SEQ ID NO: 24), and 500 nM rs4657751 Locus Specific Primer (SEQ ID NO: 25). Reactions contained universal reporter oligos at the following concentrations: 250 nM of universal FAM probe (SEQ ID NO: 14), 450 nM of universal Yakima Yellow® (SEQ ID NO: 22) probe, and 1000 nM of universal forward primer (SEQ ID NO: 21), and 5 µL of 2× Integrated DNA Technologies (IDT) (Coralville, Iowa) rhPCR genotyping master mix (containing dNTPs, a mutant H784Q Taq polymerase (see Behlke, et al. U.S. 2015/0191707), chemically modified *Pyrococcus abyssi* RNase H2 (See Walder et al. UA20130288245A1), stabilizers, and MgCl$_2$).

gBlocks® Gene Fragments (Integrated DNA Technologies, Inc., Coralville, Iowa) containing either allele of the rs4657751 SNP were utilized as the source of template DNA (See Table 12, SEQ ID NOs: 26 and 27). Each well contained template representing one of three possible genotypes: allele 1 homozygote (1000 copies rs4657751 Allele 1 gBlock® template (SEQ ID NO: 26)), allele 2 homozygote (1000 copies rs4657751 Allele 2 gBlock® template (SEQ ID NO: 27)), or heterozygote (mix of 500 copies of rs4657751 Allele 1 gBlock® template (SEQ ID NO: 26) and 500 copies of rs4657751 Allele 2 gBlock® template (SEQ ID NO: 27)). Template or water for the no template control (NTC) reactions were added into three replicate wells of two individual plates. The reactions underwent the following cycling protocol: 95° C. for 10 minutes, then 45 cycles of 95° C. for 10 seconds and 60° C. for 45 seconds.

TABLE 11

Sequences of oligonucleotides used in Example 5

| Name | Sequence | SEQ ID NO. |
|---|---|---|
| Universal Forward primer | CGGCCCATGTCCCAGCGAA | SEQ ID NO. 21 |
| Probe 1 (FAM) | FAM-C+CATC+A+C+CGTG+CT-IBFQ | SEQ ID NO. 14 |
| Probe 2 (Yakima Yellow) | Yak-CAATC+C+C+CGAG+CT-IBFQ | SEQ ID NO. 22 |
| rs4657751 Allele 1 Forward primer | GCCCATGTCCCAGCGAACCATCACCGTGC TACTTCCCACACCCTCATATCuTGTTA-x | SEQ ID NO. 23 |
| rs4657751 Allele 2 Forward primer | GCCCATGTCCCAGCGAACAATCCCCGAGC TCTTACTTCCCACACCCTCATATAuTGTTA-x | SEQ ID NO. 24 |
| rs4657751 Reverse primer | GCGCTAAGTAAACATTCCTGATTGCAaCTT AT-x | SEQ ID NO. 25 |

Nucleic acid sequences are shown 5'-3'.
DNA is uppercase, RNA is lowercase.
Location of potential mismatch is underlined.
LNA residues are designated with a +.
FAM = 6-carboxyfluorescein,
Yak = Yakima Yellow (3-(5,6,4',7'-tetrachloro-5'-methyl-3',6'-dipivaloylfluorescein-2-yl)),
IBFQ = Iowa Black FQ (fluorescence quencher), and
x = C3 propanediol spacer block.

TABLE 12

Synthetic gBlock® templates used in Example 5.

| Name | Sequence | SEQ ID NO. |
|---|---|---|
| rs4657751 Allele 1 gBlock template | GATTTTTTTTTTTGGCATTTCTTCTTAGAT TTCTATCTCCTAACATAGGATCACTTATTT GTGAAATTATTTGTATACCTTTTTTATGGA GTGATGATGTGATACAAATTCTATCCTTAA GGATATAAGAACATCTTTTCTTTATATTAG GATTTTTCTGGACCCATGAGTTACATGCTT ACTTCCCACACCCTCATAT<u>C</u>TTGTTTAAAT TTGTAGAATTAAATTCATAGGTAATTATTT CTGAAACTTCTTCCCTGTGTGAGCAATCTA AATAATTATTACAATGCCTTAAGTTGCAAT CAGGAATGTTTACTTAGCACAGACTTTTTT CCCCACTACTGCACTCAAAGGATAACAGA TATATGGCAAATCTAACCATATTCTTTGTC CTTTGTCCATGTTGCGGAGGGAAGCTCATC AGTGGGGCCACGAGCTGAGTGCGTCCTGT CACTCCACTCCCATGTCCCTTGGGAAGGTC TGAGACTAGGG | SEQ ID NO. 26 |
| rs4657751 Allele 2 gBlock template | GATTTTTTTTTTTGGCATTTCTTCTTAGAT TTCTATCTCCTAACATAGGATCACTTATTT GTGAAATTATTTGTATACCTTTTTTATGGA GTGATGATGTGATACAAATTCTATCCTTAA GGATATAAGAACATCTTTTCTTTATATTAG GATTTTTCTGGACCCATGAGTTACATGCTT ACTTCCCACACCCTCATAT<u>A</u>TTGTTTAAAT TTGTAGAATTAAATTCATAGGTAATTATTT CTGAAACTTCTTCCCTGTGTGAGCAATCTA AATAATTATTACAATGCCTTAAGTTGCAAT CAGGAATGTTTACTTAGCACAGACTTTTTT CCCCACTACTGCACTCAAAGGATAACAGA TATATGGCAAATCTAACCATATTCTTTGTC CTTTGTCCATGTTGCGGAGGGAAGCTCATC AGTGGGGCCACGAGCTGAGTGCGTCCTGT CACTCCACTCCCATGTCCCTTGGGAAGGTC TGAGACTAGGG | SEQ ID NO. 27 |

Nucleic acid sequences are shown 5'-3'.
DNA is uppercase. The location of the SNP is underlined.

Figure 3A:
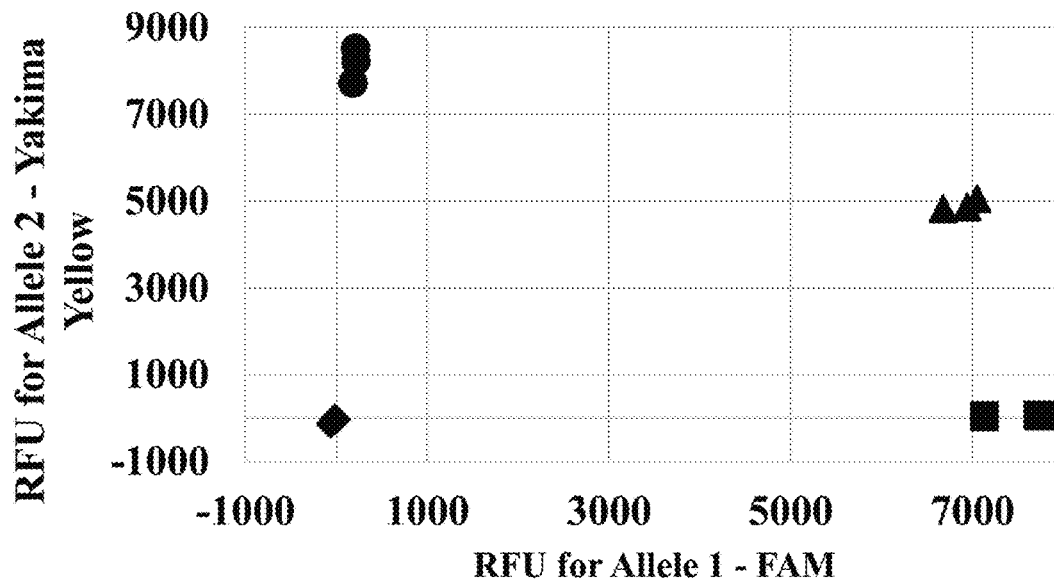
FIGS. 3A and 3B are allelic discrimination plots with genotyping calls for rs4655751. The reaction plate was cycled immediately after reaction setup (A) or held at room temperature on the benchtop for 48 hours prior to cycling (B). Diamonds: no template controls (NTCs); squares: allele 1 samples; circles: allele 2 samples; triangles: heterozygotes. Genotypes are tightly clustered and have good angle separation, indicating excellent allelic specificity. Each sample was assigned the correct genotyping call, and no change in performance was observed over the 48 hour hold period.
Figure 3B:
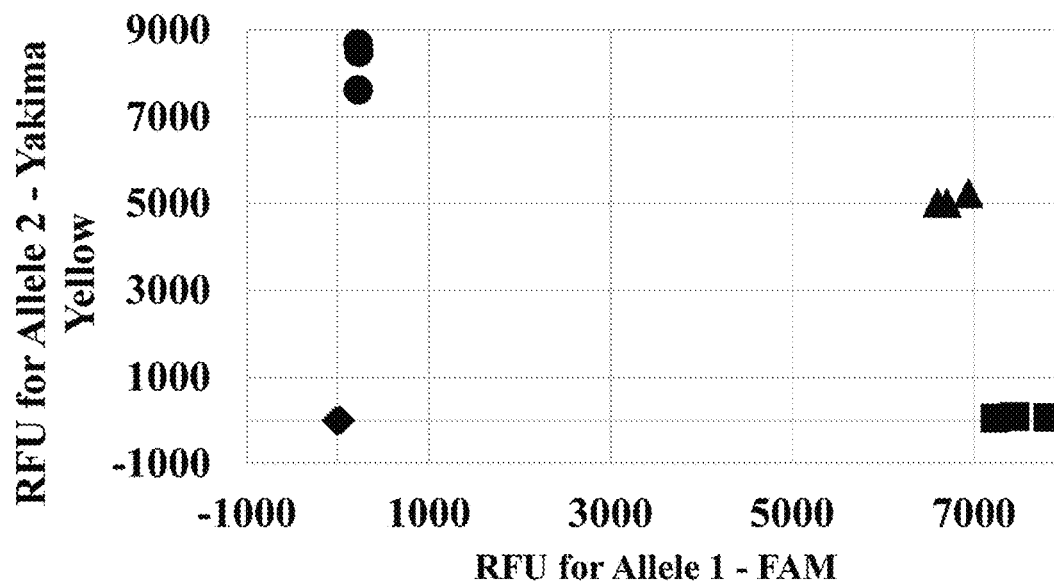

One reaction plate was cycled immediately (0 hr benchtop hold) and one reaction plate was held at room temperature for 2 days (48 hr benchtop hold) to demonstrate reaction stability over time. Allelic discrimination analysis was performed using Bio-Rad CFX Manager 3.1 software (Bio-Rad, Hercules, Calif.). FAM and Yakima Yellow fluorophores were detected in each well. For both fluorophores the baseline cycles were set to begin at cycle 10 and end at cycle 25. Fluorescence signal (RFU) in each well at the end of 45 cycles was used to generate an allelic discrimination plot and genotypes were determined with auto-call features of the analysis software. Identical performance was obtained with the immediate run (FIG. 3A) and 48 hour hold plate (FIG. 3B), demonstrating robust stability of the reaction components. Each sample is assigned the correct genotyping call and samples of the same genotype are tightly clustered together. The heterozygote cluster is separated from both of the homozygous clusters by an approximate 45 degree angle, indicating excellent allelic specificity of the universal rhPCR genotyping assays and master mix.

EXAMPLE 6

The following example compares the performance of the genotyping methods of the present invention versus traditional 5' nuclease genotyping assay methods (Taqman™).

The rs1799865 SNP in the CCR2 gene was selected, and rhPCR genotyping primers as well as an rs1799865 5' nuclease assay (Thermo-Fisher (Waltham, Mass.)), were designed and obtained. Sequences for the rs1799865 rhPCR genomic SNP assay are shown in Table 14 (SEQ ID NOs: 14, 21, 22, and 28-30). Thermo-Fisher 5' nuclease primer/probe (Taqman™) sequences are not published, and therefore are not included in this document.

Reactions were performed in 10 µL volumes, containing 10 ng Coriell genomic DNA (Camden, N.J.), 250 nM of universal FAM probe (SEQ ID NO: 14), 450 nM of universal Yakima Yellow® (SEQ ID NO: 22) probe, 1000 nM of universal forward primer (SEQ ID NO: 21), 150 nM of the two allele-specific forward primers (SEQ ID NOs: 28 and 29), 500 nM of the reverse primer (SEQ ID NO: 30), and 5 µL of 2× Integrated DNA Technologies (IDT) (Coralville, Iowa) rhPCR genotyping master mix (containing dNTPs, a mutant H784Q Taq polymerase (see Behlke, et al. U.S. 2015/0191707), chemically modified *Pyrococcus abyssi* RNase H2 (See Walder et al. UA20130288245A1), stabilizers, and $MgCl_2$).

PCR was performed on Life Technologies (Carlsbad, Calif.) QuantStudio™ 7 Flex real-time PCR instrument using the following cycling conditions: 10 mins at 95° C. followed by 50 cycles of 95° C. for 10 seconds and 60° C. for 45 seconds. End-point analysis of each of the plates was performed after 45 cycles with the QuantStudio™ Real-Time PCR Software v1.3 (Carlsbad, Calif.).

TABLE 14

Sequences of oligonucleotides used for the rs1799865 genotyping assay in Example 6.

| Name | Sequence | SEQ ID NO. |
|---|---|---|
| Universal Forward primer | CGGCCCATGTCCCAGCGAA | SEQ ID NO. 21 |
| Probe 1 (FAM) | FAM-C+CATC+A+C+CGTG+CT-IBFQ | SEQ ID NO. 14 |
| Probe 2 (Yakima Yellow) | Yak-CAATC+C+C+CGAG+CT-IBFQ | SEQ ID NO. 22 |
| rs1799865 Allele 1 Forward primer | GCCCATGTCCCAGCGAACCATCACCGTG CTTTCTCTTCTGGACTCCCTATAATaTTGT G-x | SEQ ID NO. 28 |
| rs1799865 Allele 2 Forward primer | GCCCATGTCCCAGCGAACAATCCCCGAG CTTTCTCTTCTGGACTCCCTATAACaTTGT G-x | SEQ ID NO. 29 |

TABLE 14-continued

Sequences of oligonucleotides used for the rs1799865 genotyping assay in Example 6.

| Name | Sequence | SEQ ID NO. |
|---|---|---|
| rs1799865 Reverse primer | GCGGATTGATGCAGCAGTGAgTCATG-x | SEQ ID NO. 30 |

Nucleic acid sequences are shown 5'-3'.
DNA is uppercase, RNA is lowercase.
LNA residues are designated with a +.
Location of potential mismatch is underlined.
FAM = 6-carboxyfluorescein,
Yak = Yakima Yellow (3-(5,6,4',7'-tetrachloro-5'-methyl-3',6'-dipivaloylfluorescein-2-yl)),
IBFQ = Iowa Black FQ (fluorescence quencher),
and x = C3 propanediol spacer block.

Figure 4A:
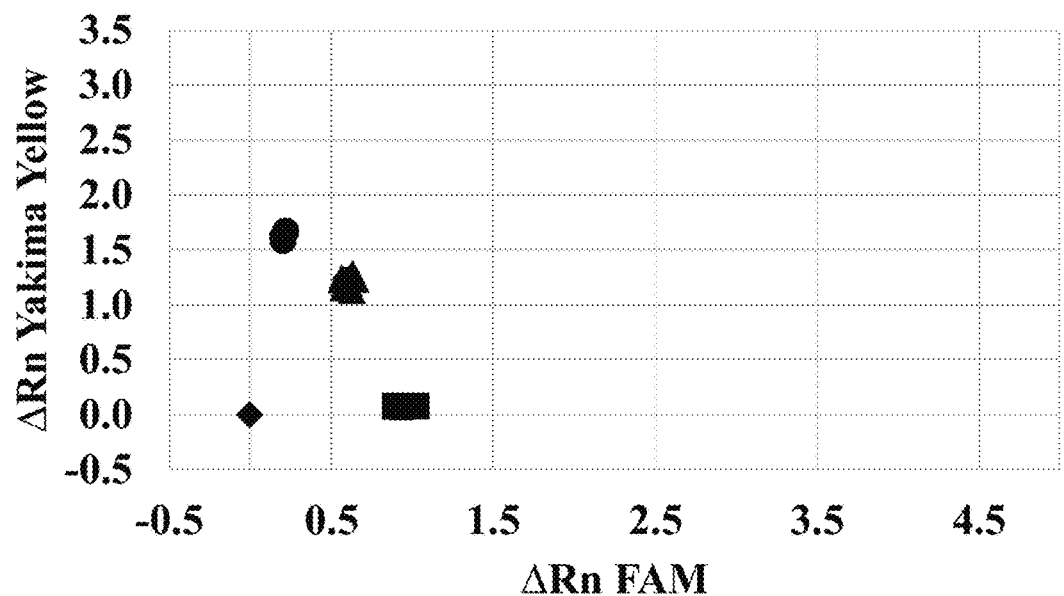
FIGS. 4A and 4B illustrate a side-by-side comparison of Allelic Discrimination Plots of gene CCR2, rs1799865 from a TaqMan based assay versus rhPCR. Diamonds: no template controls (NTCs); squares: allele 1 samples; circles: allele 2 samples; triangles: heterozygotes. The rhPCR Genotyping Assay (FIG. 4B) achieved higher fluorescence signal compared to a traditional 5'-nuclease genotyping assay (FIG. 4A) while showing concordant results.
Figure 4B:
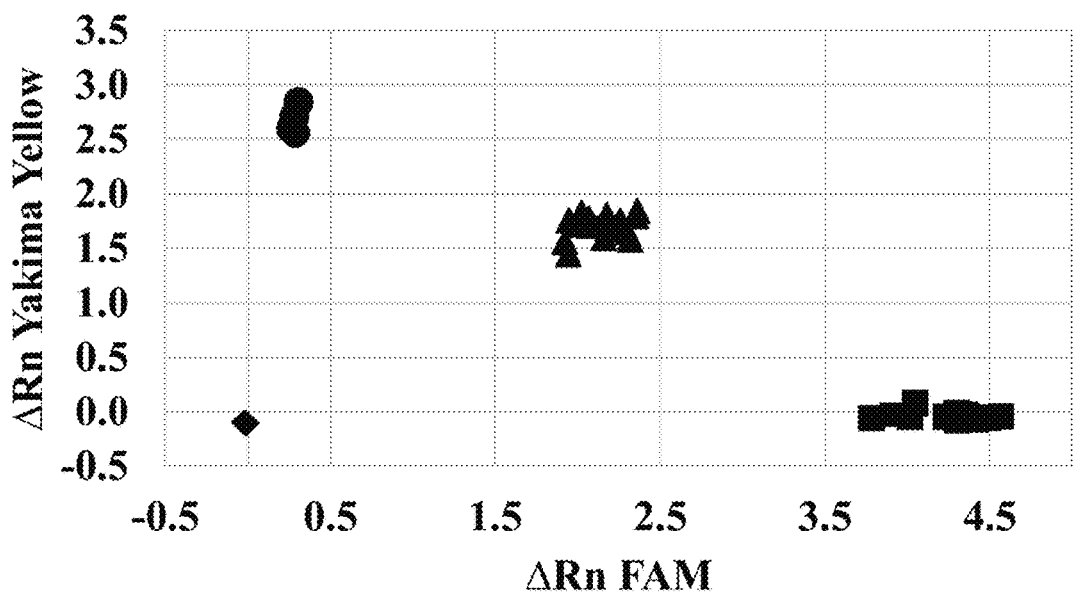

FIGS. 4A and 4B show a side-by-side comparison of the resulting allelic discrimination plots. The rhPCR Genotyping Assay (FIG. 4B) achieved higher fluorescence signal compared to a traditional 5'-nuclease genotyping assay (FIG. 4A) while showing concordant results. The higher signal and minimal non-specific amplification from NTC in the rhPCR assay allow better cluster separation and accurate genotype calls.

EXAMPLE 7

The following example illustrates the present methods allowing for detection and analysis of tri-allelic SNP. The rs72558195 SNP is present in the CYP2C8 gene, and has three potential genotypes. This SNP was selected for analysis with the rhPCR genotyping system.

Figure 5A:
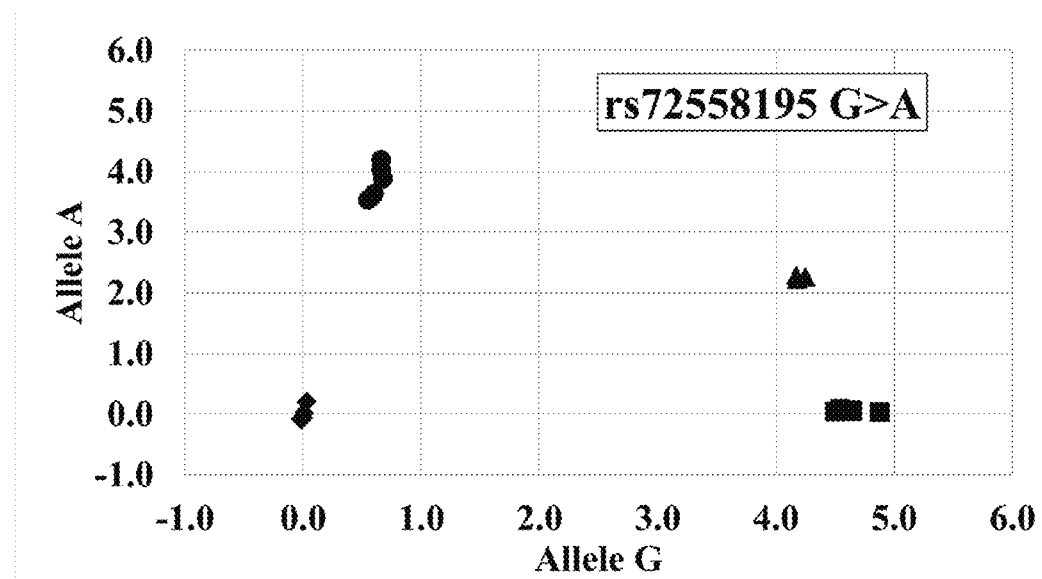
FIGS. 5A and 5B are Allelic Discrimination plots of tri-allelic SNP, CYP2C8 (r572558195), using an rhPCR genotyping single tube multiplex assay on the QuantStudio™ 7 Flex platform (Thermo Fisher).
Figure 5B:
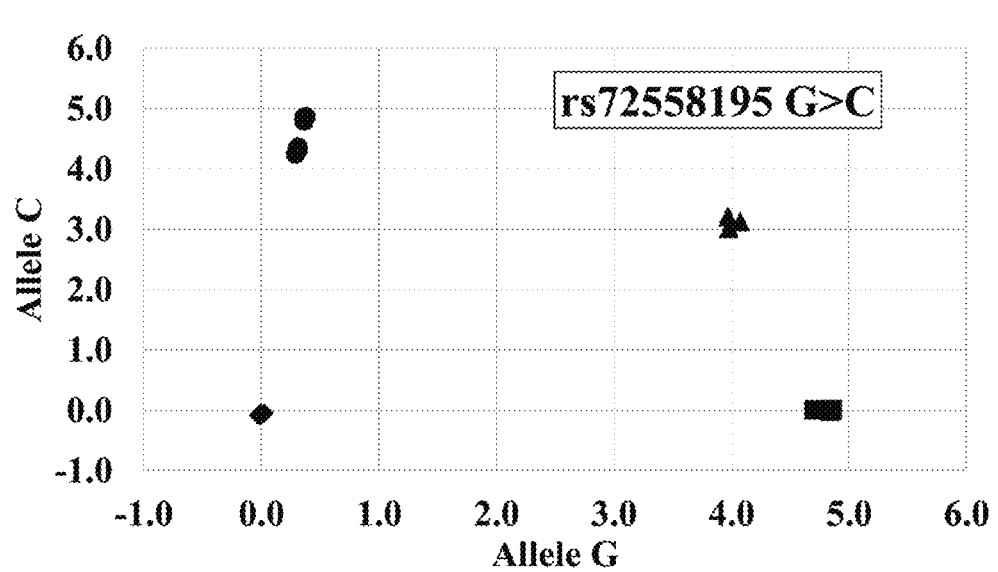
Figure 6:
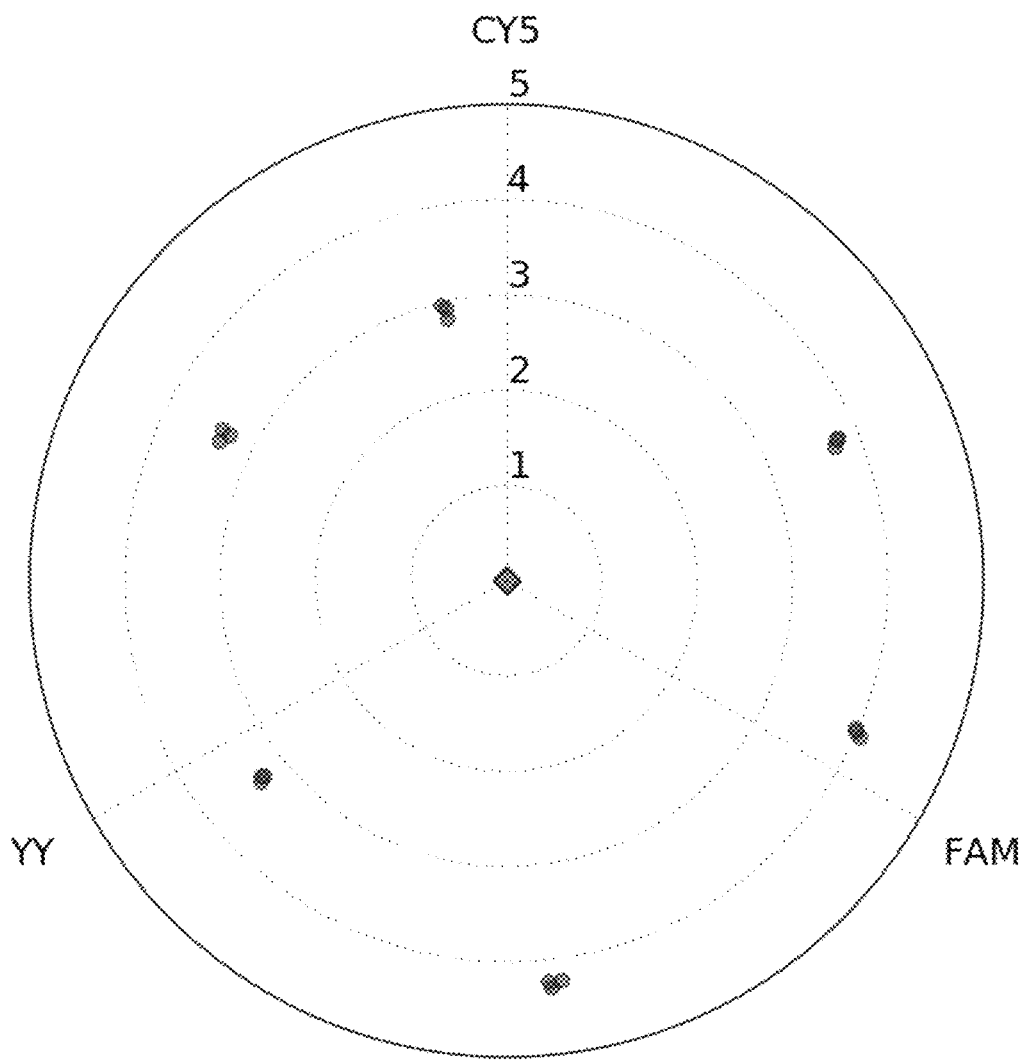
FIG. 6 shows the Tri-allelic Allelic Discrimination 360plot of CYP2C8 rs72558195, using rhPCR genotyping assay with 3 allele-specific primers multiplexed in a single reaction.

Conventional workflow of interrogating tri-allelic SNP, as illustrated in FIGS. 5A and 5B, involves running a pair of assays using the same samples, manual calling, and comparing the paired assay result to obtain the true genotype of samples.

To demonstrate that such a system can function with the universal rhPCR genotyping system, reactions were set up in a white Hard-Shell® 384-well skirted PCR plates (Bio-Rad, Hercules, Calif.) on the Life Technologies (Carlsbad, Calif.) QuantStudio™ 7 Flex real-time PCR with 10 µL final volume. Each well contained the rhPCR assay primers (See Table 16, SEQ ID NOs: 14, 21, 22, 31-33). Specifically, 150 nM of rs72558195 G:A Allele Specific Primer 1 (SEQ ID NO: 31) and 150 nM of rs72558195 G:A Allele Specific Primer 2 (SEQ ID NO: 32), or 150 nM of rs72558195 G:A Allele Specific Primer 1 (SEQ ID NO: 31) and 150 nM of rs72558195 G:C Allele Specific Primer 3 (SEQ ID NO: 33) as well as 500 nM rs72558195 Locus Specific Primer (SEQ ID NO: 34) were included in the reactions.

Reactions contained universal reporter oligos at the following concentrations: 250 nM of universal FAM probe (SEQ ID NO: 14), 450 nM of universal Yakima Yellow® (SEQ ID NO: 22) probe, and 1000 nM of universal forward primer (SEQ ID NO: 21), 50 nM ROX internal standard, and 5 µL of 2× Integrated DNA Technologies (IDT) (Coralville, Iowa) rhPCR genotyping master mix (containing dNTPs, a mutant H784Q Taq polymerase (see Behlke, et al. U.S. 2015/0191707), chemically modified *Pyrococcus abyssi* RNase H2 (See Walder et al. UA20130288245A1), stabilizers, and $MgCl_2$).

TABLE 16

Sequences of oligonucleotides used for the rs72558195 genotyping assay in Example 7.

| Name | Sequence | SEQ ID NO. |
|---|---|---|
| Universal Forward primer | CGGCCCATGTCCCAGCGAA | SEQ ID NO. 21 |
| Probe 1 (FAM) | FAM-C+CATC+A+C+CGTG+CT-IBFQ | SEQ ID NO. 14 |
| Probe 2 (Yakima Yellow) | Yak-CAATC+C+C+CGAG+CT-IBFQ | SEQ ID NO. 22 |
| rs72558195: G:A Allele 1 Forward primer | GCCCATGTCCCAGCGAACCATCACCGTGCTC TCCGTTGTTTTCCAGAAACgATTTC-x | SEQ ID NO. 31 |
| rs72558195: G:A Allele 2 Forward primer | GCCCATGTCCCAGCGAACAATCCCCGAGCTC TCCGTTGTTTTCCAGAAATgATTTC-x | SEQ ID NO. 32 |
| rs72558195: G:C Allele 3 Forward Primer | GCCCATGTCCCAGCGAACAATCCCCGAGCTC TCCGTTGTTTTCCAGAAAGgATTTC-x | SEQ ID NO. 33 |
| rs1135840 Reverse primer | GCAACCAAGTCTTCCCTACAACcTTGAT-x | SEQ ID NO. 34 |

Nucleic acid sequences are shown 5'-3'.
DNA is uppercase, RNA is lowercase.
LNA residues are designated with a +.
Location of potential mismatch is underlined.
FAM = 6-carboxyfluorescein,
Yak = Yakima Yellow (3-(5,6,4',7'-tetrachloro-5'-methyl-3', 6'-dipivaloylfluorescein-2-yl)),
IBFQ = Iowa Black FQ (fluorescence quencher), and
x = C3 propanediol spacer block.

gBlocks® Gene Fragments (Integrated DNA Technologies, Inc., Coralville, Iowa) containing alleles of the rs72558195 SNP were utilized as the source of template DNA (See Table 17, SEQ ID NOs: 35, 36 and 37). Each well contained template representing one of six possible genotypes: allele 1 homozygote (1000 copies rs72558195 Allele 1 gBlock® template (SEQ ID NO: 35)), allele 2 homozygote (1000 copies rs72558195 Allele 2 gBlock® template (SEQ ID NO: 36)), allele 3 homozygote (1000 copies rs72558195 Allele 2 gBlock® template (SEQ ID NO: 37)), heterozygote (mix of 500 copies of rs72558195 Allele 1 gBlock® template (SEQ ID NO: 35) and 500 copies of rs72558195 Allele 2 gBlock® template (SEQ ID NO: 36). heterozygote (mix of 500 copies of rs72558195 Allele 1 gBlock® template (SEQ ID NO: 35) and 500 copies of rs72558195 Allele 3 gBlock® template (SEQ ID NO: 37)). Template or water for the no template control (NTC) reactions were added into three replicate wells of two individual plates. The reactions underwent the following cycling protocol: 95° C. for 10 minutes, then 45 cycles of 95° C. for 10 seconds and 60° C. for 45 seconds.

TABLE 17 qBlock® sequences used in Example 7

| Name | Sequence | SEQ ID NO. |
|---|---|---|
| rs72558195 Allele 1 gBlock template | ACATCATTTTTATTGTATAAAAGCATTTTA GTATCAATTTTCTCATTTTTAAACCAAGTC TTCCCTACAACCTTGAATAAATGGTTTCCA AGGAAAATAAAATCTTGGCCTTACCTGGA TCCATGGGGAGTTCAGAATCCTGAAGTTT TCATTGAATCTTTTCATCAGGGTGAGAAA ATTCTGATCTTTATAATCAAATC<u>G</u>TTTCTG GAAAACAACGGAGCAGATCACATTGCAG GGAGCACAGCCCAGGATGAAAGTGGGAT CACAGGGTGAAGCTAAAGATTTAAAAATT TTTAAAAAAATTATTAAAAAATAAATATT TAAAAGATTTGCATTTGTTAAGACATAAA GGAAATTTAGAAATTTTAAACAATATCTT ACAAATTCCCCATGTGTCCAAA | SEQ ID NO. 35 |
| rs72558195 Allele 2 gBlock template | ACATCATTTTTATTGTATAAAAGCATTTTA GTATCAATTTTCTCATTTTTAAACCAAGTC TTCCCTACAACCTTGAATAAATGGTTTCCA AGGAAAATAAAATCTTGGCCTTACCTGGA TCCATGGGGAGTTCAGAATCCTGAAGTTT TCATTGAATCTTTTCATCAGGGTGAGAAA ATTCTGATCTTTATAATCAAATC<u>A</u>TTTCTG GAAAACAACGGAGCAGATCACATTGCAG GGAGCACAGCCCAGGATGAAAGTGGGAT CACAGGGTGAAGCTAAAGATTTAAAAATT TTTAAAAAAATTATTAAAAAATAAATATT TAAAAGATTTGCATTTGTTAAGACATAAA GGAAATTTAGAAATTTTAAACAATATCTT ACAAATTCCCCATGTGTCCAAA | SEQ ID NO. 36 |
| rs72558195 Allele 3 gBlock template | ACATCATTTTTATTGTATAAAAGCATTTTA GTATCAATTTTCTCATTTTTAAACCAAGTC TTCCCTACAACCTTGAATAAATGGTTTCCA AGGAAAATAAAATCTTGGCCTTACCTGGA TCCATGGGGAGTTCAGAATCCTGAAGTTT TCATTGAATCTTTTCATCAGGGTGAGAAA ATTCTGATCTTTATAATCAAATC<u>C</u>TTTCTG GAAAACAACGGAGCAGATCACATTGCAG GGAGCACAGCCCAGGATGAAAGTGGGAT CACAGGGTGAAGCTAAAGATTTAAAAATT TTTAAAAAAATTATTAAAAAATAAATATT TAAAAGATTTGCATTTGTTAAGACATAAA GGAAATTTAGAAATTTTAAACAATATCTT ACAAATTCCCCATGTGTCCAAA | SEQ ID NO. 37 |

Nucleic acid sequences are shown 5'-3'.
DNA is uppercase. The location of the SNP is underlined.

The results are shown in FIGS. 5A and 5B. From this, it is clear that the universal rhPCR genotyping system can be used to characterize multi-allelic genotypes.

A Tri-allelic AD 360plot was designed for illustrating allelic discrimination. Fluorescence signal (ΔRn) from the last PCR cycle of each dye was normalized across the three dyes from the same well. Angle and distance of data point from the origin is calculated using formula below:

$$\text{Angle} = \tan^{-1}(\Delta RnDye_1 \div \Delta RnDye_2) \times \frac{120}{90}$$

$$\text{Distance from origin} = \sqrt{(\Delta RnDye_1)^2 + (\Delta RnDye_2)^2}$$

FIG. 5B shows the Tri-allelic Allelic Discrimination 360plot of rs72558195, using rhPCR genotyping assay with 3 allele-specific primers multiplexed in a single reaction. By collecting fluorescence signal from all assays, six genotypes could be detected in a single reaction. The distance of data points from origin indicated the signal strength of dyes and the wide angle separation between data clusters indicated specificity of multiplex assay. NTC in the center of the plot indicated no primer dimers or non-specific amplification. The specificity of multiplex assay is achieved by the selectivity of RNase H2 and the mutant Taq DNA polymerase as used in the previous examples. This AD 360plot will also enable auto-calling capability by genotyping software.

A 360plot could be implemented for tetra-allelic, penta-allelic or hexa-allelic visualization. Therefore, visualization is possible for positions that could have multiple bases as well as potential deletions. The distance from origin remains unchanged for each calculation, and the angle formulas would be:

$$\text{tetra-allelic (4 alleles): Angle} = \tan^{-1}(\Delta RnDye_1 \div \Delta RnDye_2)$$

$$\text{penta-allelic (5 alleles): Angle} = \tan^{-1}(\Delta RnDye_1 \div \Delta RnDye_2) \times \frac{72}{90}$$

$$\text{hexa-allelic (6 alleles): Angle} = \tan^{-1}(\Delta RnDye_1 \div \Delta RnDye_2) \times \frac{60}{90}$$

EXAMPLE 8

The following example illustrates the capability of the methods of the present invention to provide quantitative SNP genotyping, allowing for determination of the copy numbers of different alleles. To demonstrate this, an assay was designed against rs1135840, a SNP in the human CYP2D6 gene. This gene can be present in multiple copies, and the number of copies with the rs1135840 SNP appears to affect drug metabolism (rapid metabolism of the drug Debrisoquine).

To demonstrate that the assay system can detect small differences in allele rations, a standard curve for analysis was created. Two gBlock™ (IDT, Coralville, Iowa) gene fragments were synthesized (Allele 1 and Allele 2, representing the two allelic variants (G>C) of the rs1135840 SNP) and then mixed at different ratios. Reactions were performed in 10 µL volumes, containing a total of 1500 copies of template at the ratios shown (10:0, 9:1, 8:2, 7:3, 6:4, 5:5, 4:6, 3:7, 2:8, 1:9, and 0:10), 250 nM of universal FAM probe (SEQ ID NO: 14), 450 nM of universal Yakima Yellow® (SEQ ID NO: 22) probe, 1000 nM of universal forward primer (SEQ ID NO: 21), 150 nM of the two allele-specific forward primers, 500 nM of the reverse primer, and 5 µL of 2× Integrated DNA Technologies (IDT) (Coralville, Iowa) rhPCR genotyping master mix (containing dNTPs, a mutant H784Q Taq polymerase (see Behlke, et al. U.S. 2015/0191707), chemically modified *Pyrococcus abyssi* RNase H2 (See Walder et al. UA20130288245A1), stabilizers, and MgCl$_2$).

PCR was performed on Life Technologies (Carlsbad, Calif.) QuantStudio™ 7 Flex real-time PCR instrument using the following cycling conditions: 10 mins at 95° C. followed by 45 cycles of 95° C. for 10 seconds and 60° C. for 45 seconds. End-point analysis of each of the plates was performed after 45 cycles with software provided by the respective companies (Bio-Rad CFX Manager 3.1 software (Bio-Rad, Hercules, Calif.) and QuantStudio™ Real-Time PCR Software v1.3 (Carlsbad, Calif.)).

TABLE 16

Oligonucleotide sequences used in Example 8.

| Name | Sequence | SEQ ID NO. |
|---|---|---|
| Universal Forward primer | CGGCCCATGTCCCAGCGAA | SEQ ID NO. 21 |
| Probe 1 (FAM) | FAM-C+CATC+A+C+CGTG+CT-IBFQ | SEQ ID NO. 14 |
| Probe 2 (Yakima Yellow) | Yak-CAATC+C+C+CGAG+CT-IBFQ | SEQ ID NO. 22 |
| rs1135840 Allele 1 Forward primer | GCCCATGTCCCAGCGAACCATCACCGTGC TGTCTTTGCTTTCCTGGTGA<u>G</u>cCCATG-x | SEQ ID NO. 38 |
| rs1135840 Allele 2 Forward primer | GCCCATGTCCCAGCGAACAATCCCCGAGC TGTCTTTGCTTTCCTGGTGA<u>C</u>cCCATG-x | SEQ ID NO. 39 |
| rs1135840 Reverse primer | GCGTTGGAACTACCACATTGCTTTATuGTA CT-x | SEQ ID NO. 40 |

Nucleic acid sequences are shown 5'-3'.
DNA is uppercase, RNA is lowercase.
LNA residues are designated with a +.
Location of potential mismatch is underlined.
FAM = 6-carboxyfluorescein,
Yak = Yakima Yellow (3-(5,6,4',7'-tetrachloro-5'-methyl-3', 6'-dipivaloylfluorescein-2-yl)),
IBFQ = Iowa Black FQ (fluorescence quencher), and
x = C3 propanediol spacer block.

Figure 7:
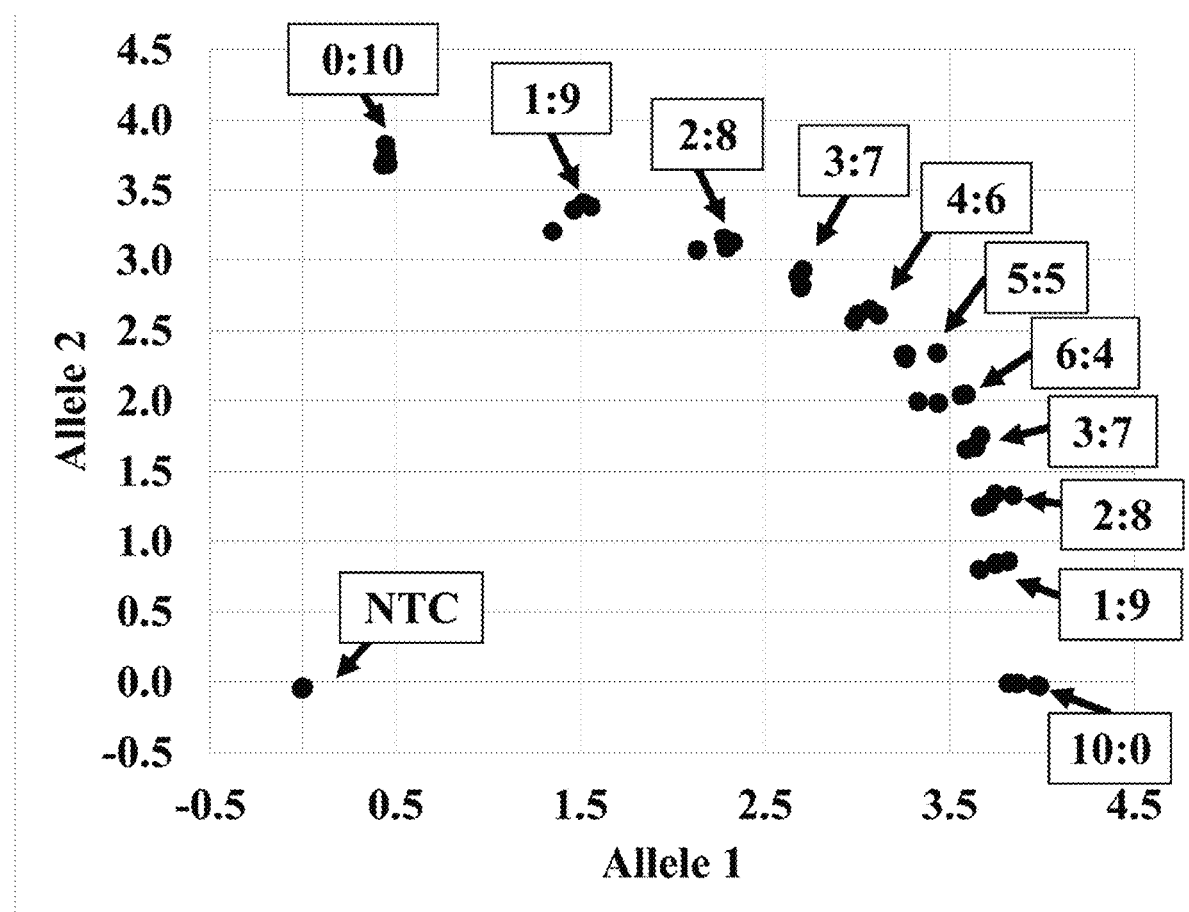
FIG. 7 is an allelic discrimination plot illustrating the ability of the rhPCR assay to perform quantitative genotyping.

The resulting data is illustrated in FIG. 7. The spread of each of the sample mixes is sufficient for the determination of the number of copies of each template.

After demonstration of the required amount of separation of allelic quantities, it is possible to determine the number of copies present of each allele in an experimental sample. To test this, the previously described assay designed against rs1135840, was utilized to test thirteen Coriell genomic DNA (Camden, N.J.) samples with varying CYP2D6 copy numbers with varying rs1135840 genotypes. These samples have known defined copy numbers and rs1135840 genotypes which could be verified after testing with the universal rhPCR genotyping mix. From this, these samples can also be categorized as being homozygotes for either allele, or heterozygotes.

To calculate the copy number from the data, two duplex reactions were run for each sample. Reactions were performed in 10 µL volumes, containing 3 ng of one of the following genomic DNAs: NA17123, NA17131, NA17132, NA17149, NA17104, NA17113, NA17144, NA17213, NA17221, NA17114, NA17235, or NA17241. Each individual assay also contained 50 nM ROX normalizer oligo, 250 nM of universal FAM probe (SEQ ID NO: 14), 450 nM of universal Yakima Yellow® (SEQ ID NO: 22) probe, 1000 nM of universal forward primer (SEQ ID NO: 21), 150 nM of the two allele-specific forward primers (SEQ ID NO: 38 and 39), 500 nM of the reverse primer (SEQ ID NO: 40), and 5 µL of 2× Integrated DNA Technologies (IDT) (Coralville, Iowa) rhPCR genotyping master mix (containing dNTPs, a mutant H784Q Taq polymerase (see Behlke, et al. 2015/0191707), chemically modified *Pyrococcus abyssi* RNase H2 (See Walder et al. UA20130288245A1), stabilizers, and MgCl$_2$). Assays also contained a separate RNase P assay (See table 17, SEQ ID NOs: 41-43)) for normalization of the template concentration.

TABLE 17

RNase P assay sequences used in Example 8.

| Name | Sequence | SEQ ID NO. |
|---|---|---|
| RNase P Forward primer | GCGGAGGGAAGCTCATCAG | SEQ ID NO. 41 |
| RNase P Reverse primer | CCCTAGTCTCAGACCTTCCCAA | SEQ ID NO. 42 |
| Probe 2 (Yakima Yellow) | Yak-CCACGAGCTGAGTGCGTCCTGTCA-IBFQ | SEQ ID NO. 43 |

Nucleic acid sequences are shown 5'-3'.
DNA is uppercase.
FAM = 6-carboxyfluorescein,
Yak = Yakima Yellow (3-(5,6,4',7'-tetrachloro-5'-methyl-3',6'-dipivaloylfluorescein-2-yl)),
IBFQ = Iowa Black FQ (fluorescence quencher).

Quantitative PCR was performed on Life Technologies (Carlsbad, Calif.) QuantStudio™ 7 Flex real-time PCR instrument using the following cycling conditions: 10 mins at 95° C. followed by 45 cycles of 95° C. for 10 seconds and 60° C. for 45 seconds. End-point analysis of each of the plates was performed after 45 cycles with the QuantStudio™ Real-Time PCR Software v1.3 (Carlsbad, Calif.) software provided by the company.

Copy number was determined by the following method. For each sample shown to be a homozygote, ΔCq (RNase P Cq—rs1135840 assay Cq) was calculated for each sample. For samples shown to be heterozygotes, ΔCq was calculated for both alleles (RNase P Cq—rs1135840 assay 1 Cq and RNase P Cq—rs1135840 assay 2 Cq). Next, ΔΔCq (ΔCq—mean ΔCq for known 2 copy control DNA samples) was calculated for each allele. This correction allowed for normalization against amplification differences between the SNP assay and the RNase P assay. Finally, the following equation was used to calculate copy number for each allele:

Copy number of allele=2*(2^(ΔΔCq))

Figure 8A:
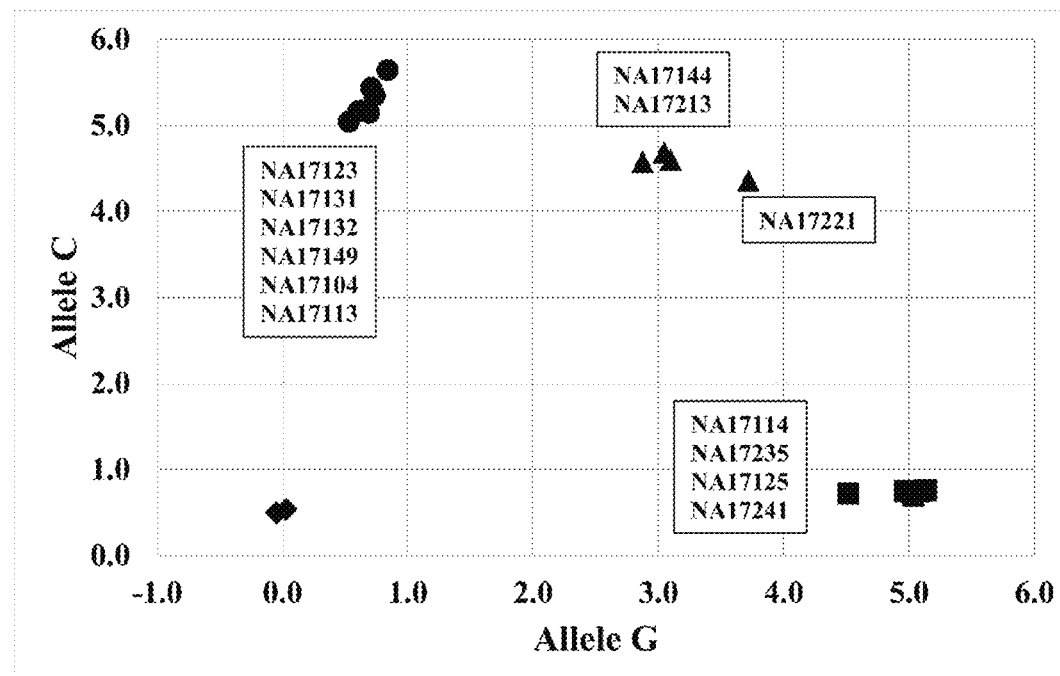
FIGS. 8A and 8B illustrate genotyping results and detection of allelic copy number variation that is possible with the present invention. gDNA samples were tested using varying copy numbers and varying reference genotypes.
Figure 8B:
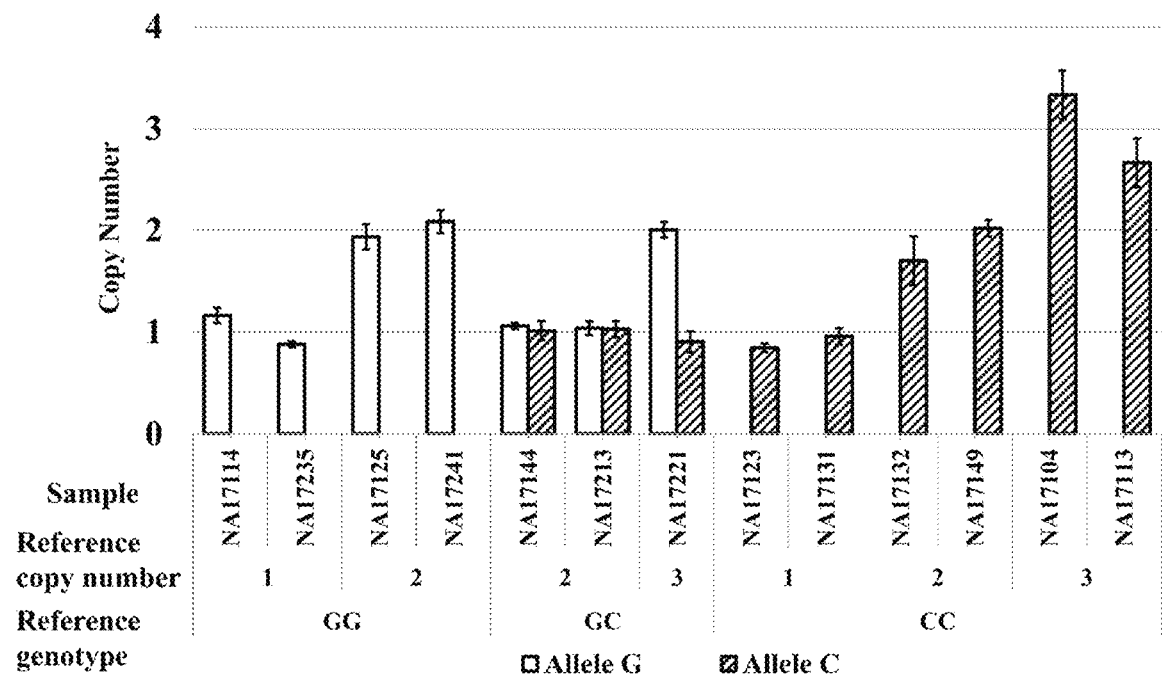

The resulting end-point data is shown in FIG. 8A and calculated copy numbers are shown in FIG. 8B. The genotypes determined in FIG. 8A (homozygotes allele 1, Homozygotes allele 2, or heterozygote) all matched the known genotypes, and allowed correct calculation of the copy number. The established reference copy number of the individual samples is shown under each result. In each case, the copy number determined by the assay correctly determined the genotype and copy number of the input DNA.

EXAMPLE 9

The following example demonstrates that a variation of an rhPCR probe can be used for multiplexed rhPCR.

Figure 9:
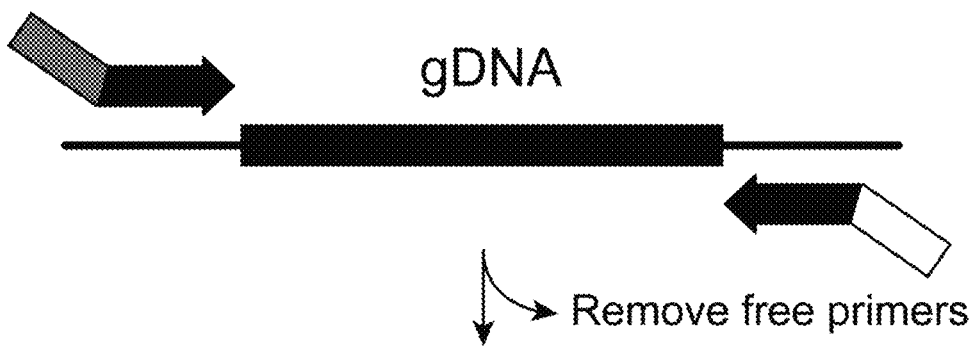
FIG. 9 is a schematic representation of multiplex rhPCR.
Figure 9:
Figure 9:
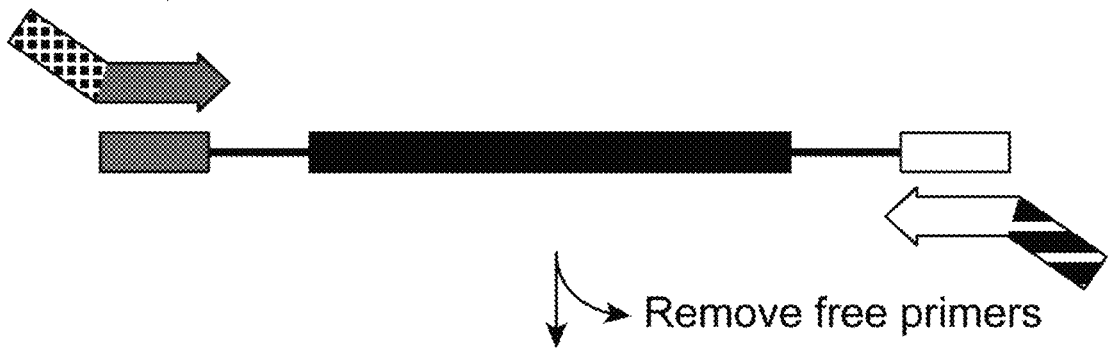
Figure 9:

The assay schematic is provided in FIG. 9. In the first round of PCR, 5' tailed target-specific rhPrimers are used. The 5' tails upon incorporation into the amplicon contain binding sites for a second round of PCR with different primers (blocked or unblocked) to add application specific sequences. For example, as depicted in FIG. 9, this system can be used for amplification enrichment for next generation sequencing. In this case, 5' tailed rhPCR primers contain read 1/read 2 primer sequences. The second round of PCR adds adapter sequences such as the P5/P7 series for Illumina® based sequencing platforms or other adaptors, including ones containing barcodes/unique molecular identifiers. This approach allows for adding any additional sequences onto the amplicon necessary for input into any NGS platform type.

Figure 10:
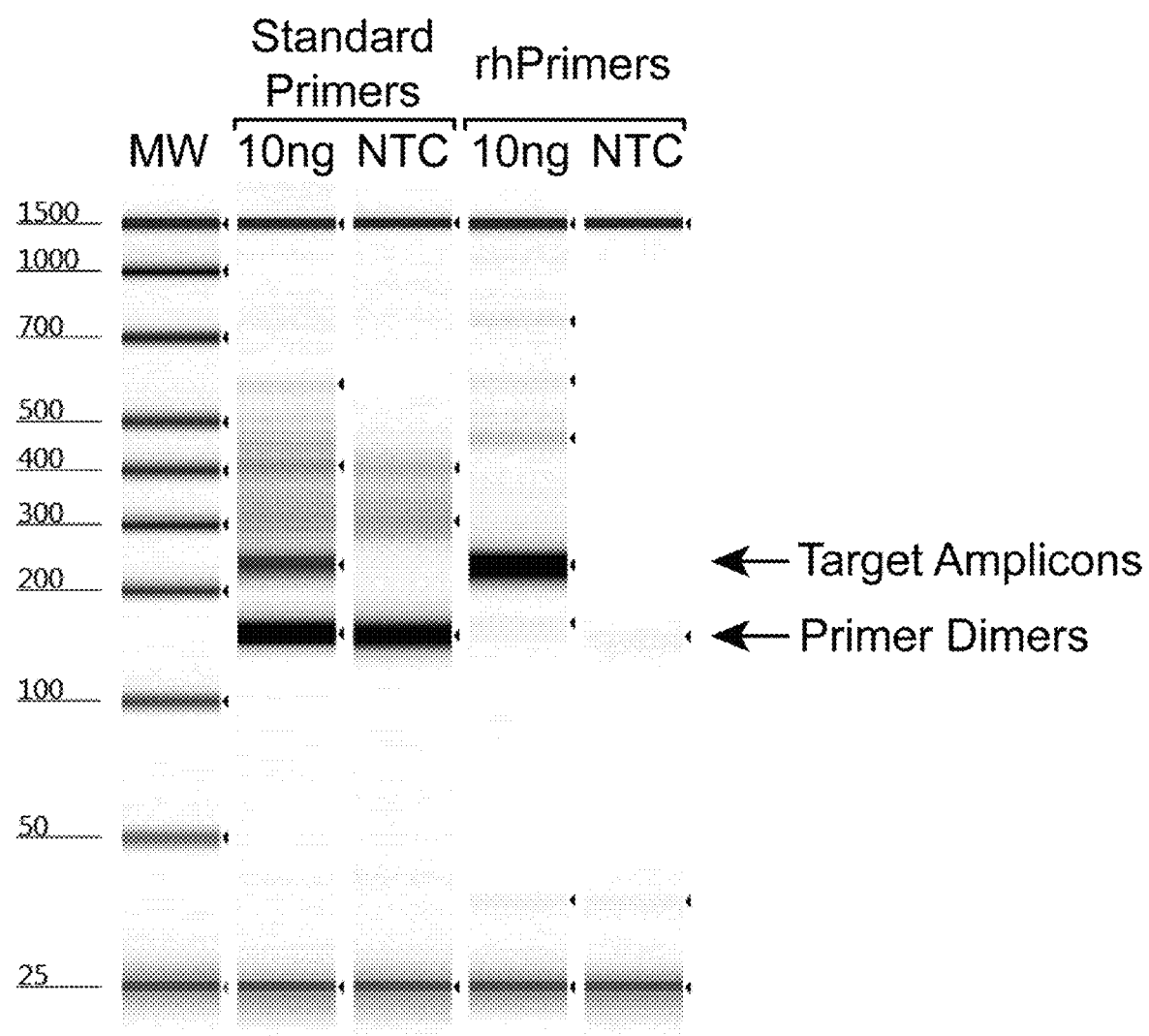
FIG. 10 is the resulting tape station image indicating the effectiveness of the multiplex rhPCR methods in reducing primer dimers and increasing desired amplicon yield.

As illustrated in FIG. 10, two primers sets, including one containing a 96-plex set of 5' tailed rhPrimers, and one containing 96 DNA "standard" 5' tailed PCR primers were designed using an IDT algorithm. The two primer sets differed only in that the rhPrimers contained an internal cleavable RNA base and a blocking group on the 3' end. Once the blocking group was removed by RNase H2 cleavage, the primer sequences become identical.

The first round of PCR reactions contained the 96 plex at 10 nM of each blocked target specific primer, 10 ng of NA12878 human genomic DNA (Coriell Institute for Medical Research, Camden, N.J.), 200 mU of chemically modified *Pyrococcus abyssi* RNase H2 (See Walder et al. UA20130288245A1) (IDT, Coralville, Iowa) and 1×KAPA 2G HotStart Fast Ready Mix™ (Kapa Biosystems, Wilmington, Mass.). The thermal cycling profile was 10 mins at 95° C. followed by 8 cycles of 95° C. for 15 seconds and 60° C. for 4 minutes, and a final 99° C. finishing step for 15 minutes. Reactions were cleaned up with a 2×AMPure™ XP beads (Beckman Coulter, Brea, Calif.). Briefly, 100 μL AMPure™ SPRI beads were added to each PCR well, incubated for 5 minutes at room temperature and collected for 5 minutes at room temperature on plate magnet (DynaMag™ (Thermo-Fisher, (Watherham, Mass.) 96-well plate side-magnet). Beads were washed twice with 80% ethanol, and allowed to dry for 3 minutes at room temperature. Samples were eluted in 22 μL of TE at pH 8.0.

The second round of PCR was set up using 20 μL of the cleaned up first round PCR products, universal PCR-50F and PCR-47R primers (See table 18, SEQ ID NOs: 44 and 45) at 2 uM and 1×KAPA 2G HotStart Fast Ready Mix™ (KAPA Biosystems, Wilmington, Mass.). Reactions were cycled for 45 seconds at 98° C. followed by 20 cycles of 98° C. for 15 seconds, 60° C. for 30 seconds, and 72° C. for 30 seconds. A final 1 minute 72° C. polishing step finished the reaction. Samples were cleaned up again with 0.8×AMPure™ beads. Briefly, 40 μL AMPure™ SPRI beads were added the second PCR wells, incubated for 5 minutes at room temperature and collected for 5 minutes at room temperature on plate magnet (DynaMag™ (Thermo-Fisher, (Watherham, Mass.) 96-well plate side-magnet). Beads were washed twice with 80% ethanol, and allowed to dry for 3 minutes at room temperature. Samples were eluted in 22 μL of TE at pH 8.0, and 20 μL was transferred to a new tube.

2 μL of the samples were analyzed using the Agilent® High Sensitivity D1000™ Screen Tape™ on the Agilent® 2200 Tape Station™ (Agilent Technologies®, Santa Clara, Calif.). Quantification was performed using the KAPA Library Quantification Kit (KAPA Biosystems, Wilmington, Mass.) for Illumina® Platforms, according to the manufacturer's protocol. Replicate samples were pooled to a final concentration of 10 pM, and 1% PhiX bacteriophage sequencing control was added. Samples were run with a V2 300 cycle MiSeq™ kit on an Illumina® (San Diego, Calif.) MiSeq™ platform, using standard protocols from the manufacturer.

TABLE 18

Universal assay sequences used in Example 9.

| Name | Sequence | SEQ ID NO. |
|---|---|---|
| Universal PCR-50F | AATGATACGGCGACCACCGAGATCTACAC TCTTTCCCTACACGACGCTCT | SEQ ID NO. 44 |
| Universal PCR-47R | CAAGCAGAAGACGGCATACGAGATGGACC TATGTGACTGGAGTTCAGACGTGTGC | SEQ ID NO. 45 |

Nucleic acid sequences are shown 5'-3'.
DNA is uppercase.

FIG. 10 shows the results from the Agilent® Tape Station. The primer dimer product was the most significant product produced using standard DNA primers in the presence of DNA template, with only a small amount of full length expected product. In the absence of template, the primer dimer product was the major component of the reaction. In the case of the blocked rhPCR primers, the vast majority of the material was the desired PCR products, with little primer dimer observed. In the absence of template, there is no primer dimer present, contrasting with the overwhelming abundance of primer dimer observed in the no template lane of the unblocked DNA primers. Quantitation of the product versus primer dimer bands show that mass ratio of product to primer dimer for the unblocked DNA primers was 0.6. The mass ratio for the rhPCR primers was 6.3.

Figure 11:
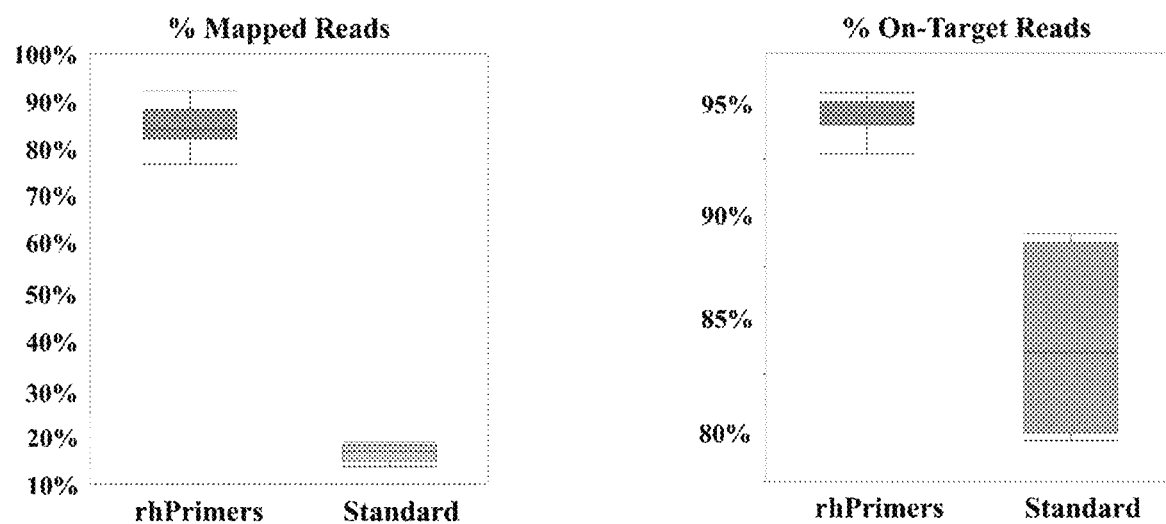
FIG. 11 graphically represents the effectiveness of the rhPrimers in the percent of mapped reads and on-target reads.

FIG. 11 summarizes two key sequencing metrics. The first is the percent of mapped reads from the sequencing data. The rhPCR reactions gave a percentage of reads mapped to the human genome at 85%, whereas the non-blocked DNA primers on give a mapped read percentage of less than 20. A second metric, the percentage of on-target reads, is almost 95% when using rhPCR primers, but less than 85% when the non-blocked primers are used in the multiplex. These results clearly demonstrate the utility of using rhPCR in multiplexing, where a large increase of the desired material is seen, and a vast reduction in undesired side products is observed. The differences mean less unwanted sequencing reads, and the depth of coverage of desired sequences is higher.

EXAMPLE 10

This example demonstrates enhanced sensitivity and accuracy of assay systems of the disclosure as compared to standard T7 endonuclease cleavage assays.

A total of 36 sites modified with the CRISPR/Cas9 protein system were chosen to be comparatively analyzed by T7 endonuclease, next-generation sequencing (NGS), or a qPCR "Genie" assay system of the disclosure.

To mutate the chosen genomic sites, a HEK293 cell line was generated with stable expression of S pyogenes Cas9. AltR™ guide RNAs were reverse transfected into the cells in 96-well plates (40,000 cells/well) using 0.75 µL RNAiMAX (Thermo) per well. Briefly, AltR™ crRNAs were designed from the IDT CRISPR2.0 design engine to target exon 1 or 2 of selected human genes. Prior to transfection, guide RNAs (crRNA/tracrRNA with AltR™ chemistry) were duplexed in an equimolar ratio at 3 µM final concentration of the complex in IDT duplex buffer (Integrated DNA Technologies, Coralville, Iowa). Complexes were heated to 95° C. for 5 min and cooled to room temperature. Genomic DNA was isolated after 48 hrs with 50 µL Quick Extract buffer (Epicentre), using standard techniques described by the manufacturer. DNA solutions were further diluted with 100 µL water before further analysis was performed.

Analysis by T7 endonuclease digestion was done as follows. CRISPR-Cas9-treated cells were washed with 100 µL of PBS. Cells were lysed by adding 50 µL of QuickExtract™ DNA Extraction Solution (Integrated DNA Technologies). Cell lysates were then transferred to appropriate PCR tubes or plate, then vortexed and heated in a thermal cycler at 65° C. for 10 min, followed by 98° C. for 5 min, after which 100 µL of Nuclease-Free Water was added to dilute the genomic DNA. The samples were then vortexed and spun down. PCR was set up using template, primers, and components of the Alt-R Genome Editing Detection Kit and KAPA HiFi HotStart PCR Kit as follows. Sample: 4 µL (~40 ng) genomic DNA, 300 nM forward primer, 300 nM reverse primer, 5 µL (1λ) of KAPA HiFi Fidelity Buffer (5λ), 1.2 mM (0.3 mM each) dNTPs, 0.5 U KAPA HiFi Hotstart DNA Polymerase (1 U/µL), for a total volume of 25 µL. Alt-R™ Control A: 1 µL Alt-R™ Control A template/primer mix, 5 µL (1×) of KAPA HiFi Fidelity Buffer (5×), 1.2 mM (0.3 mM each) dNTPs, 0.5 U KAPA HiFi Hotstart DNA Polymerase (1 U/µL), for a total volume of 25 µL. Alt-R™ Control B: 1 µL Alt-R™ Control B template/primer mix, 5 µL (1×) of KAPA HiFi Fidelity Buffer (5×), 1.2 mM (0.3 mM each) dNTPs, 0.5 U KAPA HiFi Hotstart DNA Polymerase (1 U/µL), for a total volume of 25 µL. PCR was run using the following conditions: denature at 95° C. for 5 min; 30 cycles of: denature at 98° C. for 20 sec, anneal between 64-67° C. (depending on polymerase) for 15 sec, extend at 72° C. for 30 sec; then extend at 72° C. for 2 minutes. Heteroduplexes for T7EI digestion were formed as follows. 2 µL T7EI Reaction Buffer (10×) and 6 µL Nuclease-Free Water was combined with 10 µL experimental target or Alt-R HPRT control from the PCR, 10 µL Control A PCR component (homoduplex control), or 5 µL Control A and 5 µL Control B (heteroduplex control). The PCR products were then placed in a thermal cycler with 95° C. denaturation for 10 min, ramp from 95-85° C. at a ramp rate of −2° C./sec, then ramp from 85-25° C. at a ramp rate of −0.3° C./sec. 18 µL of PCR heteroduplexes from the previous step were combined with 2 µL T7 endonuclease I (1 U/µL), then the T7EI reaction was incubated at 37° C. for 60 min. T7EI mismatch detection result were visualized on a Fragment Analyzer™ system with Mutation Discovery Kit according to the manufacturer's instructions (Integrated DNA Technologies). After amplification and cleavage, amplicons were sized on the Fragment Analyzer™ (Advanced Analytical, Inc, Ames, Iowa) capillary electrophoresis system.

NGS sequencing analysis of the mutated samples employed locus-specific primers positioned approximately 75-bp flanking the Cas9 cleavage site. Primers contained universal 5'-tails that allowed for secondary amplification that added Illumina™ TruSeq™ i5 and i7 adapters with sample-specific barcodes to the amplicons. The locus-specific primers were designed as RNase H2-cleavable primers with the 4DMX blocking modification at the 3'-end (where the 4DMX nomenclature indicates 4 DNA bases, a mismatched DNA base and a propanediol C3-spacer 3' of the RNA base). Using a master-mix containing a hot-start Taq polymerase and hot-start RNaseH2, the genomic DNAs were amplified using the following cycling conditions: $95°C.^{5:00}+(95°C.^{0:15}+60°C.^{1:00})\times8$ cycles+$99°C.^{15:00}$. Samples were purified using SPRI beads (1.5× Agencourt™ Ampure® XP beads, Beckman Coulter) per the manufacturer's protocol. The second PCR incorporated the Illumina adapters and was run under the following conditions: 95° C.$^{5:00}$+(95° C.$^{0:15}$+60° C.$^{0:30}$+72° C.$^{0:30}$)×18 cycles+99° C.$^{15:00}$.

The resultant amplicons underwent 1×SPRI™ clean-up and were quantified via the KAPA™ library qPCR quantitation (KAPA Biosystems, Wilmington, Mass.) kit per the manufacturer's recommended protocol. In addition, amplicons were sized on the Fragment Analyzer™ (Advanced Analytical, Inc., Ames, Iowa) capillary electrophoresis system.

DNA sequencing was carried out on an Illumina™ MiSeq® using a MiSeq® Nano cartridge (v2, 300 cycles). Data was de-multiplexed via an in-house bioinformatics processing pipeline. Analysis for specific editing events relative to a reference amplicon was performed with CRISPResso™ using methods described.

Quantitative PCR assay primers for analysis according to methods of the disclosure were designed so that the RNA nucleotide was located two bases after the primary Cas9 cleavage site, allowing for maximal discrimination from both the RNase H2 enzyme and the DNA polymerase (FIG. 12). Primers were designed to include a proprietary universal 5' domain (UniFor-UniPro-), which has sequence identity with both a universal forward primer, and a universal 5' nuclease degradable probe (Table 1, Seq ID No. 1-72 and Table 2, Seq ID No. 76-147). A Taqman-based RNase P assay (Seq ID No. 73-75) was utilized as a universal control for template concentration normalization in all cases. All primers were synthesized at Integrated DNA Technologies (IDT, Coralville, Iowa). Amplification was performed with 2.5 μL of the same QuickExtract™ genomic DNA utilized in T7 and NGS analyses. A wild-type (WT) control that was grown and extracted by the same method was also analyzed for normalization purposes. Reaction volumes were 10 μL in all cases, and included the universal forward primer, the universal probe, the interrogating primer, and the non-interrogating reverse primer. 1× of a rhPCR-genotyping master mix, containing hot-start RNase H2, a thermophilic DNA polymerase, buffer, and dNTPs was also included. The universal forward primer was present in all reactions at 1000 nM (10 pmol), and the universal assay probe was present at 300 nM (3 pmol). The assay specific primers were present at 200 nM (2 pmol) for the forward (mutation interrogating) primer, while the non-interrogating locus-specific reverse primer was present at 500 nM (5 pmol). RNase P control reactions were run with 500 nM of forward and reverse RNase P primers, and 250 nM probe (Seq ID No. 73-75). Reactions were run on a CFX384™ Real-Time qPCR machine (Bio-Rad®, Hercules, Calif.). The following cycling conditions were utilized: 95° C.$^{10:00}$+(95° C.$^{0:15}$+59° C.$^{0:20}$+72° C.$^{0:30}$)×55 cycles.

TABLE 1

Discriminatory forward primers utilized in Example 1.

| Name | Sequence | Seq ID No. |
|---|---|---|
| GCK-356-1 | UniFor-UniPro-CCCTGGGTCCCTGGGaGAATC-x | 46 |
| GCK-356-2 | UniFor-UniPro-CGAGGAGAACCACATTCTCCcAGGGT-x | 47 |
| ERBB3-33-1 | UniFor-UniPro-GGGCGGCCGTGACuCACC-x | 48 |
| ERBB3-33-2 | UniFor-UniPro-GAGGGAAGGGGGTGAGTcACGGCG-x | 49 |
| TTR-1257-1 | UniFor-UniPro-CCTGGGAGCCATTTGCCTCuGGGTT-x | 50 |
| TTR-1257-2 | UniFor-UniPro-CTTTGGCAACTTACCCAGAGGcAAATC-x | 51 |
| HAMP-253-1 | UniFor-UniPro-GCACTGAGCTCCCAGAuCTGGC-x | 52 |
| HAMP-253-2 | UniFor-UniPro-GCAAGCGGCCCAGATCuGGGAC-x | 53 |
| BIRC5-606-1 | UniFor-UniPro-GACGACCCCATGTAAGTCTTCuCTGGG-x | 54 |
| BIRC5-606-2 | UniFor-UniPro-CGAGGCTGGCCAGAGAaGACTTT-x | 55 |
| SAA 146-1 | UniFor-UniPro-CTTTCCCAACAAGATTATCATTTCCTTTAAaAAAAT-x | 56 |
| SAA 146-2 | UniFor-UniPro-CGCCCCAGGATAACTATTTTTTTaAAGGT-x | 57 |
| IDO1-97-1 | UniFor-UniPro-AGACACTGAGGGGCACCaGAGGT-x | 58 |
| IDO1-97-2 | UniFor-UniPro-CTTGTAGTCTGCTCCTCTGGuGCCCG-x | 59 |
| IDO1-176-1 | UniFor-UniPro-AGTAAAGAGTACCATATTGATGAAGAAgTGGGA-x | 60 |
| IDO1-176-2 | UniFor-UniPro-GCAGAGCAAAGCCCACTTcTTCAA-x | 61 |
| CYP27A-31016-1 | UniFor-UniPro-CCTTTGGTGAGGACTCCCAgATGGC-x | 62 |
| CYP27A-31016-2 | UniFor-UniPro-CCTGGGCCCCATCTGgGAGTG-x | 63 |
| SAA 226-1 | UniFor-UniPro-TCTCCTCTGATCTAGAGAGGTAAGcAGGGA-x | 64 |

TABLE 1-continued

Discriminatory forward primers utilized in Example 1.

| Name | Sequence | Seq ID No. |
|---|---|---|
| SAA 226-2 | UniFor-UniPro-ACCAGGCCCGACCCTGCTuACCTG-x | 65 |
| KIF11-369-1 | UniFor-UniPro-GAGAAGGGGAAGAACATCCAgGTGGA-x | 66 |
| KIF11-369-2 | UniFor-UniPro-GCATCTCACCACCACCTGgATGTA-x | 67 |
| C3-1394-1 | UniFor-UniPro-CTGGACAGCACTAGTTTTTTGCcTGGGT-x | 68 |
| C3-1394-2 | UniFor-UniPro-CCACGACTTCCCAGGCaAAAAT-x | 69 |
| HOGA-505-1 | UniFor-UniPro-CACTGCAGAGGTGGACTaTGGGT-x | 70 |
| HOGA-505-2 | UniFor-UniPro-GATTCTCCTCCAGTTTCCCATAGuCCACG-x | 71 |
| EGFR-123344-1 | UniFor-UniPro-CCAGAGGATGTTCAATAACTGTGAgGTGGA-x | 72 |
| EGFR-123344-2 | UniFor-UniPro-CAAATTCCCAAGGACCACCuCACAC-x | 73 |
| ALDH2-15144-1 | UniFor-UniPro-TGAAGGGGACAAGGTGAGAaCTGGA-x | 74 |
| ALDH2-15144-2 | UniFor-UniPro-CCCAAGGTAAGTCACCAGTTCuCACCA-x | 75 |
| AGXT-140-1 | UniFor-UniPro-CCATGGCCTCTCACAAGCTgCTGGA-x | 76 |
| AGXT-140-2 | UniFor-UniPro-GGGGGTCACCAGCAGcTTGTC-x | 77 |
| APOC-2929-1 | UniFor-UniPro-CCGTTAAGGACAAGTTCTCTGAGTuCTGGC-x | 78 |
| APOC-2929-2 | UniFor-UniPro-TCAGGGTCCAAATCCCAGAACuCAGAC-x | 79 |
| Met 27554-1 | UniFor-UniPro-AATTTTATTTACTTCTTGACGGTCCAAAGGgAAACA-x | 80 |
| Met 27554-2 | UniFor-UniPro-GTCTGAGCATCTAGAGTTTCCCuTTGGT-x | 81 |
| SAA 88-1 | UniFor-UniPro-AGGTGAGGAGCACACCAAGGAgTGATA-x | 82 |
| SAA 88-2 | UniFor-UniPro-GAAAACAGAGTAAGTTTTAAAAATCACTCcTTGGA-x | 83 |
| HIF1A-293-1 | UniFor-UniPro-TCGCACCCCCACCTcTGGAG-x | 84 |
| HIF1A-293-2 | UniFor-UniPro-GAAGGAAAGGCAAGTCCAGAGgTGGGC-x | 85 |
| Met 27475-1 | UniFor-UniPro-AATTTTATTTACTTCTTGACGGTCCAAAGGgAAACA-x | 86 |
| Met 27475-2 | UniFor-UniPro-GTCTGAGCATCTAGAGTTTCCCuTTGGT-x | 87 |
| HAMP-295-1 | UniFor-UniPro-CTCGCCAGCCTGACCaGTGGG-x | 88 |
| HAMP-295-2 | UniFor-UniPro-GGGAAAACAGAGCCACTGGuCAGGG-x | 89 |
| GRHPR-2234-1 | UniFor-UniPro-GCCTCCTCTCCGACCAcGTGGT-x | 90 |
| GRHPR-2234-2 | UniFor-UniPro-GGATCCTCTTGTCCACGTGGgTCGGAC-x | 91 |
| HAMP-88-1 | UniFor-UniPro-GGCGCCACCACCTTcTTGGT-x | 92 |
| HAMP-88-2 | UniFor-UniPro-GCTCTGTCTCATTTCCAAGAAgGTGGA-x | 93 |
| Met 27254-1 | UniFor-UniPro-GAGCCAAAGTCCTTTCATCTGTaAAGGT-x | 94 |
| Met 27254-2 | UniFor-UniPro-GAAGTTGATGAACCGGTCCTTTACaGATGT-x | 95 |
| GRHPR-2264-1 | UniFor-UniPro-ACAAGAGGATCCTGGATGCTgCAGGA-x | 96 |

TABLE 1-continued

Discriminatory forward primers utilized in Example 1.

| Name | Sequence | Seq ID No. |
|---|---|---|
| GRHPR-2264-2 | UniFor-UniPro-CGCTCTAGCTCCTTGGCaGGGAA-x | 97 |
| Serpina 279-1 | UniFor-UniPro-ACTCAGTTCCACAGGTGGGAggGAGGC-x | 98 |
| Serpina 279-2 | UniFor-UniPro-CACTCTAAGCCCTGCTGTCCCaCCTGA-x | 99 |
| Myc 459-1 | UniFor-UniPro-CGGGAGGCTATTCTGCCCATTuGGGAT-x | 100 |
| Myc 459-2 | UniFor-UniPro-CGGGGAAGTGTCCCCAAAuGGGCT-x | 101 |
| Serpina 130-1 | UniFor-UniPro-GCTGCTGCTGCCAGGAAuTCCAC-x | 102 |
| Serpina 130-2 | UniFor-UniPro-CCCCTCCAACCTGGAATTcCTGGG-x | 103 |
| Myc 490-1 | UniFor-UniPro-CTGCCAGGACCCGCTTCuCTGAT-x | 104 |
| Myc 490-2 | UniFor-UniPro-CAAGGAGAGCCTTTCAGAGAaGCGGC-x | 105 |
| GRHPR-2179-1 | UniFor-UniPro-GATGAGCCCATCCCTGCcAAGGT-x | 106 |
| GRHPR-2179-2 | UniFor-UniPro-CGCTCTAGCTCCTTGGCaGGGAA-x | 107 |
| GYG-2851-1 | UniFor-UniPro-TCGCCACCCCTCAGGuCTCAC-x | 108 |
| GYG-2851-2 | UniFor-UniPro-ACCTCATGGAGTCTGAGACCuGAGGC-x | 109 |
| GYG-2793-1 | UniFor-UniPro-GCCCTGGTCCTGGGAuCATCA-x | 110 |
| GYG-2793-2 | UniFor-UniPro-CTGTGCTGTTTCAGAGATGATCcCAGGT-x | 111 |
| Serpina 79-1 | UniFor-UniPro-CAAGAGTCCTGAGCTGAACCAAgAAGGT-x | 112 |
| Serpina 79-2 | UniFor-UniPro-CGACCCCCTCCTCCTTCTTgGTTCT-x | 113 |
| Myc 538-1 | UniFor-UniPro-CTGCTTAGACGCTGGATTTTTuCGGGA-x | 114 |
| Myc 538-2 | UniFor-UniPro-CTGGTTTTCCACTACCCGAAArAAAAA-x | 115 |
| GYG-2744-1 | UniFor-UniPro-CTTTGTATTAAGATCAGGCCTTTGTgACACA-x | 116 |
| GYG-2744-2 | UniFor-UniPro-CATCGTTTGTGGTTAGTGTCACaAAGGG-x | 117 |
| RNase P For | GCGGAGGGAAGCTCATCAG | 118 |
| RNase P Rev | CCCTAGTCTCAGACCTTCCCAA | 119 |
| RNase P probe | FAM-CCACGAGCTGAGTGCGTCCTGTCA-IBFQ | 120 |

DNA is uppercase, RNA is lowercase.
FAM = 6-Fluorescein fluorescent dye (IDT, Coralville, IA).
IBFQ = Iowa Black™ fluorescent quencher (IDT, Coralville, IA).
UniFor-UniPro = universal forward primer, and universal probe binding site.
X = propanediol (C3) spacer blocking group.

TABLE 2

Non-discriminatory reverse primers utilized in Example 1.

| Name | Sequence | Seq ID No. |
|---|---|---|
| GCK-356-1 | GAGGAAACTGTGACTGAACCTC | 121 |
| GCK-356-2 | CCAAGGCTTCTCCGCC | 122 |
| ERBB3-33-1 | GAGTCCGGGGAGGGATG | 123 |
| ERBB3-33-2 | CAATCCCTACTCCAGCCTC | 124 |
| TTR-1257-1 | ATGTGAGCCTCTCTCTACCAA | 125 |
| TTR-1257-2 | GTCCTCTGATGGTCAAAGTTCTA | 126 |

TABLE 2-continued

Non-discriminatory reverse primers utilized in Example 1.

| Name | Sequence | Seq ID No. |
|---|---|---|
| HAMP-253-1 | CACTGGTCAGGCTGGC | 127 |
| HAMP-253-2 | CAAGCTCAAGACCCAGCA | 128 |
| BIRC5-606-1 | CAACTCAAATCTTTTGACAACTCAG | 129 |
| BIRC5-606-2 | GGAGCTGGAAGGCTGG | 130 |
| SAA 146-1 | TTCAGAATGGTATGGCTGTATGC | 131 |
| SAA 146-2 | CACAGATCAGGTGAGGAGCA | 132 |
| IDO1-97-1 | GTTTTCCATAGCGTGTGCC | 133 |
| IDO1-97-2 | GTGGTCACTGGCTGTGG | 134 |
| IDO1-176-1 | TTCCCACATTTTACTGCCTTCTC | 135 |
| IDO1-176-2 | CGCTATGGAAAACTCCTGGA | 136 |
| CYP27A-31016-1 | CAGGTCTGTGCATCAGCG | 137 |
| CYP27A-31016-2 | CTTTCTGGAAGCGATACCTG | 138 |
| SAA 226-1 | CGCACAGAACTCAACATGGG | 139 |
| SAA 226-2 | AATAGTTATCCTGGGGCATACAGC | 140 |
| KIF11-369-1 | GCTCGGAATCCTGTCAGC | 141 |
| KIF11-369-2 | CAGCCAAATTCGTCTGCG | 142 |
| C3-1394-1 | GGGATGTTCCAGTCACTGTTAC | 143 |
| C3-1394-2 | GGTTGGTGGCAGGGG | 144 |
| HOGA-505-1 | AGGGGAAGGTGCCCAG | 145 |
| HOGA-505-2 | AAGGTGGACATTGCGGG | 146 |
| EGFR-123344-1 | TCATAATTCCTCTGCACATAGGT | 147 |
| EGFR-123344-2 | GCCAAGGCACGAGTAACA | 148 |
| ALDH2-15144-1 | CGTATAAAATAGAAGACGAATCCATCCC | 149 |
| ALDH2-15144-2 | ATGGCACGATGCCGT | 150 |
| AGXT-140-1 | GGCTTGAGCAGGGCC | 151 |
| AGXT-140-2 | TGGCCAAGGCCAGTG | 152 |
| APOC-2929-1 | TCAGGCAGCCACGGC | 153 |
| APOC-2929-2 | GTGACCGATGGCTTCAGT | 154 |
| Met 27554-1 | CATACGCAGCCTGAAGTATATTAAACA | 155 |
| Met 27554-2 | TAGATGCTCAGACTTTTCACACAAGA | 156 |
| SAA 88-1 | TTCAGAATGGTATGGCTGTATGC | 157 |
| SAA 88-2 | AGCAGGGAAGGCTCAGTATAAATAG | 158 |
| HIF1A-293-1 | TAAGCGCTGGCTCCCT | 159 |
| HIF1A-293-2 | CTCTAGTCTCACGAGGGGTT | 160 |
| Met 27475-1 | CTCTTTTCTGTGAGAATACACTCCAG | 161 |
| Met 27475-2 | TACCCCATTAAGTATGTCCATGCC | 162 |
| HAMP-295-1 | TCTCCCATCCCTGCTGC | 163 |
| HAMP-295-2 | CCGCTTGCCTCCTGC | 164 |
| GRHPR-2234-1 | CACCCAGTGTGCACCT | 165 |
| GRHPR-2234-2 | GCCAAGGAGCTAGAGCGA | 166 |
| HAMP-88-1 | GAGGCGGTGGTCTGAG | 167 |
| HAMP-88-2 | TGTTCCCTGTCGCTCTG | 168 |
| Met 27254-1 | CTTTAGCCTTCTCACTGATATCGAATG | 169 |
| Met 27254-2 | GCATATTCTCCCCACAGATAGAAGA | 170 |
| GRHPR-2264-1 | CCTGCCCACCCAGTG | 171 |
| GRHPR-2264-2 | CTGTGAGGTGGAGCAGTG | 172 |
| Serpina 279-1 | TAGCTCCTGGGCATTTCTTCC | 173 |
| Serpina 279-2 | AGCTTGAGGAGAGCAGGAAAG | 174 |
| Myc 459-1 | CCTGGTTTTCCACTACCCGA | 175 |
| Myc 459-2 | CACTGGAACTTACAACACCCG | 176 |
| Serpina 130-1 | TTCCTGCTCTCCTCAAGCTCT | 177 |
| Serpina 130-2 | GAGCTGAACCAAGAAGGAGGA | 178 |
| Myc 490-1 | AGGCATTCGACTCATCTCAGC | 179 |
| Myc 490-2 | TGCACTGGAACTTACAACACC | 180 |
| GRHPR-2179-1 | TCGGAGAGGAGGCAGAG | 181 |
| GRHPR-2179-2 | TTCTCCTGAGGGCCTCC | 182 |
| GYG-2851-1 | ACAGGGAGAAGGATGTCAGAG | 183 |
| GYG-2851-2 | GTCCTGGGATCATCTCTGAAAC | 184 |
| GYG-2793-1 | ACAGGGAGAAGGATGTCAGAG | 185 |
| GYG-2793-2 | CACTAACCACAAACGATGCCT | 186 |
| Serpina 79-1 | GAATTCCTGGCAGCAGCA | 187 |
| Serpina 79-2 | CTACTGCCTCCACCCGAA | 188 |
| Myc 538-1 | TAGGCATTCGACTCATCTCAGC | 189 |
| Myc 538-2 | TGCACTGGAACTTACAACACC | 190 |
| GYG-2744-1 | GGACCAGGGCACCTTTG | 191 |
| GYG-2744-2 | GGCTTTCTCCAGATAAGATACTG | 192 |

DNA is uppercase.

Although the reverse primers were not cleaved by RNase H2 in these assays, the results suggest that blocked-cleavable reverse primers could also be utilized in these assays.

Analysis of the amplification data was performed using a ΔΔCq method. Briefly, the ΔCq was calculated between each of the target Cqs and the corresponding reference (RNase P) Cqs. A conversion was then done with the calculated ΔCq, where ΔCq experimental was calculated as being equal to $2^{-\Delta Cq}$. ΔΔCq was then calculated by normalization against the ΔCq calculated from the WT (un-mutated) control.

Figure 13A:
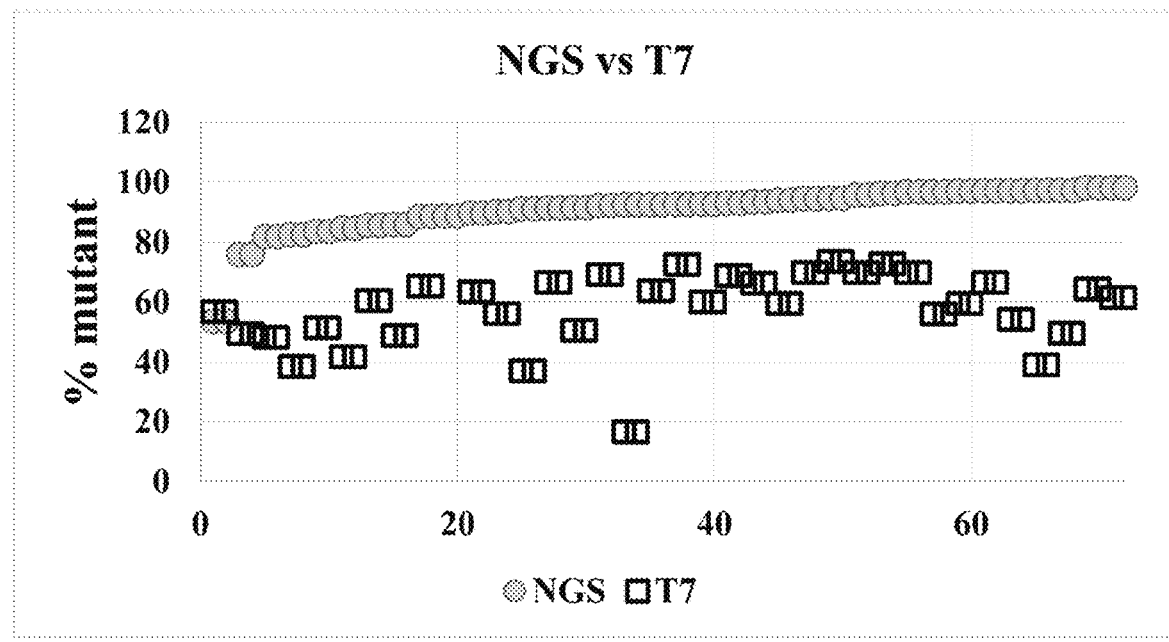
FIGS. 13A-13B show analysis of CRISPR mutations demonstrating that the results obtained using the qPCR methods of the disclosure are more accurate than using the T7EI EMCA method.
Figure 13B:
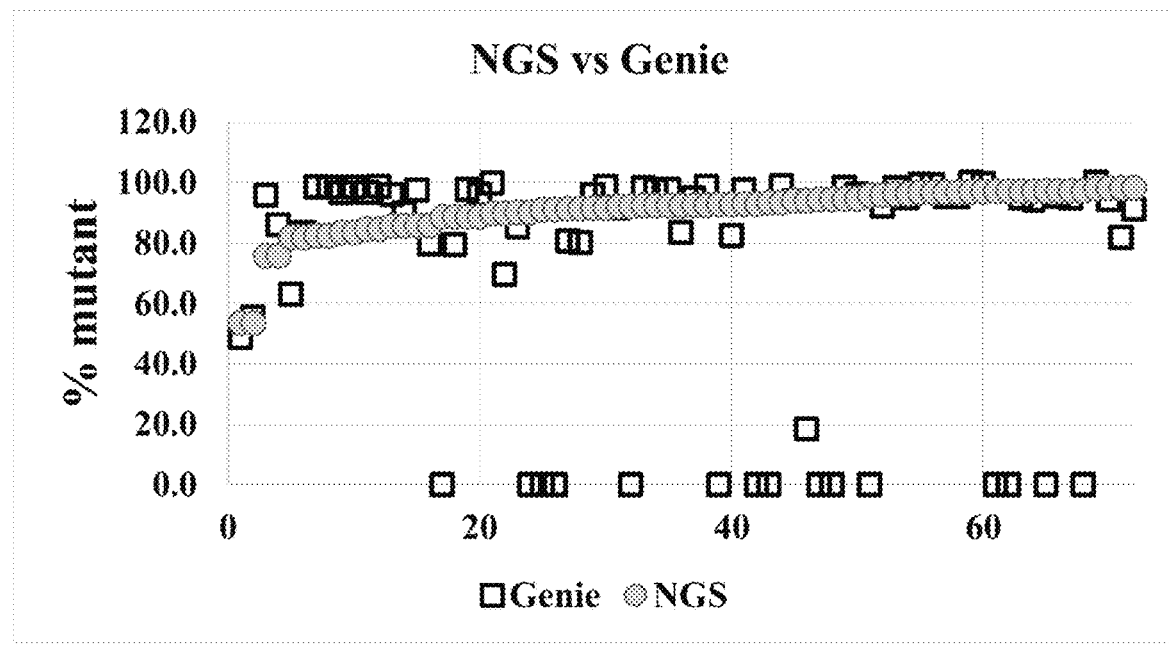

Experimental results are shown in FIGS. 13A and 13B. FIG. 13A shows the clear difference between the NGS and T7 endonuclease cleavage data. Of the 72 assays tested, 64 of the T7EI results were >25% discordant in their quantification of the amount of mutant template present compared to the NGS gold standard. The error in T7EI quantification is expected as EMCA assays usually underestimate genome editing rates, as discussed above.

FIG. 13B shows the comparison between the NGS data and the method of the present invention. A total of 74 assays were tested in the new assay format. Of these, 13 failed to amplify (17%), of which 10/13 (76%) of the failed assays showed sequence features that impair primer function and could easily be removed from future testing by a design algorithm (G-quadraplexes, hairpins, etc.). Of the 61/74 assays that amplified, only 2/61 (3.3%) showed more than 25% divergence from the results obtained with the NGS experiment. These data, combined with the data from FIG. 13A, demonstrate the utility of the assays of the disclosure in providing a rapid, inexpensive PCR-based method to detect CRISPR genome mutation events and how the accuracy of this method is much superior to EMCA assays.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of detecting a variation in a target DNA sequence comprising:
   (a) providing a reaction mixture comprising:
      (i) an oligonucleotide primer having a cleavage domain positioned 5' of a blocking group and 3' of a position of variation, the blocking group linked at or near the end of the 3'-end of the oligonucleotide primer wherein the blocking group prevents primer extension and/or inhibits the oligonucleotide primer from serving as a template for DNA synthesis;
      (ii) a sample nucleic acid comprising the target DNA sequence, wherein the target DNA sequence has been altered with a gene editing enzyme, and wherein the target DNA sequence may or may not have the variation;
      (iii) a cleaving enzyme; and
      (iv) a polymerase, wherein the polymerase is a high-discrimination polymerase;
   (b) hybridizing the oligonucleotide primer to the target DNA sequence to form a double-stranded substrate;
   (c) cleaving the oligonucleotide primer hybridized to the target DNA sequence, if the oligonucleotide primer is complementary at the variation, with the cleaving enzyme at a point within or adjacent to the cleavage domain to remove the blocking group from the oligonucleotide primer; and
   (d) extending the oligonucleotide primer with the polymerase.

2. The method of claim 1, wherein the target DNA sequence has been altered with a CRISPR enzyme.

3. The method of claim 1, wherein the target DNA sequence has been altered with a Cas9 or Cpf1 enzyme.

4. The method of claim 1, wherein the cleaving enzyme is a hot start cleaving enzyme which is thermostable and has reduced activity at lower temperatures.

5. The method of claim 1, wherein the cleaving enzyme is an RNase H2 enzyme.

6. The method of claim 5, wherein the cleaving enzyme is *Pyrococcus abyssi* RNase H2 enzyme.

7. The method of claim 1, wherein the cleaving enzyme is a chemically modified hot start cleaving enzyme which is thermostable and has reduced activity at lower temperatures.

8. The method of claim 7, wherein the hot start cleaving enzyme is a chemically modified *Pyrococcus abyssi* RNase H2.

9. The method of claim 1, wherein the cleaving enzyme is a hot start cleaving enzyme that is reversibly inactivated through interaction with an antibody at lower temperatures.

10. The method of claim 1, wherein the cleavage domain comprises at least one RNA base, and the cleaving enzyme cleaves between the position complementary to the variation and the RNA base.

11. The method of claim 10, wherein the cleavage domain comprises (a) at least one RNA base located 3' of the position of variation and (b) one DNA base between the position of variation and the RNA base.

12. The method of claim 1, wherein the cleavage domain comprises one or more 2'-modified nucleosides, and the cleaving enzyme cleaves between the position complementary to the variation and the one or more modified nucleosides.

13. The method of claim 12, wherein the one or more modified nucleosides are 2'-fluoronucleosides.

14. The method of claim 1, wherein the polymerase is a mutant H784Q Taq polymerase.

15. The method of claim 14, wherein the mutant H784Q Taq polymerase is reversibly inactivated via chemical, aptamer, or antibody modification.

16. The method of claim 1, wherein the oligonucleotide primer contains a 5' tail sequence that comprises a universal primer sequence and optionally a universal probe sequence, wherein the tail is non-complementary to the target DNA sequence.

17. The method of claim 1 further comprising:
(e) detecting an internal control gene not targeted by the gene editing enzyme; and
(f) normalizing the results of steps (a)-(d) to the results of step (e).

18. The method of claim 17, wherein the internal control gene not targeted by the gene editing enzyme is the RNase P gene.

19. The method of claim 17, wherein the reaction mixture further comprises a control oligonucleotide primer specific for the internal control gene not targeted by the gene editing enzyme, wherein the control oligonucleotide primer comprises a cleavage domain positioned 5' of a blocking group and 3' of a position of variation, the blocking group linked at or near the end of the 3'-end of the control oligonucleotide primer wherein the blocking group prevents primer extension and/or inhibits the control oligonucleotide primer from serving as a template for DNA synthesis.

20. The method of claim 17, wherein the internal control gene not targeted by the gene editing enzyme is detected using a three-oligonucleotide 5' nuclease assay.

21. A method of target enrichment comprising:
(a) providing a reaction mixture comprising:
(i) a first oligonucleotide primer having a tail domain that is not complementary to a target DNA sequence, the tail domain comprising a first universal primer sequence; a cleavage domain positioned 5' of a blocking group and 3' of a position of variation, the blocking group linked at or near the end of the 3'-end of the first oligonucleotide primer wherein the blocking group prevents primer extension and/or inhibits the first oligonucleotide primer from serving as a template for DNA synthesis;
(ii) a sample nucleic acid comprising the target DNA sequence, wherein the target DNA sequence has been altered with a gene editing enzyme;
(iii) a cleaving enzyme; and
(iv) a polymerase, wherein the polymerase is a high-discrimination polymerase;
(b) hybridizing the first oligonucleotide primer to the target DNA sequence to form a double-stranded substrate;
(c) cleaving the first oligonucleotide primer hybridized to the target DNA sequence, if the first oligonucleotide primer is complementary to the target DNA sequence, with the cleaving enzyme at a point within or adjacent to the cleavage domain to remove the blocking group from the first oligonucleotide primer; and
(d) extending the first oligonucleotide primer with the polymerase.

22. The method of claim 21, wherein the target DNA sequence has been altered with a CRISPR enzyme.

23. The method of claim 21, wherein the target DNA sequence has been altered with a Cas9 or Cpf1 enzyme.

24. The method of claim 21, the method further comprising a second oligonucleotide primer in reverse orientation to support priming and extension of the first oligonucleotide primer extension product.

25. The method of claim 24, wherein the second oligonucleotide primer further comprises a tail domain comprising a second universal primer sequence.

26. The method of claim 25, wherein steps (b)-(d) are performed 1-10 times.

27. The method of claim 26, further comprising removing unextended primers from the reaction and hybridizing universal primers to the extension product to form a second extension product.

28. The method of claim 27, wherein the universal primers further comprise tailed sequences for addition of adapter sequences to the second extension product.

29. The method of claim 28, wherein sequencing is performed on the second extension product to determine the sequence of the target.

30. The method of claim 21, wherein the cleaving enzyme is a hot start cleaving enzyme which is thermostable and has reduced activity at lower temperatures.

31. The method of claim 30, wherein the cleaving enzyme is an RNase H2 enzyme.

32. The method of claim 31, wherein the cleaving enzyme is *Pyrococcus abyssi* RNase H2 enzyme.

33. The method of claim 21, wherein the cleaving enzyme is a chemically modified hot start cleaving enzyme which is thermostable and has reduced activity at lower temperatures.

34. The method of claim 21, wherein the hot start cleaving enzyme is a chemically modified *Pyrococcus abyssi* RNase H2.

35. The method of claim 21, wherein the cleaving enzyme is a hot start cleaving enzyme that is reversibly inactivated through interaction with an antibody at lower temperatures which is thermostable and has reduced activity at lower temperatures.

36. The method of claim 21, wherein the cleavage domain comprises at least one RNA base, and the cleaving enzyme cleaves between the position complementary to the variation and the RNA base.

37. The method of claim 36, wherein the cleavage domain comprises (a) at least one RNA base located 3' of the position of variation and (b) one DNA base between the position of variation and the RNA base.

38. The method of claim 21, wherein the cleavage domain comprises one or more 2'-modified nucleosides, and the cleaving enzyme cleaves between the position complementary to the variation and the one or more modified nucleosides.

39. The method of claim 38, wherein the one or more modified nucleosides are 2'-fluoronucleosides.

40. The method of claim 21, wherein the polymerase is a mutant H784Q Taq polymerase.

41. The method of claim 40, wherein the mutant H784Q Taq polymerase is reversibly inactivated via chemical, aptamer or antibody modification.

* * * * *

SEQUENCE LISTING

```
<160> NUMBER OF SEQ ID NOS: 192

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
gctgtgattt tggtctagct acag                                                24

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
gctgtgattt tggtctagct acagt                                               25

<210> SEQ ID NO 3
<211> LENGTH: 25
<212> TYPE: DNA
<213> ORGANISM: Artificial Sequence
<220> FEATURE:
<223> OTHER INFORMATION: Synthetic
```

<400> SEQUENCE: 3
gctgtgattt tggtctagct acaga                                          25

<210> SEQ ID NO 4
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' 6-carboxyfluorescein
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (27)..(27)
<223> OTHER INFORMATION: 3' Iowa Black fluorescence quencher

<400> SEQUENCE: 4
tcccatcagt ttgaacagtt gtctgga                                        27

<210> SEQ ID NO 5
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: RNA
<220> FEATURE:
<221> NAME/KEY: misc_feature
<222> LOCATION: (31)..(31)
<223> OTHER INFORMATION: 3' C3 propanediol spacer block

<400> SEQUENCE: 5
gctgtgattt tggtctagct acagtgaaat g                                   31

<210> SEQ ID NO 6
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: RNA
<220> FEATURE:
<221> NAME/KEY: misc_feature
<222> LOCATION: (31)..(31)
<223> OTHER INFORMATION: 3' C3 propanediol spacer block

<400> SEQUENCE: 6
gctgtgattt tggtctagct acagagaaat g                                   31

<210> SEQ ID NO 7
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)

```
<223> OTHER INFORMATION: RNA
<220> FEATURE:
<221> NAME/KEY: misc_feature
<222> LOCATION: (31)..(31)
<223> OTHER INFORMATION: 3' C3 propanediol spacer block

<400> SEQUENCE: 7
gccctcaatt cttaccatcc acaaaatgga a                              31

<210> SEQ ID NO 8
<211> LENGTH: 401
<212> TYPE: DNA
<213> ORGANISM: Artificial Sequence
<220> FEATURE:
<223> OTHER INFORMATION: Synthetic

<400> SEQUENCE: 8
aaaaaataag aacactgatt tttgtgaata ctgggaacta tgaaaatact atagttgaga    60
ccttcaatga ctttctagta actcagcagc atctcagggc caaaaattta atcagtggaa   120
aaatagcctc aattcttacc atccacaaaa tggatccaga caactgttca aactgatggg   180
acccactcca tcgagatttc actgtagcta gaccaaaatc acctattttt actgtgaggt   240
cttcatgaag aaatatatct gaggtgtagt aagtaaagga aaacagtaga tctcattttc   300
ctatcagagc aagcattatg aagagtttag gtaagagatc taatttctat aattctgtaa   360
tataatattc tttaaaacat agtacttcat ctttcctctt a                      401

<210> SEQ ID NO 9
<211> LENGTH: 401
<212> TYPE: DNA
<213> ORGANISM: Artificial Sequence
<220> FEATURE:
<223> OTHER INFORMATION: Synthetic

<400> SEQUENCE: 9
aaaaaataag aacactgatt tttgtgaata ctgggaacta tgaaaatact atagttgaga    60
ccttcaatga ctttctagta actcagcagc atctcagggc caaaaattta atcagtggaa   120
aaatagcctc aattcttacc atccacaaaa tggatccaga caactgttca aactgatggg   180
acccactcca tcgagatttc tctgtagcta gaccaaaatc acctattttt actgtgaggt   240
cttcatgaag aaatatatct gaggtgtagt aagtaaagga aaacagtaga tctcattttc   300
ctatcagagc aagcattatg aagagtttag gtaagagatc taatttctat aattctgtaa   360
tataatattc tttaaaacat agtacttcat ctttcctctt a                      401

<210> SEQ ID NO 10
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: RNA
<220> FEATURE:
<221> NAME/KEY: misc_feature
<222> LOCATION: (27)..(28)
<223> OTHER INFORMATION: two C3 propanediol spacers

<400> SEQUENCE: 10
gctgtgattt tggtctagct acagtgatg                                    29
```

-continued

```
<210> SEQ ID NO 11
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: RNA
<220> FEATURE:
<221> NAME/KEY: misc_feature
<222> LOCATION: (27)..(28)
<223> OTHER INFORMATION: two C3 propanediol spacers

<400> SEQUENCE: 11
gctgtgattt tggtctagct acagagatg                                    29

<210> SEQ ID NO 12
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: RNA
<220> FEATURE:
<221> NAME/KEY: misc_feature
<222> LOCATION: (31)..(31)
<223> OTHER INFORMATION: 3' C3 propanediol spacer

<400> SEQUENCE: 12
gccctcaatt cttaccatcc acaaaatgga a                                 31

<210> SEQ ID NO 13
<211> LENGTH: 23
<212> TYPE: DNA
<213> ORGANISM: Artificial Sequence
<220> FEATURE:
<223> OTHER INFORMATION: Synthetic

<400> SEQUENCE: 13
cgccgcgtat agtcccgcgt aaa                                          23

<210> SEQ ID NO 14
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' 6-carboxyfluorescein
<220> FEATURE:
<221> NAME/KEY: misc_feature
<222> LOCATION: (1)..(1)
<223> OTHER INFORMATION: LNA residue
<220> FEATURE:
<221> NAME/KEY: misc_feature
<222> LOCATION: (5)..(7)
<223> OTHER INFORMATION: LNA residues
<220> FEATURE:
<221> NAME/KEY: misc_feature
<222> LOCATION: (11)..(11)
<223> OTHER INFORMATION: LNA residue
<220> FEATURE:
<221> NAME/KEY: misc_feature
<222> LOCATION: (13)..(13)
<223> OTHER INFORMATION: 3' Iowa Black fluorescence quencher
```

```
<400> SEQUENCE: 14
ccatcaccgt gct                                                         13

<210> SEQ ID NO 15
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'
      6-carboxy-2',4,4',5',7,7'-hexachlorofluorescein
<220> FEATURE:
<221> NAME/KEY: misc_feature
<222> LOCATION: (5)..(7)
<223> OTHER INFORMATION: LNA residues
<220> FEATURE:
<221> NAME/KEY: misc_feature
<222> LOCATION: (11)..(11)
<223> OTHER INFORMATION: LNA residue
<220> FEATURE:
<221> NAME/KEY: misc_feature
<222> LOCATION: (13)..(13)
<223> OTHER INFORMATION: 3' Iowa Black fluorescence quencher

<400> SEQUENCE: 15
caatccccga gct                                                         13

<210> SEQ ID NO 16
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (48)..(48)
<223> OTHER INFORMATION: RNA
<220> FEATURE:
<221> NAME/KEY: misc_feature
<222> LOCATION: (53)..(53)
<223> OTHER INFORMATION: 3' C3 propanediol spacer block

<400> SEQUENCE: 16
gcccatgtcc cagcgaacca tcaccgtgct agccctcgat acagcccggc cac              53

<210> SEQ ID NO 17
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (46)..(46)
<223> OTHER INFORMATION: RNA
<220> FEATURE:
<221> NAME/KEY: misc_feature
<222> LOCATION: (52)..(52)
<223> OTHER INFORMATION: 3' C3 propanediol spacer block

<400> SEQUENCE: 17
gcccatgtcc cagcgaacaa tccccgagct gccctcgata cagcctggcc ac               52

<210> SEQ ID NO 18
<211> LENGTH: 26
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (21)..(21)
<223> OTHER INFORMATION: RNA
<220> FEATURE:
<221> NAME/KEY: misc_feature
<222> LOCATION: (26)..(26)
<223> OTHER INFORMATION: 3' C3 propanediol spacer block

<400> SEQUENCE: 18
gcggccaggt atacggacat catcca                                          26

<210> SEQ ID NO 19
<211> LENGTH: 401
<212> TYPE: DNA
<213> ORGANISM: Artificial Sequence
<220> FEATURE:
<223> OTHER INFORMATION: Synthetic

<400> SEQUENCE: 19
gttgggagct gggagggact gagttagggt gcacggggcg gccagtctca ccactgacca      60
gtttgtctgt ctgtgtgtgt ccatgtgcga gggcagagga ggaccccaca tggaccgcag     120
cagcgcccga ggccaggtat acggacatca tcctgtacgc gtcgggctcc ctggccttgg     180
ctgtgctcct gctgctggcc gggctgtatc gagggcaggc gctccacggc cggcaccccc     240
gcccgcccgc cactgtgcag aagctctccc gcttccctct ggcccgacag gtactgggcg     300
catcccccac ctcacatgtg acagcctgac tccagcaggc agaaccaagt ctcccacttt     360
gcagttctcc ctggagtcag gctcttccgg caagtcaagc t                         401

<210> SEQ ID NO 20
<211> LENGTH: 401
<212> TYPE: DNA
<213> ORGANISM: Artificial Sequence
<220> FEATURE:
<223> OTHER INFORMATION: Synthetic

<400> SEQUENCE: 20
gttgggagct gggagggact gagttagggt gcacggggcg gccagtctca ccactgacca      60
gtttgtctgt ctgtgtgtgt ccatgtgcga gggcagagga ggaccccaca tggaccgcag     120
cagcgcccga ggccaggtat acggacatca tcctgtacgc gtcgggctcc ctggccttgg     180
ctgtgctcct gctgctggcc aggctgtatc gagggcaggc gctccacggc cggcaccccc     240
gcccgcccgc cactgtgcag aagctctccc gcttccctct ggcccgacag gtactgggcg     300
catcccccac ctcacatgtg acagcctgac tccagcaggc agaaccaagt ctcccacttt     360
gcagttctcc ctggagtcag gctcttccgg caagtcaagc t                         401

<210> SEQ ID NO 21
<211> LENGTH: 19
<212> TYPE: DNA
<213> ORGANISM: Artificial Sequence
<220> FEATURE:
<223> OTHER INFORMATION: Synthetic

<400> SEQUENCE: 21
cggcccatgt cccagcgaa                                                   19

<210> SEQ ID NO 22
<211> LENGTH: 13
<212> TYPE: DNA
<213> ORGANISM: Artificial Sequence
```

<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' Yakima yellow
<220> FEATURE:
<221> NAME/KEY: misc_feature
<222> LOCATION: (1)..(1)
<223> OTHER INFORMATION: LNA residue
<220> FEATURE:
<221> NAME/KEY: misc_feature
<222> LOCATION: (5)..(7)
<223> OTHER INFORMATION: LNA residues
<220> FEATURE:
<221> NAME/KEY: misc_feature
<222> LOCATION: (11)..(11)
<223> OTHER INFORMATION: LNA residue
<220> FEATURE:
<221> NAME/KEY: misc_feature
<222> LOCATION: (13)..(13)
<223> OTHER INFORMATION: 3' Iowa Black fluorescence quencher

<400> SEQUENCE: 22
caatccccga gct                                                          13

<210> SEQ ID NO 23
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (51)..(51)
<223> OTHER INFORMATION: RNA
<220> FEATURE:
<221> NAME/KEY: misc_feature
<222> LOCATION: (56)..(56)
<223> OTHER INFORMATION: 3' C3 propanediol spacer block

<400> SEQUENCE: 23
gcccatgtcc cagcgaacca tcaccgtgct acttcccaca ccctcatatc utgtta           56

<210> SEQ ID NO 24
<211> LENGTH: 59
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (54)..(54)
<223> OTHER INFORMATION: RNA
<220> FEATURE:
<221> NAME/KEY: misc_feature
<222> LOCATION: (59)..(59)
<223> OTHER INFORMATION: 3' C3 propanediol spacer block

<400> SEQUENCE: 24
gcccatgtcc cagcgaacaa tccccgagct cttacttccc acaccctcat atautgtta        59

<210> SEQ ID NO 25
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(27)
<223> OTHER INFORMATION: RNA
<220> FEATURE:

```
<221> NAME/KEY: misc_feature
<222> LOCATION: (32)..(32)
<223> OTHER INFORMATION: 3' C3 propanediol spacer block

<400> SEQUENCE: 25
gcgctaagta aacattcctg attgcaactt at                                    32

<210> SEQ ID NO 26
<211> LENGTH: 490
<212> TYPE: DNA
<213> ORGANISM: Artificial Sequence
<220> FEATURE:
<223> OTHER INFORMATION: Synthetic

<400> SEQUENCE: 26 gattttttt ttttggcatt tcttcttaga tttctatctc ctaacatagg atcacttatt       60
tgtgaaatta tttgtatacc ttttttatgg agtgatgatg tgatacaaat tctatcctta    120
aggatataag aacatctttt ctttatatta ggattttcct ggacccatga gttacatgct    180
tacttcccac accctcatat cttgtttaaa tttgtagaat taaattcata ggtaattatt    240
tctgaaactt cttccctgtg tgagcaatct aaataattat tacaatgcct taagttgcaa    300
tcaggaatgt ttacttagca cagacttttt tccccactac tgcactcaaa ggataacaga    360
tatatggcaa atctaaccat attctttgtc ctttgtccat gttgcggagg aagctcatc     420 agtggggcca cgagctgagt gcgtcctgtc actccactcc catgtccctt gggaaggtct    480
gagactaggg                                                            490

<210> SEQ ID NO 27
<211> LENGTH: 490
<212> TYPE: DNA
<213> ORGANISM: Artificial Sequence
<220> FEATURE:
<223> OTHER INFORMATION: Synthetic

<400> SEQUENCE: 27 gattttttt ttttggcatt tcttcttaga tttctatctc ctaacatagg atcacttatt       60
tgtgaaatta tttgtatacc ttttttatgg agtgatgatg tgatacaaat tctatcctta    120
aggatataag aacatctttt ctttatatta ggattttcct ggacccatga gttacatgct    180
tacttcccac accctcatat attgtttaaa tttgtagaat taaattcata ggtaattatt    240
tctgaaactt cttccctgtg tgagcaatct aaataattat tacaatgcct taagttgcaa    300
tcaggaatgt ttacttagca cagacttttt tccccactac tgcactcaaa ggataacaga    360
tatatggcaa atctaaccat attctttgtc ctttgtccat gttgcggagg aagctcatc     420 agtggggcca cgagctgagt gcgtcctgtc actccactcc catgtccctt gggaaggtct    480
gagactaggg                                                            490

<210> SEQ ID NO 28
<211> LENGTH: 59
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (54)..(54)
<223> OTHER INFORMATION: RNA
<220> FEATURE:
<221> NAME/KEY: misc_feature
<222> LOCATION: (59)..(59)
<223> OTHER INFORMATION: 3' C3 propanediol spacer block
```

<400> SEQUENCE: 28
gcccatgtcc cagcgaacca tcaccgtgct ttctcttctg gactccctat aatattgtg        59

<210> SEQ ID NO 29
<211> LENGTH: 59
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (54)..(54)
<223> OTHER INFORMATION: RNA
<220> FEATURE:
<221> NAME/KEY: misc_feature
<222> LOCATION: (59)..(59)
<223> OTHER INFORMATION: 3' C3 propanediol spacer block

<400> SEQUENCE: 29
gcccatgtcc cagcgaacaa tccccgagct ttctcttctg gactccctat aacattgtg        59

<210> SEQ ID NO 30
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: RNA
<220> FEATURE:
<221> NAME/KEY: misc_feature
<222> LOCATION: (26)..(26)
<223> OTHER INFORMATION: 3' C3 propanediol spacer block

<400> SEQUENCE: 30
gcggattgat gcagcagtga gtcatg        26

<210> SEQ ID NO 31
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (51)..(51)
<223> OTHER INFORMATION: RNA
<220> FEATURE:
<221> NAME/KEY: misc_feature
<222> LOCATION: (56)..(56)
<223> OTHER INFORMATION: 3' C3 propanediol spacer block

<400> SEQUENCE: 31
gcccatgtcc cagcgaacca tcaccgtgct ctccgttgtt ttccagaaac gatttc        56

<210> SEQ ID NO 32
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (51)..(51)
<223> OTHER INFORMATION: RNA
<220> FEATURE:
<221> NAME/KEY: misc_feature
<222> LOCATION: (56)..(56)

<223> OTHER INFORMATION: 3' C3 propanediol spacer block

<400> SEQUENCE: 32
gcccatgtcc cagcgaacaa tccccgagct ctccgttgtt ttccagaaat gatttc    56

<210> SEQ ID NO 33
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (51)..(51)
<223> OTHER INFORMATION: RNA
<220> FEATURE:
<221> NAME/KEY: misc_feature
<222> LOCATION: (56)..(56)
<223> OTHER INFORMATION: 3' C3 propanediol spacer block

<400> SEQUENCE: 33
gcccatgtcc cagcgaacaa tccccgagct ctccgttgtt ttccagaaag gatttc    56

<210> SEQ ID NO 34
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: RNA
<220> FEATURE:
<221> NAME/KEY: misc_feature
<222> LOCATION: (28)..(28)
<223> OTHER INFORMATION: 3' C3 propanediol spacer block

<400> SEQUENCE: 34
gcaaccaagt cttccctaca accttgat                                   28

<210> SEQ ID NO 35
<211> LENGTH: 401
<212> TYPE: DNA
<213> ORGANISM: Artificial Sequence
<220> FEATURE:
<223> OTHER INFORMATION: Synthetic

<400> SEQUENCE: 35
acatcatttt tattgtataa aagcatttta gtatcaattt tctcattttt aaaccaagtc    60
ttccctacaa ccttgaataa atggtttcca aggaaaataa aatcttggcc ttacctggat   120
ccatggggag ttcagaatcc tgaagttttc attgaatctt ttcatcaggg tgagaaaatt   180 ctgatctttta taatcaaatc gtttctggaa acaacggag cagatcacat tgcagggagc    240
acagcccagg atgaaagtgg gatcacaggg tgaagctaaa gatttaaaaa tttttaaaaa   300
aattattaaa aaataaatat ttaaaagatt tgcatttgtt aagacataaa ggaaatttag   360 aaatttttaaa caatatctta caaattcccc atgtgtccaa a                     401

<210> SEQ ID NO 36
<211> LENGTH: 401
<212> TYPE: DNA
<213> ORGANISM: Artificial Sequence
<220> FEATURE:
<223> OTHER INFORMATION: Synthetic

<400> SEQUENCE: 36

```
acatcatttt tattgtataa aagcatttta gtatcaattt tctcattttt aaaccaagtc    60
ttccctacaa ccttgaataa atggtttcca aggaaaataa atcttggcc ttacctggat    120 ccatggggag ttcagaatcc tgaagttttc attgaatctt tcatcaggg tgagaaaatt    180 ctgatcttta taatcaaatc atttctggaa acaacggag cagatcacat tgcagggagc    240
acagcccagg atgaaagtgg gatcacaggg tgaagctaaa gatttaaaaa ttttttaaaaa    300 aattattaaa aaataaatat ttaaaagatt tgcatttgtt aagacataaa ggaaatttag    360 aaatttttaaa caatatctta caaattcccc atgtgtccaa a    401
```

<210> SEQ ID NO 37
<211> LENGTH: 401
<212> TYPE: DNA
<213> ORGANISM: Artificial Sequence
<220> FEATURE:
<223> OTHER INFORMATION: Synthetic

<400> SEQUENCE: 37

```
acatcatttt tattgtataa aagcatttta gtatcaattt tctcattttt aaaccaagtc    60
ttccctacaa ccttgaataa atggtttcca aggaaaataa atcttggcc ttacctggat    120 ccatggggag ttcagaatcc tgaagttttc attgaatctt tcatcaggg tgagaaaatt    180 ctgatcttta taatcaaatc ctttctggaa acaacggag cagatcacat tgcagggagc    240
acagcccagg atgaaagtgg gatcacaggg tgaagctaaa gatttaaaaa ttttttaaaaa    300 aattattaaa aaataaatat ttaaaagatt tgcatttgtt aagacataaa ggaaatttag    360 aaatttttaaa caatatctta caaattcccc atgtgtccaa a    401
```

<210> SEQ ID NO 38
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (51)..(51)
<223> OTHER INFORMATION: RNA
<220> FEATURE:
<221> NAME/KEY: misc_feature
<222> LOCATION: (56)..(56)
<223> OTHER INFORMATION: 3' C3 propanediol spacer block

<400> SEQUENCE: 38

```
gcccatgtcc cagcgaacca tcaccgtgct gtctttgctt tcctggtgag cccatg    56
```

<210> SEQ ID NO 39
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(49)
<223> OTHER INFORMATION: RNA
<220> FEATURE:
<221> NAME/KEY: misc_feature
<222> LOCATION: (55)..(55)
<223> OTHER INFORMATION: 3' C3 propanediol spacer block

<400> SEQUENCE: 39

```
gcccatgtcc cagcgaacaa tccccgagct gtctttgctt tcctggtgac ccatg    55
```

<210> SEQ ID NO 40
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(27)
<223> OTHER INFORMATION: RNA
<220> FEATURE:
<221> NAME/KEY: misc_feature
<222> LOCATION: (32)..(32)
<223> OTHER INFORMATION: 3' C3 propanediol spacer block

<400> SEQUENCE: 40
gcgttggaac taccacattg ctttatugta ct                          32

<210> SEQ ID NO 41
<211> LENGTH: 19
<212> TYPE: DNA
<213> ORGANISM: Artificial Sequence
<220> FEATURE:
<223> OTHER INFORMATION: Synthetic

<400> SEQUENCE: 41
gcggagggaa gctcatcag                                         19

<210> SEQ ID NO 42
<211> LENGTH: 22
<212> TYPE: DNA
<213> ORGANISM: Artificial Sequence
<220> FEATURE:
<223> OTHER INFORMATION: Synthetic

<400> SEQUENCE: 42
ccctagtctc agaccttccc aa                                     22

<210> SEQ ID NO 43
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' Yakima yellow
<220> FEATURE:
<221> NAME/KEY: misc_feature
<222> LOCATION: (24)..(24)
<223> OTHER INFORMATION: 3' Iowa Black fluorescence quencher

<400> SEQUENCE: 43
ccacgagctg agtgcgtcct gtca                                   24

<210> SEQ ID NO 44
<211> LENGTH: 50
<212> TYPE: DNA
<213> ORGANISM: Artificial Sequence
<220> FEATURE:
<223> OTHER INFORMATION: Synthetic

<400> SEQUENCE: 44
aatgatacgg cgaccaccga gatctacact ctttccctac acgacgctct       50

<210> SEQ ID NO 45
<211> LENGTH: 55

```
<212> TYPE: DNA
<213> ORGANISM: Artificial Sequence
<220> FEATURE:
<223> OTHER INFORMATION: Synthetic

<400> SEQUENCE: 45
caagcagaag acggcatacg agatggacct atgtgactgg agttcagacg tgtgc        55

<210> SEQ ID NO 46
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5 universal domain (UniFor-UniPro-)
<220> FEATURE:
<221> NAME/KEY: misc_feature
<222> LOCATION: (16)..(16)
<223> OTHER INFORMATION: RNA
<220> FEATURE:
<221> NAME/KEY: misc_feature
<222> LOCATION: (21)..(21)
<223> OTHER INFORMATION: 3' propanediol (C3) spacer blocking group

<400> SEQUENCE: 46
ccctgggtcc ctgggagaat c                                             21

<210> SEQ ID NO 47
<211> LENGTH: 26
<212> TYPE: DNA
<213> ORGANISM: Artificial Sequence
<220> FEATURE:
<223> OTHER INFORMATION: GCK-356-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (21)..(21)
<223> OTHER INFORMATION: RNA
<220> FEATURE:
<221> NAME/KEY: misc_feature
<222> LOCATION: (26)..(26)
<223> OTHER INFORMATION: 3' propanediol (C3) spacer blocking group

<400> SEQUENCE: 47
cgaggagaac cacattctcc cagggt                                        26

<210> SEQ ID NO 48
<211> LENGTH: 18
<212> TYPE: DNA
<213> ORGANISM: Artificial Sequence
<220> FEATURE:
<223> OTHER INFORMATION: ERBB3-33-1
<220> FEATURE:
<221> NAME/KEY: misc_feature
<222> LOCATION: (1)..(1)
<223> OTHER INFORMATION: 5 universal domain (UniFor-UniPro-)
<220> FEATURE:
<221> NAME/KEY: misc_feature
<222> LOCATION: (14)..(14)
<223> OTHER INFORMATION: RNA
<220> FEATURE:
<221> NAME/KEY: misc_feature
<222> LOCATION: (18)..(18)
<223> OTHER INFORMATION: 3' propanediol (C3) spacer blocking group

<400> SEQUENCE: 48
```
gggcggccgt gacucacc                                                    18

<210> SEQ ID NO 49
<211> LENGTH: 24
<212> TYPE: DNA
<213> ORGANISM: Artificial Sequence
<220> FEATURE:
<223> OTHER INFORMATION: ERBB3-33-2
<220> FEATURE:
<221> NAME/KEY: misc_feature
<222> LOCATION: (1)..(1)
<223> OTHER INFORMATION: 5 universal domain (UniFor-UniPro-)
<220> FEATURE:
<221> NAME/KEY: misc_feature
<222> LOCATION: (18)..(18)
<223> OTHER INFORMATION: RNA
<220> FEATURE:
<221> NAME/KEY: misc_feature
<222> LOCATION: (24)..(24)
<223> OTHER INFORMATION: 3' propanediol (C3) spacer blocking group

<400> SEQUENCE: 49
gagggaaggg ggtgagtcac ggcg                                             24

<210> SEQ ID NO 50
<211> LENGTH: 25
<212> TYPE: DNA
<213> ORGANISM: Artificial Sequence
<220> FEATURE:
<223> OTHER INFORMATION: TTR-1257-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (20)..(20)
<223> OTHER INFORMATION: RNA
<220> FEATURE:
<221> NAME/KEY: misc_feature
<222> LOCATION: (25)..(25)
<223> OTHER INFORMATION: 3' propanediol (C3) spacer blocking group

<400> SEQUENCE: 50
cctgggagcc atttgcctcu gggtt                                            25

<210> SEQ ID NO 51
<211> LENGTH: 27
<212> TYPE: DNA
<213> ORGANISM: Artificial Sequence
<220> FEATURE:
<223> OTHER INFORMATION: TTR-1257-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 51
ctttggcaac ttacccagag gcaaatc                                          27

<210> SEQ ID NO 52
<211> LENGTH: 22
<212> TYPE: DNA
<213> ORGANISM: Artificial Sequence

```
<220> FEATURE:
<223> OTHER INFORMATION: HAMP-253-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (17)..(17)
<223> OTHER INFORMATION: RNA
<220> FEATURE:
<221> NAME/KEY: misc_feature
<222> LOCATION: (22)..(22)
<223> OTHER INFORMATION: 3' propanediol (C3) spacer blocking group

<400> SEQUENCE: 52
gcactgagct cccagauctg gc                                          22

<210> SEQ ID NO 53
<211> LENGTH: 22
<212> TYPE: DNA
<213> ORGANISM: Artificial Sequence
<220> FEATURE:
<223> OTHER INFORMATION: HAMP-253-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (17)..(17)
<223> OTHER INFORMATION: RNA
<220> FEATURE:
<221> NAME/KEY: misc_feature
<222> LOCATION: (22)..(22)
<223> OTHER INFORMATION: 3' propanediol (C3) spacer blocking group

<400> SEQUENCE: 53
gcaagcggcc cagatcuggg ac                                          22

<210> SEQ ID NO 54
<211> LENGTH: 27
<212> TYPE: DNA
<213> ORGANISM: Artificial Sequence
<220> FEATURE:
<223> OTHER INFORMATION: BIRC5-606-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 54
gacgacccca tgtaagtctt cuctggg                                     27

<210> SEQ ID NO 55
<211> LENGTH: 23
<212> TYPE: DNA
<213> ORGANISM: Artificial Sequence
<220> FEATURE:
<223> OTHER INFORMATION: BIRC5-606-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
```

<220> FEATURE:
<221> NAME/KEY: misc_feature
<222> LOCATION: (17)..(17)
<223> OTHER INFORMATION: RNA
<220> FEATURE:
<221> NAME/KEY: misc_feature
<222> LOCATION: (23)..(23)
<223> OTHER INFORMATION: 3' propanediol (C3) spacer blocking group

<400> SEQUENCE: 55
cgaggctggc cagagaagac ttt                                        23

<210> SEQ ID NO 56
<211> LENGTH: 36
<212> TYPE: DNA
<213> ORGANISM: Artificial Sequence
<220> FEATURE:
<223> OTHER INFORMATION: SAA 146-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (31)..(31)
<223> OTHER INFORMATION: RNA
<220> FEATURE:
<221> NAME/KEY: misc_feature
<222> LOCATION: (36)..(36)
<223> OTHER INFORMATION: 3' propanediol (C3) spacer blocking group

<400> SEQUENCE: 56
ctttcccaac aagattatca tttcctttaa aaaaat                          36

<210> SEQ ID NO 57
<211> LENGTH: 30
<212> TYPE: DNA
<213> ORGANISM: Artificial Sequence
<220> FEATURE:
<223> OTHER INFORMATION: SAA 146-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (25)..(25)
<223> OTHER INFORMATION: RNA
<220> FEATURE:
<221> NAME/KEY: misc_feature
<222> LOCATION: (30)..(30)
<223> OTHER INFORMATION: 3' propanediol (C3) spacer blocking group

<400> SEQUENCE: 57
cgccccagga taactatttt ttttaaaggt                                 30

<210> SEQ ID NO 58
<211> LENGTH: 23
<212> TYPE: DNA
<213> ORGANISM: Artificial Sequence
<220> FEATURE:
<223> OTHER INFORMATION: IDO1-97-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (18)..(18)
<223> OTHER INFORMATION: RNA
<220> FEATURE:
<221> NAME/KEY: misc_feature
<222> LOCATION: (23)..(23)
<223> OTHER INFORMATION: 3' propanediol (C3) spacer blocking group

<400> SEQUENCE: 58
agacactgag gggcaccaga ggt                                                 23

<210> SEQ ID NO 59
<211> LENGTH: 26
<212> TYPE: DNA
<213> ORGANISM: Artificial Sequence
<220> FEATURE:
<223> OTHER INFORMATION: IDO1-97-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (21)..(21)
<223> OTHER INFORMATION: RNA
<220> FEATURE:
<221> NAME/KEY: misc_feature
<222> LOCATION: (26)..(26)
<223> OTHER INFORMATION: 3' propanediol (C3) spacer blocking group

<400> SEQUENCE: 59
cttgtagtct gctcctctgg ugcccg                                              26

<210> SEQ ID NO 60
<211> LENGTH: 33
<212> TYPE: DNA
<213> ORGANISM: Artificial Sequence
<220> FEATURE:
<223> OTHER INFORMATION: IDO1-176-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (28)..(28)
<223> OTHER INFORMATION: RNA
<220> FEATURE:
<221> NAME/KEY: misc_feature
<222> LOCATION: (33)..(33)
<223> OTHER INFORMATION: 3' propanediol (C3) spacer blocking group

<400> SEQUENCE: 60
agtaaagagt accatattga tgaagaagtg gga                                      33

<210> SEQ ID NO 61
<211> LENGTH: 24
<212> TYPE: DNA
<213> ORGANISM: Artificial Sequence
<220> FEATURE:
<223> OTHER INFORMATION: IDO1-176-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (19)..(19)
<223> OTHER INFORMATION: RNA
<220> FEATURE:
<221> NAME/KEY: misc_feature
<222> LOCATION: (24)..(24)
<223> OTHER INFORMATION: 3' propanediol (C3) spacer blocking group

<400> SEQUENCE: 61
gcagagcaaa gcccacttct tcaa                                                24

<210> SEQ ID NO 62

```
<211> LENGTH: 25
<212> TYPE: DNA
<213> ORGANISM: Artificial Sequence
<220> FEATURE:
<223> OTHER INFORMATION: CYP27A-31016-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (20)..(20)
<223> OTHER INFORMATION: RNA
<220> FEATURE:
<221> NAME/KEY: misc_feature
<222> LOCATION: (25)..(25)
<223> OTHER INFORMATION: 3' propanediol (C3) spacer blocking group

<400> SEQUENCE: 62
cctttggtga ggactcccag atggc                                            25

<210> SEQ ID NO 63
<211> LENGTH: 21
<212> TYPE: DNA
<213> ORGANISM: Artificial Sequence
<220> FEATURE:
<223> OTHER INFORMATION: CYP27A-31016-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (16)..(16)
<223> OTHER INFORMATION: RNA
<220> FEATURE:
<221> NAME/KEY: misc_feature
<222> LOCATION: (21)..(21)
<223> OTHER INFORMATION: 3' propanediol (C3) spacer blocking group

<400> SEQUENCE: 63
cctgggcccc atctgggagt g                                                21

<210> SEQ ID NO 64
<211> LENGTH: 30
<212> TYPE: DNA
<213> ORGANISM: Artificial Sequence
<220> FEATURE:
<223> OTHER INFORMATION: SAA 226-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (25)..(25)
<223> OTHER INFORMATION: RNA
<220> FEATURE:
<221> NAME/KEY: misc_feature
<222> LOCATION: (30)..(30)
<223> OTHER INFORMATION: 3' propanediol (C3) spacer blocking group

<400> SEQUENCE: 64
tctcctctga tctagagagg taagcaggga                                       30

<210> SEQ ID NO 65
<211> LENGTH: 24
<212> TYPE: DNA
<213> ORGANISM: Artificial Sequence
<220> FEATURE:
<223> OTHER INFORMATION: SAA 226-2
<220> FEATURE:
<221> NAME/KEY: misc_feature
```

```
<222> LOCATION: (1)..(1)
<223> OTHER INFORMATION: 5' universal domain (UniFor-UniPro-)
<220> FEATURE:
<221> NAME/KEY: misc_feature
<222> LOCATION: (19)..(19)
<223> OTHER INFORMATION: RNA
<220> FEATURE:
<221> NAME/KEY: misc_feature
<222> LOCATION: (24)..(24)
<223> OTHER INFORMATION: 3' propanediol (C3) spacer blocking group

<400> SEQUENCE: 65
accaggcccg accctgctua cctg                                              24

<210> SEQ ID NO 66
<211> LENGTH: 26
<212> TYPE: DNA
<213> ORGANISM: Artificial Sequence
<220> FEATURE:
<223> OTHER INFORMATION: KIF11-369-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (21)..(21)
<223> OTHER INFORMATION: RNA
<220> FEATURE:
<221> NAME/KEY: misc_feature
<222> LOCATION: (26)..(26)
<223> OTHER INFORMATION: 3' propanediol (C3) spacer blocking group

<400> SEQUENCE: 66
gagaagggga agaacatcca ggtgga                                            26

<210> SEQ ID NO 67
<211> LENGTH: 24
<212> TYPE: DNA
<213> ORGANISM: Artificial Sequence
<220> FEATURE:
<223> OTHER INFORMATION: KIF11-369-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (19)..(19)
<223> OTHER INFORMATION: RNA
<220> FEATURE:
<221> NAME/KEY: misc_feature
<222> LOCATION: (24)..(24)
<223> OTHER INFORMATION: 3' propanediol (C3) spacer blocking group

<400> SEQUENCE: 67
gcatctcacc accacctgga tgta                                              24

<210> SEQ ID NO 68
<211> LENGTH: 28
<212> TYPE: DNA
<213> ORGANISM: Artificial Sequence
<220> FEATURE:
<223> OTHER INFORMATION: C3-1394-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (23)..(23)
<223> OTHER INFORMATION: RNA
<220> FEATURE:
```

-continued

<221> NAME/KEY: misc_feature
<222> LOCATION: (28)..(28)
<223> OTHER INFORMATION: 3' propanediol (C3) spacer blocking group

<400> SEQUENCE: 68
ctggacagca ctagtttttt gcctgggt                28

<210> SEQ ID NO 69
<211> LENGTH: 22
<212> TYPE: DNA
<213> ORGANISM: Artificial Sequence
<220> FEATURE:
<223> OTHER INFORMATION: C3-1394-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (17)..(17)
<223> OTHER INFORMATION: RNA
<220> FEATURE:
<221> NAME/KEY: misc_feature
<222> LOCATION: (22)..(22)
<223> OTHER INFORMATION: 3' propanediol (C3) spacer blocking group

<400> SEQUENCE: 69
ccacgacttc ccaggcaaaa at                22

<210> SEQ ID NO 70
<211> LENGTH: 23
<212> TYPE: DNA
<213> ORGANISM: Artificial Sequence
<220> FEATURE:
<223> OTHER INFORMATION: HOGA-505-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (18)..(18)
<223> OTHER INFORMATION: RNA
<220> FEATURE:
<221> NAME/KEY: misc_feature
<222> LOCATION: (23)..(23)
<223> OTHER INFORMATION: 3' propanediol (C3) spacer blocking group

<400> SEQUENCE: 70
cactgcagag gtggactatg ggt                23

<210> SEQ ID NO 71
<211> LENGTH: 29
<212> TYPE: DNA
<213> ORGANISM: Artificial Sequence
<220> FEATURE:
<223> OTHER INFORMATION: HOGA-505-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (24)..(24)
<223> OTHER INFORMATION: RNA
<220> FEATURE:
<221> NAME/KEY: misc_feature
<222> LOCATION: (29)..(29)
<223> OTHER INFORMATION: 3' propanediol (C3) spacer blocking group

<400> SEQUENCE: 71
gattctcctc cagtttccca taguccacg                29

<210> SEQ ID NO 72
<211> LENGTH: 30
<212> TYPE: DNA
<213> ORGANISM: Artificial Sequence
<220> FEATURE:
<223> OTHER INFORMATION: EGFR-123344-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (25)..(25)
<223> OTHER INFORMATION: RNA
<220> FEATURE:
<221> NAME/KEY: misc_feature
<222> LOCATION: (30)..(30)
<223> OTHER INFORMATION: 3' propanediol (C3) spacer blocking group

<400> SEQUENCE: 72
ccagaggatg ttcaataact gtgaggtgga                                    30

<210> SEQ ID NO 73
<211> LENGTH: 25
<212> TYPE: DNA
<213> ORGANISM: Artificial Sequence
<220> FEATURE:
<223> OTHER INFORMATION: EGFR-123344-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (20)..(20)
<223> OTHER INFORMATION: RNA
<220> FEATURE:
<221> NAME/KEY: misc_feature
<222> LOCATION: (25)..(25)
<223> OTHER INFORMATION: 3' propanediol (C3) spacer blocking group

<400> SEQUENCE: 73
caaattccca aggaccaccu cacac                                         25

<210> SEQ ID NO 74
<211> LENGTH: 25
<212> TYPE: DNA
<213> ORGANISM: Artificial Sequence
<220> FEATURE:
<223> OTHER INFORMATION: ALDH2-15144-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (20)..(20)
<223> OTHER INFORMATION: RNA
<220> FEATURE:
<221> NAME/KEY: misc_feature
<222> LOCATION: (25)..(25)
<223> OTHER INFORMATION: 3' propanediol (C3) spacer blocking group

<400> SEQUENCE: 74
tgaaggggac aaggtgagaa ctgga                                         25

<210> SEQ ID NO 75
<211> LENGTH: 27
<212> TYPE: DNA
<213> ORGANISM: Artificial Sequence
<220> FEATURE:

<223> OTHER INFORMATION: ALDH2-15144-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 75
cccaaggtaa gtcaccagtt cucacca                                    27

<210> SEQ ID NO 76
<211> LENGTH: 25
<212> TYPE: DNA
<213> ORGANISM: Artificial Sequence
<220> FEATURE:
<223> OTHER INFORMATION: AGXT-140-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (20)..(20)
<223> OTHER INFORMATION: RNA
<220> FEATURE:
<221> NAME/KEY: misc_feature
<222> LOCATION: (25)..(25)
<223> OTHER INFORMATION: 3' propanediol (C3) spacer blocking group

<400> SEQUENCE: 76
ccatggcctc tcacaagctg ctgga                                      25

<210> SEQ ID NO 77
<211> LENGTH: 21
<212> TYPE: DNA
<213> ORGANISM: Artificial Sequence
<220> FEATURE:
<223> OTHER INFORMATION: AGXT-140-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (16)..(16)
<223> OTHER INFORMATION: RNA
<220> FEATURE:
<221> NAME/KEY: misc_feature
<222> LOCATION: (21)..(21)
<223> OTHER INFORMATION: 3' propanediol (C3) spacer blocking group

<400> SEQUENCE: 77
gggggtcacc agcagcttgt c                                          21

<210> SEQ ID NO 78
<211> LENGTH: 30
<212> TYPE: DNA
<213> ORGANISM: Artificial Sequence
<220> FEATURE:
<223> OTHER INFORMATION: APOC-2929-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<220> FEATURE:
<221> NAME/KEY: misc_feature
<222> LOCATION: (25)..(25)
<223> OTHER INFORMATION: RNA
<220> FEATURE:
<221> NAME/KEY: misc_feature
<222> LOCATION: (30)..(30)
<223> OTHER INFORMATION: 3' propanediol (C3) spacer blocking group

<400> SEQUENCE: 78
ccgttaagga caagttctct gagtuctggc                                     30

<210> SEQ ID NO 79
<211> LENGTH: 27
<212> TYPE: DNA
<213> ORGANISM: Artificial Sequence
<220> FEATURE:
<223> OTHER INFORMATION: APOC-2929-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 79
tcagggtcca aatcccagaa cucagac                                        27

<210> SEQ ID NO 80
<211> LENGTH: 36
<212> TYPE: DNA
<213> ORGANISM: Artificial Sequence
<220> FEATURE:
<223> OTHER INFORMATION: Met 27554-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (31)..(31)
<223> OTHER INFORMATION: RNA
<220> FEATURE:
<221> NAME/KEY: misc_feature
<222> LOCATION: (36)..(36)
<223> OTHER INFORMATION: 3' propanediol (C3) spacer blocking group

<400> SEQUENCE: 80
aattttattt acttcttgac ggtccaaagg gaaaca                              36

<210> SEQ ID NO 81
<211> LENGTH: 28
<212> TYPE: DNA
<213> ORGANISM: Artificial Sequence
<220> FEATURE:
<223> OTHER INFORMATION: Met 27554-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (23)..(23)
<223> OTHER INFORMATION: RNA
<220> FEATURE:
<221> NAME/KEY: misc_feature
<222> LOCATION: (28)..(28)
<223> OTHER INFORMATION: 3' propanediol (C3) spacer blocking group

<400> SEQUENCE: 81
gtctgagcat ctagagtttc ccuttggt                                              28

<210> SEQ ID NO 82
<211> LENGTH: 27
<212> TYPE: DNA
<213> ORGANISM: Artificial Sequence
<220> FEATURE:
<223> OTHER INFORMATION: SAA 88-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 82
aggtgaggag cacaccaagg agtgata                                               27

<210> SEQ ID NO 83
<211> LENGTH: 35
<212> TYPE: DNA
<213> ORGANISM: Artificial Sequence
<220> FEATURE:
<223> OTHER INFORMATION: SAA 88-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (30)..(30)
<223> OTHER INFORMATION: RNA
<220> FEATURE:
<221> NAME/KEY: misc_feature
<222> LOCATION: (35)..(35)
<223> OTHER INFORMATION: 3' propanediol (C3) spacer blocking group

<400> SEQUENCE: 83
gaaaacagag taagttttaa aaatcactcc ttgga                                      35

<210> SEQ ID NO 84
<211> LENGTH: 20
<212> TYPE: DNA
<213> ORGANISM: Artificial Sequence
<220> FEATURE:
<223> OTHER INFORMATION: HIF1A-293-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (15)..(15)
<223> OTHER INFORMATION: RNA
<220> FEATURE:
<221> NAME/KEY: misc_feature
<222> LOCATION: (20)..(20)
<223> OTHER INFORMATION: 3' propanediol (C3) spacer blocking group

<400> SEQUENCE: 84
tcgcaccccc acctctggag                                                       20

<210> SEQ ID NO 85
<211> LENGTH: 27

<212> TYPE: DNA
<213> ORGANISM: Artificial Sequence
<220> FEATURE:
<223> OTHER INFORMATION: HIF1A-293-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 85
gaaggaaagg caagtccaga ggtgggc            27

<210> SEQ ID NO 86
<211> LENGTH: 36
<212> TYPE: DNA
<213> ORGANISM: Artificial Sequence
<220> FEATURE:
<223> OTHER INFORMATION: Met 27475-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (31)..(31)
<223> OTHER INFORMATION: RNA
<220> FEATURE:
<221> NAME/KEY: misc_feature
<222> LOCATION: (36)..(36)
<223> OTHER INFORMATION: 3' propanediol (C3) spacer blocking group

<400> SEQUENCE: 86
aattttattt acttcttgac ggtccaaagg gaaaca            36

<210> SEQ ID NO 87
<211> LENGTH: 28
<212> TYPE: DNA
<213> ORGANISM: Artificial Sequence
<220> FEATURE:
<223> OTHER INFORMATION: Met 27475-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (23)..(23)
<223> OTHER INFORMATION: RNA
<220> FEATURE:
<221> NAME/KEY: misc_feature
<222> LOCATION: (28)..(28)
<223> OTHER INFORMATION: 3' propanediol (C3) spacer blocking group

<400> SEQUENCE: 87
gtctgagcat ctagagtttc ccuttggt            28

<210> SEQ ID NO 88
<211> LENGTH: 21
<212> TYPE: DNA
<213> ORGANISM: Artificial Sequence
<220> FEATURE:
<223> OTHER INFORMATION: HAMP-295-1
<220> FEATURE:
<221> NAME/KEY: misc_feature
<222> LOCATION: (1)..(1)

<223> OTHER INFORMATION: 5' universal domain (UniFor-UniPro-)
<220> FEATURE:
<221> NAME/KEY: misc_feature
<222> LOCATION: (16)..(16)
<223> OTHER INFORMATION: RNA
<220> FEATURE:
<221> NAME/KEY: misc_feature
<222> LOCATION: (21)..(21)
<223> OTHER INFORMATION: 3' propanediol (C3) spacer blocking group

<400> SEQUENCE: 88
ctcgccagcc tgaccagtgg g                                            21

<210> SEQ ID NO 89
<211> LENGTH: 25
<212> TYPE: DNA
<213> ORGANISM: Artificial Sequence
<220> FEATURE:
<223> OTHER INFORMATION: HAMP-295-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (20)..(20)
<223> OTHER INFORMATION: RNA
<220> FEATURE:
<221> NAME/KEY: misc_feature
<222> LOCATION: (25)..(25)
<223> OTHER INFORMATION: 3' propanediol (C3) spacer blocking group

<400> SEQUENCE: 89
gggaaaacag agccactggu caggg                                        25

<210> SEQ ID NO 90
<211> LENGTH: 22
<212> TYPE: DNA
<213> ORGANISM: Artificial Sequence
<220> FEATURE:
<223> OTHER INFORMATION: GRHPR-2234-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (17)..(17)
<223> OTHER INFORMATION: RNA
<220> FEATURE:
<221> NAME/KEY: misc_feature
<222> LOCATION: (22)..(22)
<223> OTHER INFORMATION: 3' propanediol (C3) spacer blocking group

<400> SEQUENCE: 90
gcctcctctc cgaccacgtg gt                                           22

<210> SEQ ID NO 91
<211> LENGTH: 26
<212> TYPE: DNA
<213> ORGANISM: Artificial Sequence
<220> FEATURE:
<223> OTHER INFORMATION: GRHPR-2234-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (20)..(20)
<223> OTHER INFORMATION: RNA
<220> FEATURE:
<221> NAME/KEY: misc_feature
<222> LOCATION: (26)..(26)
<223> OTHER INFORMATION: 3' propanediol (C3) spacer blocking group

<400> SEQUENCE: 91
ggatcctctt gtccacgtgg tcggac                                    26

<210> SEQ ID NO 92
<211> LENGTH: 20
<212> TYPE: DNA
<213> ORGANISM: Artificial Sequence
<220> FEATURE:
<223> OTHER INFORMATION: HAMP-88-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (15)..(15)
<223> OTHER INFORMATION: RNA
<220> FEATURE:
<221> NAME/KEY: misc_feature
<222> LOCATION: (20)..(20)
<223> OTHER INFORMATION: 3' propanediol (C3) spacer blocking group

<400> SEQUENCE: 92
ggcgccacca ccttcttggt                                           20

<210> SEQ ID NO 93
<211> LENGTH: 27
<212> TYPE: DNA
<213> ORGANISM: Artificial Sequence
<220> FEATURE:
<223> OTHER INFORMATION: HAMP-88-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 93
gctctgtctc atttccaaga aggtgga                                   27

<210> SEQ ID NO 94
<211> LENGTH: 28
<212> TYPE: DNA
<213> ORGANISM: Artificial Sequence
<220> FEATURE:
<223> OTHER INFORMATION: Met 27254-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (23)..(23)
<223> OTHER INFORMATION: RNA
<220> FEATURE:
<221> NAME/KEY: misc_feature
<222> LOCATION: (28)..(28)
<223> OTHER INFORMATION: 3' propanediol (C3) spacer blocking group

<400> SEQUENCE: 94
gagccaaagt cctttcatct gtaaaggt                                  28

```
<210> SEQ ID NO 95
<211> LENGTH: 30
<212> TYPE: DNA
<213> ORGANISM: Artificial Sequence
<220> FEATURE:
<223> OTHER INFORMATION: Met 27254-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (25)..(25)
<223> OTHER INFORMATION: RNA
<220> FEATURE:
<221> NAME/KEY: misc_feature
<222> LOCATION: (30)..(30)
<223> OTHER INFORMATION: 3' propanediol (C3) spacer blocking group

<400> SEQUENCE: 95
gaagttgatg aaccggtcct ttacagatgt                                   30

<210> SEQ ID NO 96
<211> LENGTH: 26
<212> TYPE: DNA
<213> ORGANISM: Artificial Sequence
<220> FEATURE:
<223> OTHER INFORMATION: GRHPR-2264-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (21)..(21)
<223> OTHER INFORMATION: RNA
<220> FEATURE:
<221> NAME/KEY: misc_feature
<222> LOCATION: (26)..(26)
<223> OTHER INFORMATION: 3' propanediol (C3) spacer blocking group

<400> SEQUENCE: 96
acaagaggat cctggatgct gcagga                                       26

<210> SEQ ID NO 97
<211> LENGTH: 23
<212> TYPE: DNA
<213> ORGANISM: Artificial Sequence
<220> FEATURE:
<223> OTHER INFORMATION: GRHPR-2264-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (18)..(18)
<223> OTHER INFORMATION: RNA
<220> FEATURE:
<221> NAME/KEY: misc_feature
<222> LOCATION: (23)..(23)
<223> OTHER INFORMATION: 3' propanediol (C3) spacer blocking group

<400> SEQUENCE: 97
cgctctagct ccttggcagg gaa                                          23

<210> SEQ ID NO 98
<211> LENGTH: 27
<212> TYPE: DNA
<213> ORGANISM: Artificial Sequence
<220> FEATURE:
<223> OTHER INFORMATION: Serpina 279-1
```

```
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 98
actcagttcc acaggtggga gggaggc                                         27

<210> SEQ ID NO 99
<211> LENGTH: 27
<212> TYPE: DNA
<213> ORGANISM: Artificial Sequence
<220> FEATURE:
<223> OTHER INFORMATION: Serpina 279-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 99
cactctaagc cctgctgtcc cacctga                                         27

<210> SEQ ID NO 100
<211> LENGTH: 27
<212> TYPE: DNA
<213> ORGANISM: Artificial Sequence
<220> FEATURE:
<223> OTHER INFORMATION: Myc 459-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 100
cgggaggcta ttctgcccat tugggat                                         27

<210> SEQ ID NO 101
<211> LENGTH: 24
<212> TYPE: DNA
<213> ORGANISM: Artificial Sequence
<220> FEATURE:
<223> OTHER INFORMATION: Myc 459-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (19)..(19)
```

```
<223> OTHER INFORMATION: RNA
<220> FEATURE:
<221> NAME/KEY: misc_feature
<222> LOCATION: (24)..(24)
<223> OTHER INFORMATION: 3' propanediol (C3) spacer blocking group

<400> SEQUENCE: 101
cggggaagtg tccccaaaug ggct                                              24

<210> SEQ ID NO 102
<211> LENGTH: 23
<212> TYPE: DNA
<213> ORGANISM: Artificial Sequence
<220> FEATURE:
<223> OTHER INFORMATION: Serpina 130-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (18)..(18)
<223> OTHER INFORMATION: RNA
<220> FEATURE:
<221> NAME/KEY: misc_feature
<222> LOCATION: (23)..(23)
<223> OTHER INFORMATION: 3' propanediol (C3) spacer blocking group

<400> SEQUENCE: 102
gctgctgctg ccaggaautc cac                                               23

<210> SEQ ID NO 103
<211> LENGTH: 24
<212> TYPE: DNA
<213> ORGANISM: Artificial Sequence
<220> FEATURE:
<223> OTHER INFORMATION: Serpina 130-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (19)..(19)
<223> OTHER INFORMATION: RNA
<220> FEATURE:
<221> NAME/KEY: misc_feature
<222> LOCATION: (24)..(24)
<223> OTHER INFORMATION: 3' propanediol (C3) spacer blocking group

<400> SEQUENCE: 103
cccctccaac ctggaattcc tggg                                              24

<210> SEQ ID NO 104
<211> LENGTH: 23
<212> TYPE: DNA
<213> ORGANISM: Artificial Sequence
<220> FEATURE:
<223> OTHER INFORMATION: Myc 490-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (18)..(18)
<223> OTHER INFORMATION: RNA
<220> FEATURE:
<221> NAME/KEY: misc_feature
<222> LOCATION: (23)..(23)
<223> OTHER INFORMATION: 3' propanediol (C3) spacer blocking group

<400> SEQUENCE: 104
```
ctgccaggac ccgcttcuct gat                                          23

<210> SEQ ID NO 105
<211> LENGTH: 26
<212> TYPE: DNA
<213> ORGANISM: Artificial Sequence
<220> FEATURE:
<223> OTHER INFORMATION: Myc 490-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (21)..(21)
<223> OTHER INFORMATION: RNA
<220> FEATURE:
<221> NAME/KEY: misc_feature
<222> LOCATION: (26)..(26)
<223> OTHER INFORMATION: 3' propanediol (C3) spacer blocking group

<400> SEQUENCE: 105
caaggagagc ctttcagaga agcggc                                       26

<210> SEQ ID NO 106
<211> LENGTH: 23
<212> TYPE: DNA
<213> ORGANISM: Artificial Sequence
<220> FEATURE:
<223> OTHER INFORMATION: GRHPR-2179-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (18)..(18)
<223> OTHER INFORMATION: RNA
<220> FEATURE:
<221> NAME/KEY: misc_feature
<222> LOCATION: (23)..(23)
<223> OTHER INFORMATION: 3' propanediol (C3) spacer blocking group

<400> SEQUENCE: 106
gatgagccca tccctgccaa ggt                                          23

<210> SEQ ID NO 107
<211> LENGTH: 23
<212> TYPE: DNA
<213> ORGANISM: Artificial Sequence
<220> FEATURE:
<223> OTHER INFORMATION: GRHPR-2179-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (18)..(18)
<223> OTHER INFORMATION: RNA
<220> FEATURE:
<221> NAME/KEY: misc_feature
<222> LOCATION: (23)..(23)
<223> OTHER INFORMATION: 3' propanediol (C3) spacer blocking group

<400> SEQUENCE: 107
cgctctagct ccttggcagg gaa                                          23

<210> SEQ ID NO 108
<211> LENGTH: 21
<212> TYPE: DNA

```
<213> ORGANISM: Artificial Sequence
<220> FEATURE:
<223> OTHER INFORMATION: GYG-2851-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (16)..(16)
<223> OTHER INFORMATION: RNA
<220> FEATURE:
<221> NAME/KEY: misc_feature
<222> LOCATION: (21)..(21)
<223> OTHER INFORMATION: 3' propanediol (C3) spacer blocking group

<400> SEQUENCE: 108
tcgccacccc tcaggutctca c                                              21

<210> SEQ ID NO 109
<211> LENGTH: 26
<212> TYPE: DNA
<213> ORGANISM: Artificial Sequence
<220> FEATURE:
<223> OTHER INFORMATION: GYG-2851-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (21)..(21)
<223> OTHER INFORMATION: RNA
<220> FEATURE:
<221> NAME/KEY: misc_feature
<222> LOCATION: (26)..(26)
<223> OTHER INFORMATION: 3' propanediol (C3) spacer blocking group

<400> SEQUENCE: 109
acctcatgga gtctgagacc ugaggc                                          26

<210> SEQ ID NO 110
<211> LENGTH: 21
<212> TYPE: DNA
<213> ORGANISM: Artificial Sequence
<220> FEATURE:
<223> OTHER INFORMATION: GYG-2793-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (16)..(16)
<223> OTHER INFORMATION: RNA
<220> FEATURE:
<221> NAME/KEY: misc_feature
<222> LOCATION: (21)..(21)
<223> OTHER INFORMATION: 3' propanediol (C3) spacer blocking group

<400> SEQUENCE: 110
gccctggtcc tgggaucatc a                                               21

<210> SEQ ID NO 111
<211> LENGTH: 28
<212> TYPE: DNA
<213> ORGANISM: Artificial Sequence
<220> FEATURE:
<223> OTHER INFORMATION: GYG-2793-2
<220> FEATURE:
<221> NAME/KEY: misc_feature
<222> LOCATION: (1)..(1)
<223> OTHER INFORMATION: 5' universal domain (UniFor-UniPro-)
```

<220> FEATURE:
<221> NAME/KEY: misc_feature
<222> LOCATION: (23)..(23)
<223> OTHER INFORMATION: RNA
<220> FEATURE:
<221> NAME/KEY: misc_feature
<222> LOCATION: (28)..(28)
<223> OTHER INFORMATION: 3' propanediol (C3) spacer blocking group

<400> SEQUENCE: 111
ctgtgctgtt tcagagatga tcccaggt                                    28

<210> SEQ ID NO 112
<211> LENGTH: 28
<212> TYPE: DNA
<213> ORGANISM: Artificial Sequence
<220> FEATURE:
<223> OTHER INFORMATION: Serpina 79-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (23)..(23)
<223> OTHER INFORMATION: RNA
<220> FEATURE:
<221> NAME/KEY: misc_feature
<222> LOCATION: (28)..(28)
<223> OTHER INFORMATION: 3' propanediol (C3) spacer blocking group

<400> SEQUENCE: 112
caagagtcct gagctgaacc aagaaggt                                    28

<210> SEQ ID NO 113
<211> LENGTH: 25
<212> TYPE: DNA
<213> ORGANISM: Artificial Sequence
<220> FEATURE:
<223> OTHER INFORMATION: Serpina 79-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (20)..(20)
<223> OTHER INFORMATION: RNA
<220> FEATURE:
<221> NAME/KEY: misc_feature
<222> LOCATION: (25)..(25)
<223> OTHER INFORMATION: 3' propanediol (C3) spacer blocking group

<400> SEQUENCE: 113
cgaccccctc ctccttcttg gttct                                       25

<210> SEQ ID NO 114
<211> LENGTH: 28
<212> TYPE: DNA
<213> ORGANISM: Artificial Sequence
<220> FEATURE:
<223> OTHER INFORMATION: Myc 538-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (23)..(23)
<223> OTHER INFORMATION: RNA
<220> FEATURE:
<221> NAME/KEY: misc_feature
<222> LOCATION: (28)..(28)

```
<223> OTHER INFORMATION: 3' propanediol (C3) spacer blocking group

<400> SEQUENCE: 114
ctgcttagac gctggatttt ttcggga                                              28

<210> SEQ ID NO 115
<211> LENGTH: 27
<212> TYPE: DNA
<213> ORGANISM: Artificial Sequence
<220> FEATURE:
<223> OTHER INFORMATION: Myc 538-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (22)..(22)
<223> OTHER INFORMATION: RNA
<220> FEATURE:
<221> NAME/KEY: misc_feature
<222> LOCATION: (27)..(27)
<223> OTHER INFORMATION: 3' propanediol (C3) spacer blocking group

<400> SEQUENCE: 115
ctggttttcc actacccgaa araaaaa                                              27

<210> SEQ ID NO 116
<211> LENGTH: 31
<212> TYPE: DNA
<213> ORGANISM: Artificial Sequence
<220> FEATURE:
<223> OTHER INFORMATION: GYG-2744-1
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (26)..(26)
<223> OTHER INFORMATION: RNA
<220> FEATURE:
<221> NAME/KEY: misc_feature
<222> LOCATION: (31)..(31)
<223> OTHER INFORMATION: 3' propanediol (C3) spacer blocking group

<400> SEQUENCE: 116
ctttgtatta agatcaggcc tttgtgacac a                                         31

<210> SEQ ID NO 117
<211> LENGTH: 28
<212> TYPE: DNA
<213> ORGANISM: Artificial Sequence
<220> FEATURE:
<223> OTHER INFORMATION: GYG-2744-2
<220> FEATURE:
<221> NAME/KEY: misc_feature
<222> LOCATION: (1)..(1)
<223> OTHER INFORMATION: 5' universal domain (UniFor-UniPro-)
<220> FEATURE:
<221> NAME/KEY: misc_feature
<222> LOCATION: (23)..(23)
<223> OTHER INFORMATION: RNA
<220> FEATURE:
<221> NAME/KEY: misc_feature
<222> LOCATION: (28)..(28)
<223> OTHER INFORMATION: 3' propanediol (C3) spacer blocking group

<400> SEQUENCE: 117
catcgtttgt ggttagtgtc acaaaggg                                             28
```

```
<210> SEQ ID NO 118
<211> LENGTH: 19
<212> TYPE: DNA
<213> ORGANISM: Artificial Sequence
<220> FEATURE:
<223> OTHER INFORMATION: RNase P For

<400> SEQUENCE: 118
gcggagggaa gctcatcag                                                  19

<210> SEQ ID NO 119
<211> LENGTH: 22
<212> TYPE: DNA
<213> ORGANISM: Artificial Sequence
<220> FEATURE:
<223> OTHER INFORMATION: RNase P Rev

<400> SEQUENCE: 119
ccctagtctc agaccttccc aa                                              22

<210> SEQ ID NO 120
<211> LENGTH: 24
<212> TYPE: DNA
<213> ORGANISM: Artificial Sequence
<220> FEATURE:
<223> OTHER INFORMATION: RNase P probe
<220> FEATURE:
<221> NAME/KEY: misc_feature
<222> LOCATION: (1)..(1)
<223> OTHER INFORMATION: 5' 6-Fluorescein fluorescent dye (FAM)
<220> FEATURE:
<221> NAME/KEY: misc_feature
<222> LOCATION: (24)..(24)
<223> OTHER INFORMATION: 3' Iowa Black fluorescent quencher (IBFQ)

<400> SEQUENCE: 120
ccacgagctg agtgcgtcct gtca                                            24

<210> SEQ ID NO 121
<211> LENGTH: 22
<212> TYPE: DNA
<213> ORGANISM: Artificial Sequence
<220> FEATURE:
<223> OTHER INFORMATION: GCK-356-1

<400> SEQUENCE: 121
gaggaaactg tgactgaacc tc                                              22

<210> SEQ ID NO 122
<211> LENGTH: 16
<212> TYPE: DNA
<213> ORGANISM: Artificial Sequence
<220> FEATURE:
<223> OTHER INFORMATION: GCK-356-2

<400> SEQUENCE: 122
ccaaggcttc tccgcc                                                     16

<210> SEQ ID NO 123
<211> LENGTH: 17
<212> TYPE: DNA
<213> ORGANISM: Artificial Sequence
<220> FEATURE:
<223> OTHER INFORMATION: ERBB3-33-1

<400> SEQUENCE: 123
gagtccgggg agggatg                                                    17
```

```
<210> SEQ ID NO 124
<211> LENGTH: 19
<212> TYPE: DNA
<213> ORGANISM: Artificial Sequence
<220> FEATURE:
<223> OTHER INFORMATION: ERBB3-33-2

<400> SEQUENCE: 124
caatccctac tccagcctc                                                    19

<210> SEQ ID NO 125
<211> LENGTH: 21
<212> TYPE: DNA
<213> ORGANISM: Artificial Sequence
<220> FEATURE:
<223> OTHER INFORMATION: TTR-1257-1

<400> SEQUENCE: 125
atgtgagcct ctctctacca a                                                 21

<210> SEQ ID NO 126
<211> LENGTH: 23
<212> TYPE: DNA
<213> ORGANISM: Artificial Sequence
<220> FEATURE:
<223> OTHER INFORMATION: TTR-1257-2

<400> SEQUENCE: 126
gtcctctgat ggtcaaagtt cta                                               23

<210> SEQ ID NO 127
<211> LENGTH: 16
<212> TYPE: DNA
<213> ORGANISM: Artificial Sequence
<220> FEATURE:
<223> OTHER INFORMATION: HAMP-253-1

<400> SEQUENCE: 127
cactggtcag gctggc                                                       16

<210> SEQ ID NO 128
<211> LENGTH: 18
<212> TYPE: DNA
<213> ORGANISM: Artificial Sequence
<220> FEATURE:
<223> OTHER INFORMATION: HAMP-253-2

<400> SEQUENCE: 128
caagctcaag acccagca                                                     18

<210> SEQ ID NO 129
<211> LENGTH: 25
<212> TYPE: DNA
<213> ORGANISM: Artificial Sequence
<220> FEATURE:
<223> OTHER INFORMATION: BIRC5-606-1

<400> SEQUENCE: 129
caactcaaat cttttgacaa ctcag                                             25

<210> SEQ ID NO 130
<211> LENGTH: 16
<212> TYPE: DNA
<213> ORGANISM: Artificial Sequence
<220> FEATURE:
<223> OTHER INFORMATION: BIRC5-606-2
```

-continued

<400> SEQUENCE: 130
ggagctggaa ggctgg                                          16

<210> SEQ ID NO 131
<211> LENGTH: 23
<212> TYPE: DNA
<213> ORGANISM: Artificial Sequence
<220> FEATURE:
<223> OTHER INFORMATION: SAA 146-1

<400> SEQUENCE: 131
ttcagaatgg tatggctgta tgc                                  23

<210> SEQ ID NO 132
<211> LENGTH: 20
<212> TYPE: DNA
<213> ORGANISM: Artificial Sequence
<220> FEATURE:
<223> OTHER INFORMATION: SAA 146-2

<400> SEQUENCE: 132
cacagatcag gtgaggagca                                      20

<210> SEQ ID NO 133
<211> LENGTH: 19
<212> TYPE: DNA
<213> ORGANISM: Artificial Sequence
<220> FEATURE:
<223> OTHER INFORMATION: IDO1-97-1

<400> SEQUENCE: 133
gttttccata gcgtgtgcc                                       19

<210> SEQ ID NO 134
<211> LENGTH: 17
<212> TYPE: DNA
<213> ORGANISM: Artificial Sequence
<220> FEATURE:
<223> OTHER INFORMATION: IDO1-97-2

<400> SEQUENCE: 134
gtggtcactg gctgtgg                                         17

<210> SEQ ID NO 135
<211> LENGTH: 23
<212> TYPE: DNA
<213> ORGANISM: Artificial Sequence
<220> FEATURE:
<223> OTHER INFORMATION: IDO1-176-1

<400> SEQUENCE: 135
ttcccacatt ttactgcctt ctc                                  23

<210> SEQ ID NO 136
<211> LENGTH: 20
<212> TYPE: DNA
<213> ORGANISM: Artificial Sequence
<220> FEATURE:
<223> OTHER INFORMATION: IDO1-176-2

<400> SEQUENCE: 136
cgctatggaa aactcctgga                                      20

<210> SEQ ID NO 137

```
<211> LENGTH: 18
<212> TYPE: DNA
<213> ORGANISM: Artificial Sequence
<220> FEATURE:
<223> OTHER INFORMATION: CYP27A-31016-1

<400> SEQUENCE: 137
caggtctgtg catcagcg                                                 18

<210> SEQ ID NO 138
<211> LENGTH: 20
<212> TYPE: DNA
<213> ORGANISM: Artificial Sequence
<220> FEATURE:
<223> OTHER INFORMATION: CYP27A-31016-2

<400> SEQUENCE: 138
ctttctggaa gcgatacctg                                               20

<210> SEQ ID NO 139
<211> LENGTH: 20
<212> TYPE: DNA
<213> ORGANISM: Artificial Sequence
<220> FEATURE:
<223> OTHER INFORMATION: SAA 226-1

<400> SEQUENCE: 139
cgcacagaac tcaacatggg                                               20

<210> SEQ ID NO 140
<211> LENGTH: 24
<212> TYPE: DNA
<213> ORGANISM: Artificial Sequence
<220> FEATURE:
<223> OTHER INFORMATION: SAA 226-2

<400> SEQUENCE: 140
aatagttatc ctggggcata cagc                                          24

<210> SEQ ID NO 141
<211> LENGTH: 18
<212> TYPE: DNA
<213> ORGANISM: Artificial Sequence
<220> FEATURE:
<223> OTHER INFORMATION: KIF11-369-1

<400> SEQUENCE: 141
gctcggaatc ctgtcagc                                                 18

<210> SEQ ID NO 142
<211> LENGTH: 18
<212> TYPE: DNA
<213> ORGANISM: Artificial Sequence
<220> FEATURE:
<223> OTHER INFORMATION: KIF11-369-2

<400> SEQUENCE: 142
cagccaaatt cgtctgcg                                                 18

<210> SEQ ID NO 143
<211> LENGTH: 22
<212> TYPE: DNA
<213> ORGANISM: Artificial Sequence
<220> FEATURE:
<223> OTHER INFORMATION: C3-1394-1

<400> SEQUENCE: 143
```
gggatgttcc agtcactgtt ac                                              22

<210> SEQ ID NO 144
<211> LENGTH: 15
<212> TYPE: DNA
<213> ORGANISM: Artificial Sequence
<220> FEATURE:
<223> OTHER INFORMATION: C3-1394-2

<400> SEQUENCE: 144
ggttggtggc agggg                                                      15

<210> SEQ ID NO 145
<211> LENGTH: 16
<212> TYPE: DNA
<213> ORGANISM: Artificial Sequence
<220> FEATURE:
<223> OTHER INFORMATION: HOGA-505-1

<400> SEQUENCE: 145
aggggaaggt gcccag                                                     16

<210> SEQ ID NO 146
<211> LENGTH: 17
<212> TYPE: DNA
<213> ORGANISM: Artificial Sequence
<220> FEATURE:
<223> OTHER INFORMATION: HOGA-505-2

<400> SEQUENCE: 146
aaggtggaca ttgcggg                                                    17

<210> SEQ ID NO 147
<211> LENGTH: 23
<212> TYPE: DNA
<213> ORGANISM: Artificial Sequence
<220> FEATURE:
<223> OTHER INFORMATION: EGFR-123344-1

<400> SEQUENCE: 147
tcataattcc tctgcacata ggt                                             23

<210> SEQ ID NO 148
<211> LENGTH: 18
<212> TYPE: DNA
<213> ORGANISM: Artificial Sequence
<220> FEATURE:
<223> OTHER INFORMATION: EGFR-123344-2

<400> SEQUENCE: 148
gccaaggcac gagtaaca                                                   18

<210> SEQ ID NO 149
<211> LENGTH: 28
<212> TYPE: DNA
<213> ORGANISM: Artificial Sequence
<220> FEATURE:
<223> OTHER INFORMATION: ALDH2-15144-1

<400> SEQUENCE: 149
cgtataaaat agaagacgaa tccatccc                                        28

<210> SEQ ID NO 150
<211> LENGTH: 15
<212> TYPE: DNA

```
<213> ORGANISM: Artificial Sequence
<220> FEATURE:
<223> OTHER INFORMATION: ALDH2-15144-2

<400> SEQUENCE: 150
atggcacgat gccgt                                                          15

<210> SEQ ID NO 151
<211> LENGTH: 15
<212> TYPE: DNA
<213> ORGANISM: Artificial Sequence
<220> FEATURE:
<223> OTHER INFORMATION: AGXT-140-1

<400> SEQUENCE: 151
ggcttgagca gggcc                                                          15

<210> SEQ ID NO 152
<211> LENGTH: 15
<212> TYPE: DNA
<213> ORGANISM: Artificial Sequence
<220> FEATURE:
<223> OTHER INFORMATION: AGXT-140-2

<400> SEQUENCE: 152
tggccaaggc cagtg                                                          15

<210> SEQ ID NO 153
<211> LENGTH: 15
<212> TYPE: DNA
<213> ORGANISM: Artificial Sequence
<220> FEATURE:
<223> OTHER INFORMATION: APOC-2929-1

<400> SEQUENCE: 153
tcaggcagcc acggc                                                          15

<210> SEQ ID NO 154
<211> LENGTH: 18
<212> TYPE: DNA
<213> ORGANISM: Artificial Sequence
<220> FEATURE:
<223> OTHER INFORMATION: APOC-2929-2

<400> SEQUENCE: 154
gtgaccgatg gcttcagt                                                       18

<210> SEQ ID NO 155
<211> LENGTH: 27
<212> TYPE: DNA
<213> ORGANISM: Artificial Sequence
<220> FEATURE:
<223> OTHER INFORMATION: Met 27554-1

<400> SEQUENCE: 155
catacgcagc ctgaagtata ttaaaca                                             27

<210> SEQ ID NO 156
<211> LENGTH: 26
<212> TYPE: DNA
<213> ORGANISM: Artificial Sequence
<220> FEATURE:
<223> OTHER INFORMATION: Met 27554-2

<400> SEQUENCE: 156
tagatgctca gactttcac acaaga                                               26
```

<210> SEQ ID NO 157
<211> LENGTH: 23
<212> TYPE: DNA
<213> ORGANISM: Artificial Sequence
<220> FEATURE:
<223> OTHER INFORMATION: SAA 88-1

<400> SEQUENCE: 157
ttcagaatgg tatggctgta tgc                                              23

<210> SEQ ID NO 158
<211> LENGTH: 25
<212> TYPE: DNA
<213> ORGANISM: Artificial Sequence
<220> FEATURE:
<223> OTHER INFORMATION: SAA 88-2

<400> SEQUENCE: 158
agcagggaag gctcagtata aatag                                            25

<210> SEQ ID NO 159
<211> LENGTH: 16
<212> TYPE: DNA
<213> ORGANISM: Artificial Sequence
<220> FEATURE:
<223> OTHER INFORMATION: HIF1A-293-1

<400> SEQUENCE: 159
taagcgctgg ctccct                                                      16

<210> SEQ ID NO 160
<211> LENGTH: 20
<212> TYPE: DNA
<213> ORGANISM: Artificial Sequence
<220> FEATURE:
<223> OTHER INFORMATION: HIF1A-293-2

<400> SEQUENCE: 160
ctctagtctc acgaggggtt                                                  20

<210> SEQ ID NO 161
<211> LENGTH: 26
<212> TYPE: DNA
<213> ORGANISM: Artificial Sequence
<220> FEATURE:
<223> OTHER INFORMATION: Met 27475-1

<400> SEQUENCE: 161
ctcttttctg tgagaataca ctccag                                           26

<210> SEQ ID NO 162
<211> LENGTH: 24
<212> TYPE: DNA
<213> ORGANISM: Artificial Sequence
<220> FEATURE:
<223> OTHER INFORMATION: Met 27475-2

<400> SEQUENCE: 162
taccccatta agtatgtcca tgcc                                             24

<210> SEQ ID NO 163
<211> LENGTH: 17
<212> TYPE: DNA
<213> ORGANISM: Artificial Sequence
<220> FEATURE:

-continued

```
<223> OTHER INFORMATION: HAMP-295-1

<400> SEQUENCE: 163
tctcccatcc ctgctgc                                                17

<210> SEQ ID NO 164
<211> LENGTH: 15
<212> TYPE: DNA
<213> ORGANISM: Artificial Sequence
<220> FEATURE:
<223> OTHER INFORMATION: HAMP-295-2

<400> SEQUENCE: 164
ccgcttgcct cctgc                                                  15

<210> SEQ ID NO 165
<211> LENGTH: 16
<212> TYPE: DNA
<213> ORGANISM: Artificial Sequence
<220> FEATURE:
<223> OTHER INFORMATION: GRHPR-2234-1

<400> SEQUENCE: 165
cacccagtgt gcacct                                                 16

<210> SEQ ID NO 166
<211> LENGTH: 18
<212> TYPE: DNA
<213> ORGANISM: Artificial Sequence
<220> FEATURE:
<223> OTHER INFORMATION: GRHPR-2234-2

<400> SEQUENCE: 166
gccaaggagc tagagcga                                               18

<210> SEQ ID NO 167
<211> LENGTH: 16
<212> TYPE: DNA
<213> ORGANISM: Artificial Sequence
<220> FEATURE:
<223> OTHER INFORMATION: HAMP-88-1

<400> SEQUENCE: 167
gaggcggtgg tctgag                                                 16

<210> SEQ ID NO 168
<211> LENGTH: 17
<212> TYPE: DNA
<213> ORGANISM: Artificial Sequence
<220> FEATURE:
<223> OTHER INFORMATION: HAMP-88-2

<400> SEQUENCE: 168
tgttccctgt cgctctg                                                17

<210> SEQ ID NO 169
<211> LENGTH: 27
<212> TYPE: DNA
<213> ORGANISM: Artificial Sequence
<220> FEATURE:
<223> OTHER INFORMATION: Met 27254-1

<400> SEQUENCE: 169
ctttagcctt ctcactgata tcgaatg                                     27
```

```
<210> SEQ ID NO 170
<211> LENGTH: 25
<212> TYPE: DNA
<213> ORGANISM: Artificial Sequence
<220> FEATURE:
<223> OTHER INFORMATION: Met 27254-2

<400> SEQUENCE: 170
gcatattctc cccacagata gaaga                                        25

<210> SEQ ID NO 171
<211> LENGTH: 15
<212> TYPE: DNA
<213> ORGANISM: Artificial Sequence
<220> FEATURE:
<223> OTHER INFORMATION: GRHPR-2264-1

<400> SEQUENCE: 171
cctgcccacc cagtg                                                   15

<210> SEQ ID NO 172
<211> LENGTH: 18
<212> TYPE: DNA
<213> ORGANISM: Artificial Sequence
<220> FEATURE:
<223> OTHER INFORMATION: GRHPR-2264-2

<400> SEQUENCE: 172
ctgtgaggtg gagcagtg                                                18

<210> SEQ ID NO 173
<211> LENGTH: 21
<212> TYPE: DNA
<213> ORGANISM: Artificial Sequence
<220> FEATURE:
<223> OTHER INFORMATION: Serpina 279-1

<400> SEQUENCE: 173
tagctcctgg gcatttcttc c                                            21

<210> SEQ ID NO 174
<211> LENGTH: 21
<212> TYPE: DNA
<213> ORGANISM: Artificial Sequence
<220> FEATURE:
<223> OTHER INFORMATION: Serpina 279-2

<400> SEQUENCE: 174
agcttgagga gagcaggaaa g                                            21

<210> SEQ ID NO 175
<211> LENGTH: 20
<212> TYPE: DNA
<213> ORGANISM: Artificial Sequence
<220> FEATURE:
<223> OTHER INFORMATION: Myc 459-1

<400> SEQUENCE: 175
cctggttttc cactacccga                                              20

<210> SEQ ID NO 176
<211> LENGTH: 21
<212> TYPE: DNA
<213> ORGANISM: Artificial Sequence
<220> FEATURE:
<223> OTHER INFORMATION: Myc 459-2
```

<400> SEQUENCE: 176
cactggaact tacaacaccc g                                              21

<210> SEQ ID NO 177
<211> LENGTH: 21
<212> TYPE: DNA
<213> ORGANISM: Artificial Sequence
<220> FEATURE:
<223> OTHER INFORMATION: Serpina 130-1

<400> SEQUENCE: 177
ttcctgctct cctcaagctc t                                              21

<210> SEQ ID NO 178
<211> LENGTH: 21
<212> TYPE: DNA
<213> ORGANISM: Artificial Sequence
<220> FEATURE:
<223> OTHER INFORMATION: Serpina 130-2

<400> SEQUENCE: 178
gagctgaacc aagaaggagg a                                              21

<210> SEQ ID NO 179
<211> LENGTH: 21
<212> TYPE: DNA
<213> ORGANISM: Artificial Sequence
<220> FEATURE:
<223> OTHER INFORMATION: Myc 490-1

<400> SEQUENCE: 179
aggcattcga ctcatctcag c                                              21

<210> SEQ ID NO 180
<211> LENGTH: 21
<212> TYPE: DNA
<213> ORGANISM: Artificial Sequence
<220> FEATURE:
<223> OTHER INFORMATION: Myc 490-2

<400> SEQUENCE: 180
tgcactggaa cttacaacac c                                              21

<210> SEQ ID NO 181
<211> LENGTH: 17
<212> TYPE: DNA
<213> ORGANISM: Artificial Sequence
<220> FEATURE:
<223> OTHER INFORMATION: GRHPR-2179-1

<400> SEQUENCE: 181
tcggagagga ggcagag                                                   17

<210> SEQ ID NO 182
<211> LENGTH: 17
<212> TYPE: DNA
<213> ORGANISM: Artificial Sequence
<220> FEATURE:
<223> OTHER INFORMATION: GRHPR-2179-2

<400> SEQUENCE: 182
ttctcctgag ggcctcc                                                   17

<210> SEQ ID NO 183
<211> LENGTH: 21

```
<212> TYPE: DNA
<213> ORGANISM: Artificial Sequence
<220> FEATURE:
<223> OTHER INFORMATION: GYG-2851-1

<400> SEQUENCE: 183
acagggagaa ggatgtcaga g                                          21

<210> SEQ ID NO 184
<211> LENGTH: 22
<212> TYPE: DNA
<213> ORGANISM: Artificial Sequence
<220> FEATURE:
<223> OTHER INFORMATION: GYG-2851-2

<400> SEQUENCE: 184
gtcctgggat catctctgaa ac                                         22

<210> SEQ ID NO 185
<211> LENGTH: 21
<212> TYPE: DNA
<213> ORGANISM: Artificial Sequence
<220> FEATURE:
<223> OTHER INFORMATION: GYG-2793-1

<400> SEQUENCE: 185
acagggagaa ggatgtcaga g                                          21

<210> SEQ ID NO 186
<211> LENGTH: 21
<212> TYPE: DNA
<213> ORGANISM: Artificial Sequence
<220> FEATURE:
<223> OTHER INFORMATION: GYG-2793-2

<400> SEQUENCE: 186
cactaaccac aaacgatgcc t                                          21

<210> SEQ ID NO 187
<211> LENGTH: 18
<212> TYPE: DNA
<213> ORGANISM: Artificial Sequence
<220> FEATURE:
<223> OTHER INFORMATION: Serpina 79-1

<400> SEQUENCE: 187
gaattcctgg cagcagca                                              18

<210> SEQ ID NO 188
<211> LENGTH: 18
<212> TYPE: DNA
<213> ORGANISM: Artificial Sequence
<220> FEATURE:
<223> OTHER INFORMATION: Serpina 79-2

<400> SEQUENCE: 188
ctactgcctc cacccgaa                                              18

<210> SEQ ID NO 189
<211> LENGTH: 22
<212> TYPE: DNA
<213> ORGANISM: Artificial Sequence
<220> FEATURE:
<223> OTHER INFORMATION: Myc 538-1

<400> SEQUENCE: 189
```

```
taggcattcg actcatctca gc                                              22

<210> SEQ ID NO 190
<211> LENGTH: 21
<212> TYPE: DNA
<213> ORGANISM: Artificial Sequence
<220> FEATURE:
<223> OTHER INFORMATION: Myc 538-2

<400> SEQUENCE: 190
tgcactggaa cttacaacac c                                               21

<210> SEQ ID NO 191
<211> LENGTH: 17
<212> TYPE: DNA
<213> ORGANISM: Artificial Sequence
<220> FEATURE:
<223> OTHER INFORMATION: GYG-2744-1

<400> SEQUENCE: 191
ggaccagggc acctttg                                                    17

<210> SEQ ID NO 192
<211> LENGTH: 23
<212> TYPE: DNA
<213> ORGANISM: Artificial Sequence
<220> FEATURE:
<223> OTHER INFORMATION: GYG-2744-2

<400> SEQUENCE: 192
ggctttctcc agataagata ctg                                             23
```